United States Patent
Kitamura et al.

(10) Patent No.: US 9,287,514 B2
(45) Date of Patent: Mar. 15, 2016

(54) METAL COMPLEX AND DEVICE USING THE METAL COMPLEX

(75) Inventors: Noboru Kitamura, Sapporo (JP); Eri Sakuda, Sapporo (JP); Akitaka Ito, Sapporo (JP); Takeo Hirokawa, Sapporo (JP); Chizu Sekine, Chuo-ku (JP); Yusuke Ishii, Tsukuba (JP)

(73) Assignees: SUMITOMO CHEMICAL COMPANY, LIMITED, Tokyo (JP); NATIONAL UNIVERSITY CORPORATION HOKKAIDO UNIVERSITY, Sapporo-shi, Hokkaido (JP)

( * ) Notice: Subject to any disclaimer, the term of this patent is extended or adjusted under 35 U.S.C. 154(b) by 248 days.

(21) Appl. No.: 13/822,867

(22) PCT Filed: Sep. 12, 2011

(86) PCT No.: PCT/JP2011/070722
§ 371 (c)(1),
(2), (4) Date: Mar. 13, 2013

(87) PCT Pub. No.: WO2012/036119
PCT Pub. Date: Mar. 22, 2012

(65) Prior Publication Data
US 2013/0168615 A1 Jul. 4, 2013

(30) Foreign Application Priority Data

Sep. 15, 2010 (JP) .................................. 2010-206432
Apr. 22, 2011 (JP) .................................. 2011-096445

(51) Int. Cl.
| | | |
|---|---|---|
| H01L 51/00 | (2006.01) | |
| C09K 11/06 | (2006.01) | |
| C07F 15/00 | (2006.01) | |
| H05B 33/14 | (2006.01) | |
| H01L 51/50 | (2006.01) | |

(52) U.S. Cl.
CPC ........ *H01L 51/0085* (2013.01); *C07F 15/0033* (2013.01); *C09K 11/06* (2013.01); *H01L 51/008* (2013.01); *H01L 51/009* (2013.01); *H01L 51/0039* (2013.01); *H05B 33/14* (2013.01); *C09K 2211/1007* (2013.01); *C09K 2211/1014* (2013.01); *C09K 2211/1029* (2013.01); *C09K 2211/185* (2013.01); *H01L 51/0042* (2013.01); *H01L 51/5016* (2013.01)

(58) Field of Classification Search
None
See application file for complete search history.

(56) References Cited

U.S. PATENT DOCUMENTS

| | | |
|---|---|---|
| 2005/0072970 A1 | 4/2005 | Saito |
| 2009/0134384 A1 | 5/2009 | Stoessel et al. |
| 2010/0293782 A1* | 11/2010 | Yamazaki et al. .............. 29/825 |

FOREIGN PATENT DOCUMENTS

| | | |
|---|---|---|
| JP | 2004-315509 A | 11/2004 |
| JP | 2004355898 A | 12/2004 |
| JP | 2005-093098 A | 4/2005 |
| JP | 2006-096934 A | 4/2006 |
| JP | 2008-541417 A | 11/2008 |
| JP | 2010-070488 A | 4/2010 |

OTHER PUBLICATIONS

Li and Meng, Organic Light-Emitting Materials and Devices, Taylor & Francis, 2007, p. 335.*

(Continued)

*Primary Examiner* — Ling Choi
*Assistant Examiner* — Catherine S Branch
(74) *Attorney, Agent, or Firm* — Sughrue Mion, PLLC

(57) ABSTRACT

Disclosed is an device having high light-emitting efficiency. A metal complex represented by the following formula (1).

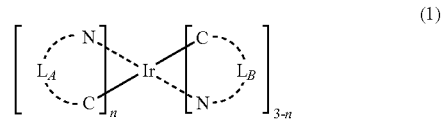

In the formula (1), n represents an integer of 1 to 3. $L_A$ and $L_B$ each independently represent the moiety of a group bonded to an iridium atom, except for coordinating atoms. When n is 3, a metal complex represented by the following formula (1-3):

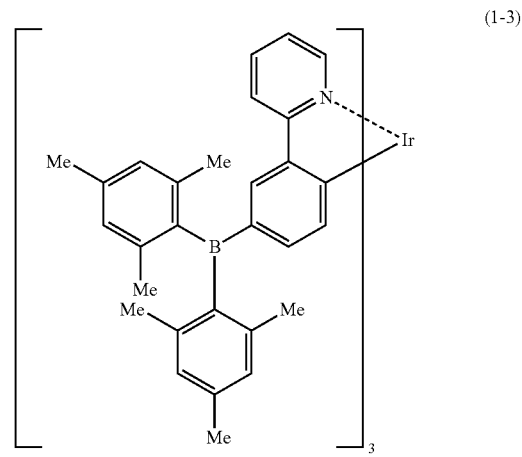

wherein Me represents a methyl group) is excluded.

24 Claims, No Drawings

(56) References Cited

OTHER PUBLICATIONS

Hou et al., "Efficient Solution-Processed Blue Electrophosphorescent Devices Based on a Novel Small-Molecule Host," Chin. Phys. Lett., vol. 25, No. 4 (2008), p. 1457.*
M.A. Baldo, et al., "Very high-efficiency green organic light-emitting devices based on electrophosphorescence", Applied Physics Letters, vol. 75, No. 1, Jul. 5, 1999, pp. 4-6.
Takeshi Sano, et al., "Novel Europium Complex for Electroluminescent Devices with Sharp Red Emission", Jpn. J. Appl. Phys., vol. 34, Part 1, No. 4A, Apr. 1995, pp. 1883-1887.
M.A. Baldo, et al., "High-efficiency fluorescent organic light-emitting devices using a phosphorescent sensitizer", Nature, vol. 403, Feb. 17, 2000, pp. 750-753.
Takeo Hirokawa, et al., "Study on the Intense Emission Mechanism of a New Cyclometalated Iridium (III) Complex that Has Allylboron Substituents", Abstracts of the 22nd Symposium on Photochemistry of Coordination Compounds, 2010, pp. 61-62.
Guijiang Zhou, et al., "Manipulating Charge-Transfer Character with Electron-Withdrawing Main-Group Moieties for the Color Tuning of Iridium Electrophosphors", Advanced Functional Materials, vol. 18, 2008, pp. 499-511.
Takeo Hirokawa, et al., "Synthesis and Photochemical Properties of Cyclometalated Iridium (III) Complex that Has Allylboron Substituents", Abstracts of the 59th JSCC Symposium, vol. 59, Sep. 4, 2009, p. 164.
Takeo Hirokawa, et al., "Synthesis and Spectroscopic Properties of Cyclometalated Iridium (III) Complexes Having Arylborane Charge Transfer Units", Poster Abstracts of the 59th JSCC Symposium, 2010, p. 113.
Youngmin You, et al., "A Phosphorescent Ir(III) Complex for Selective Fluoride Ion Sensing with a High Signal-to-Noise Ratio", Advanced Materials, vol. 20, No. 20, 2008, pp. 3820-3826.
Communication dated Apr. 28, 2015 from the Japanese Patent Office in counterpart application No. 2011-202252.

* cited by examiner

METAL COMPLEX AND DEVICE USING THE METAL COMPLEX

CROSS REFERENCE TO RELATED APPLICATIONS

This application is a National Stage of International Application No. PCT/JP2011/070722 filed Sep. 12, 2011, claiming priority based on Japanese Patent Application Nos. 2010-206432 filed Sep. 15, 2010 and 2011-096445 filed Apr. 22, 2011, the contents of all of which are incorporated herein by reference in their entirety.

TECHNICAL FIELD

The present invention relates to a metal complex, to a composition containing the metal complex, to a metal-containing polymer compound, to a composition containing the metal-containing polymer compound, and to films and devices using them.

BACKGROUND ART

A metal complex that emits light by phosphorescence from an excited triplet state is receiving attention as the light-emitting material used for a light-emitting layer provided in an organic electroluminescent device, because high light-emitting efficiency can be obtained. One known example of such a metal complex is a tris(2-phenylpyridine)iridium complex (see Non Patent Documents 1 to 4).

RELATED ART DOCUMENTS

Non Patent Documents

Non Patent Document 1: Appl. Phys. Lett., (1999), 75(1), 4.
Non Patent Document 2: Jpn. J. Appl. Phys., 34, 1883 (1995).
Non Patent Document 3: Nature, 403, 750 (2000).
Non Patent Document 4: Abstracts of the 22nd symposium on Photochemistry of Coordination Compounds, pp. 61-62, 2010.

DISCLOSURE OF INVENTION

Problem to be Solved by the Invention

However, the solubility of the above conventional metal complex in an organic solvent is not sufficient. Therefore, the conventional metal complex is not suitable for manufacture of a device using a coating method that uses a coating liquid to form a film, and it is difficult to form a device that achieves high light-emitting efficiency.

Accordingly, it is an object of the present invention to provide a metal complex having improved solubility in an organic solvent and thereby to provide a device having improved light-emitting efficiency by using the metal complex.

Means for Solving Problem

The present inventors have made extensive studies and found that the above problem can be solved by following constitutions, and the present invention has been completed.

Accordingly, the present invention provides the following [1] to [26].

[1] A metal complex represented by formula (1) (hereinafter may be referred to as "metal complex N represented by formula (1)"):

[Chemical Formula 1]

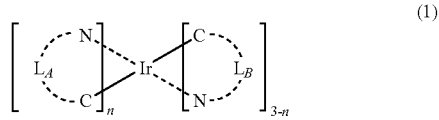

wherein:

in formula (1), n represents an integer of from 1 to 3; $L_A$ and $L_B$ each independently represent a moiety of a group bonded to an iridium atom except for coordinating atoms; a group represented by formula (1-1):

[Chemical Formula 2]

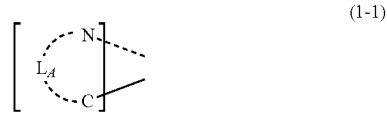

means a group represented by formula (L1):

[Chemical Formula 3]

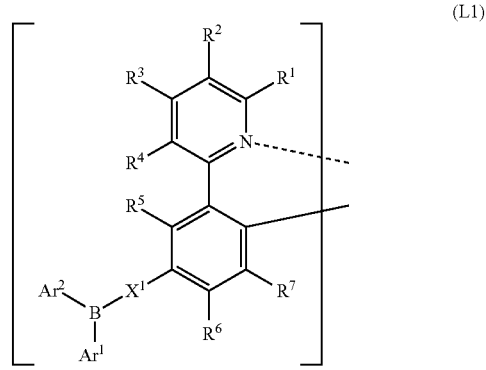

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ each independently represent an aryl group optionally having a substituent or a monovalent aromatic heterocyclic group optionally having a substituent; $X^1$ represents a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by formula (1-2):

[Chemical Formula 4]

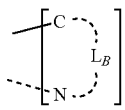
(1-2)

is different from the group represented by the formula (1-1) and means a group represented by a formula (L2):

[Chemical Formula 5]

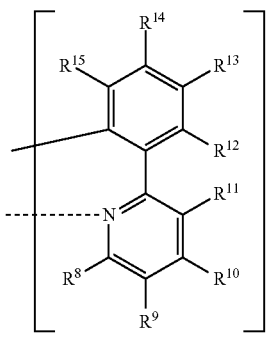
(L2)

wherein, in formula (L2), $R^8$, $R^9$, $R^{10}$, $R^{11}$, $R^{12}$, $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; and when two or three groups represented by the formula (1-1) are present, the groups represented by the formula (1-1) may be the same as or different from each other; and when two groups represented by the formula (1-2) are present, the groups represented by the formula (1-2) may be the same as or different from each other; provided that when n is 3, a metal complex represented by formula (1-3):

[Chemical Formula 6]

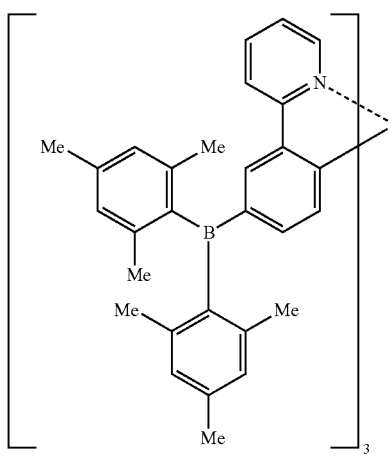
(1-3)

wherein, in formula (1-3), Me represents a methyl group, is excluded.

[2] The metal complex according to above [1], wherein the group represented by the formula (L1) is a group represented by formula (L1-1):

[Chemical Formula 7]

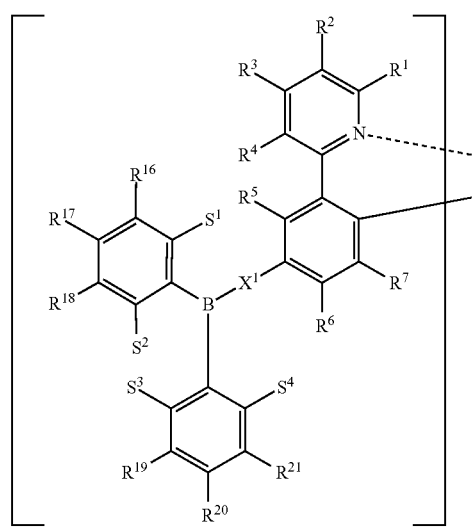
(L1-1)

wherein, in formula (L1-1), $R^1$, $R^2$, $R^3$, $R^4$, $R^5$, $R^6$, $R^7$, and $X^1$ are as defined above; $R^{16}$, $R^{17}$, $R^{18}$, $R^{19}$, $R^{20}$, and $R^{21}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $S^1$, $S^2$, $S^3$, and $S^4$ each independently represent an alkyl group, an alkoxy group, an aryl group, an aralkyl group, a substituted amino group, or a monovalent aromatic heterocyclic group; and these groups may have a substituent.

[3] The metal complex according to above [2], wherein $S^1$, $S^2$, $S^3$, and $S^4$ are each independently an alkyl group, an aryl group, a substituted amino group, or a monovalent aromatic heterocyclic group.

[4] The metal complex according to above [2] or [3], wherein $S^1$, $S^2$, $S^3$, and $S^4$ are each independently an alkyl group or an aryl group.

[5] The metal complex according to any one of above [2] to [4], wherein $S^1$, $S^2$, $S^3$, and $S^4$ are an alkyl group.

[6] The metal complex according to any one of above [1] to [5], wherein $X^1$ is a direct bond.

[7] The metal complex according to any one of above [1] to [6], wherein n is 1 or 2.

[8] The metal complex according to any one of above [2] to [7], wherein at least one of $R^{16}$, $R^{17}$, $R^{18}$, $R^{19}$, $R^{20}$, and $R^{21}$ is an alkyl group.

[9] The metal complex according to any one of above [2] to [6], wherein n is 3, and at least one of $R^{16}$, $R^{17}$, $R^{18}$, $R^{19}$, $R^{20}$, and $R^{21}$ is an alkyl group having 2 or more carbon atoms.

[10] A composition comprising:
a charge transporting material; and
a metal complex represented by formula (1) (hereinafter may be referred to as "metal complex a represented by formula (1)"):

[Chemical Formula 8]

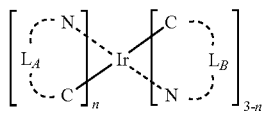
(1)

wherein:
in formula (1), n represents an integer of from 1 to 3; $L_A$ and $L_B$ each independently represent a moiety of a group bonded to an iridium atom except for coordinating atoms; a group represented by formula (1-1):

[Chemical Formula 9]

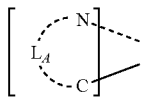
(1-1)

means a group represented by formula (L1):

[Chemical Formula 10]

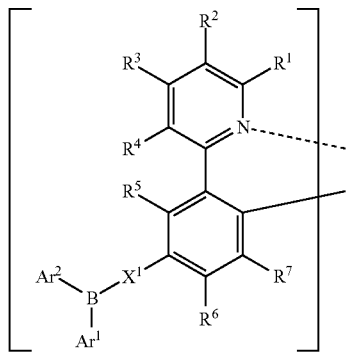
(L1)

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ each independently represent an aryl group optionally having a substituent or a monovalent aromatic heterocyclic group optionally having a substituent; $X^1$ represents a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by formula (1-2):

[Chemical Formula 11]

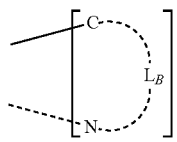
(1-2)

is different from the group represented by the formula (1-1) and means a group represented by formula (L2):

[Chemical Formula 12]

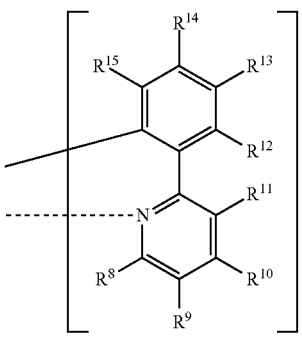
(L2)

wherein, in formula (L2), $R^8$, $R^9$, $R^{10}$, $R^{11}$, $R^{12}$ $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; and
when two or three groups represented by the formula (1-1) are present, the groups represented by the formula (1-1) may be the same as or different from each other; and when two groups represented by the formula (1-2) are present, the groups represented by the formula (1-2) may be the same as or different each other.

[11] The composition according to above [10], wherein the charge transporting material is a polymer compound.

[12] The composition according to above [10] or [11], wherein the charge transporting material is a polymer compound having, as a structural unit, at least one group selected from among the group consisting of a bivalent aromatic amine residue, an arylene group, and a bivalent aromatic heterocyclic group.

[13] The composition according to any one of above [10] to [12], wherein the charge transporting material is a polymer compound having, as structural units, at least two groups selected from among the group consisting of a bivalent aromatic amine residue, an arylene group, and a bivalent aromatic heterocyclic group.

[14] A metal-containing polymer compound comprising: as a structural unit, a group derived from a metal complex a represented by the above formula (1).

[15] The metal-containing polymer compound according to above [14], wherein the metal-containing polymer compound comprises, as a structural unit, at least one group selected from among the group consisting of a bivalent aromatic amine residue, an arylene group, and a bivalent aromatic heterocyclic group.

[16] The metal-containing polymer compound according to above [14] or [15], wherein the metal-containing polymer compound comprises, as structural units, at least two groups selected from among the group consisting of a bivalent aromatic amine residue, an arylene group, and a bivalent aromatic heterocyclic group.

[17] A composition comprising:
the metal-containing polymer compound according to above [14] to [16]; and
a charge transporting material.

[18] A composition comprising:
a solvent and dispersion medium; and
a metal complex N represented by the above formula (1).

[19] The composition according to any one of above [10] to [13] or [17], further comprising a solvent or a dispersion medium.

[20] A composition comprising the metal-containing polymer compound according above [14], and a solvent or a dispersion medium.

[21] A film comprising a metal complex a represented by the above formula (1).

[22] A film comprising the metal-containing polymer compound according to any one of above [14] to [16].

[23] A film comprising the composition according to any one of above [10] to [13] or [17].

[24] A device comprising the film according to any one of above [21] to [23].

[25] A device comprising the film according to above [22].

[26] The device according to above [24], wherein the device is a light-emitting device.

Effect of the Invention

The metal complex of the present invention has higher solubility in an organic solvent than the above conventional metal complex.

The use of the metal complex, metal-containing polymer compound, or composition of the present invention as the material of the light-emitting layer of a device can improve film quality. Therefore, the light-emitting efficiency of the device can be improved as compared to that of a device using the above conventional metal complex (tris(2-phenylpyridine)iridium complex) as the material of the light-emitting layer.

The metal complex of the present invention has high solubility in an organic solvent, as described above. Therefore, the metal complex can be suitably used to manufacture a device by using a coating method that uses a coating liquid to form a film.

Accordingly, the device can be manufactured using a simple process.

SPECIFICATION OF EMBODIMENTS

The present invention will next be described in detail. In structural formulae (chemical formulae) shown in the present specification, a bond denoted by a broken line connecting an iridium atom (Ir) and a nitrogen atom (N) represents a coordinate bond.

<Explanation of Terms>

In the present specification, the term "X-valent aromatic heterocyclic group (X is 1 or 2)" means a remaining atomic group obtained by removing X hydrogen atoms from an aromatic heterocyclic compound and is used to include a group having a condensed ring. The term "heterocyclic compound" means an organic compound having a cyclic structure in which atoms forming the ring comprise not only carbon atoms but also a heteroatom such as an oxygen atom, a sulfur atom, a nitrogen atom, a phosphorus atom, a boron atom, and a silicon atom. The term "aromatic heterocyclic compound" is a heterocyclic compound comprising the above heteroatom such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole, and dibenzophosphole and means: a compound in which its heterocyclic ring itself exhibits aromaticity; and a compound such as phenoxazine, phenothiazine, dibenzoborole, dibenzosilole, and benzopyran in which the heteroatom-containing heterocyclic ring itself does not exhibit aromaticity but an aromatic ring is condensed with the heterocyclic ring.

In the present specification, Me represents a methyl group, and Et represents an ethyl group. R represents a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom, or a cyano group. A plurality of Rs may be the same as or different from each other. A group represented by R may optionally have a substituent.

In the present specification, Ra represents an alkyl group, an aryl group, a monovalent aromatic heterocyclic group, or an aralkyl group. A plurality of Ras may be the same as or different from each other. When Ras is pluraly present in a single group, these may together form a cyclic structure. A group represented by Ra may optionally have a substituent.

In the present specification, the term "structural unit" means a unit that appears at least once in a polymer compound and is preferably present in the polymer compound as a "repeating unit" (i.e., a unit that appears at least twice in the polymer compound).

<Explanation of Substituents>

In the present specification, the term "substituent" used has the following meanings, unless otherwise specifically stated.

—Alkyl Group—

In the present specification, the alkyl group may be any of linear, branched, and cyclic groups, and the number of carbon atoms in the alkyl group is generally 1 to 20. Examples of the alkyl group include a methyl group, an ethyl group, a propyl group, an isopropyl group, a butyl group, a sec-butyl group, an isobutyl group, a tert-butyl group, a pentyl group, an isoamyl group, a hexyl group, a cyclohexyl group, a heptyl group, an octyl group, a 2-ethylhexyl group, a nonyl group, a decyl group, a 3,7-dimethyloctyl group, a dodecyl group, a trifluoromethyl group, a pentafluoroethyl group, a perfluorobutyl group, a perfluorohexyl group, and a perfluorooctyl group.

—Aryl Group—

In the present specification, the aryl group is a remaining atomic group obtained by removing one hydrogen atom from an aromatic hydrocarbon compound, and the term "aryl group" is used to comprise a group having a condensed ring. The number of carbon atoms in the aryl group is generally 6 to 60, preferably 6 to 48, more preferably 6 to 20, and still more preferably 6 to 14. The above number of carbon atoms does not comprise the number of carbon atoms in a substituent. A hydrogen atom in the aryl group may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom, or a cyano group. Examples of the aryl group include substituted and unsubstituted phenyl group and the like.

—Monovalent Aromatic Heterocyclic Group—

In the present specification, the number of carbon atoms in the monovalent aromatic heterocyclic group is generally 2 to 60, preferably 3 to 60, and more preferably 3 to 20. The above number of carbon atoms does not comprise the number of carbon atoms in a substituent. Examples of the monovalent aromatic heterocyclic group include a 2-oxadiazolyl group, a 2-thiadiazolyl group, a 2-thiazolyl group, a 2-oxazolyl group, a 2-thienyl group, a 2-pyrrolyl group, a 2-furyl group, a 2-pyridyl group, a 3-pyridyl group, a 4-pyridyl group, a 2-pyrazyl group, a 2-pyrimidyl group, a 2-triazyl group, a 3-pyridazyl group, a 3-carbazolyl group, a 2-phenoxazinyl group, a 3-phenoxazinyl group, a 2-phenothiazinyl group, and a 3-phenothiazinyl group. A hydrogen atom in the monovalent aromatic heterocyclic group may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom, or a cyano group.

—Alkoxy Group—

In the present specification, the alkoxy group is any of linear, branched, and cyclic groups, and the number of carbon atoms in the alkoxy group is generally 1 to 20. Examples of the alkoxy group include a methoxy group, an ethoxy group, a propyloxy group, an isopropyloxy group, a butoxy group, a sec-butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a dodecyloxy group, a trifluoromethoxy group, a pentafluoroethoxy group, a perfluorobutoxy group, a perfluorohexyloxy group, a perfluorooctyloxy group, a methoxymethyloxy group, a 2-methoxyethyloxy group, and a 2-ethoxyethyloxy group.

—Aryloxy Group—

In the present specification, the number of carbon atoms in the aryloxy group is generally 6 to 60. Examples of the aryloxy group include a phenoxy group, $C_1$ to $C_{12}$ alkoxy phenoxy groups ("$C_1$ to $C_{12}$ alkoxy" means that the number of carbon atoms in the alkoxy moiety in each group is 1 to 12. The same applies to the following), $C_1$ to $C_{12}$ alkyl phenoxy groups ("$C_1$ to $C_{12}$ alkyl" means that the number of carbon atoms in the alkyl moiety in each group is 1 to 12. The same applies to the following), a 1-naphthyloxy group, a 2-naphthyloxy group, and a pentafluorophenyloxy group.

—Aralkyl Group—

In the present specification, the number of carbon atoms in the aralkyl group is generally 7 to 60. Examples of the aralkyl group include phenyl-$C_{1-12}$ alkyl groups, $C_{1-12}$ alkoxy phenyl-$C_{1-12}$ alkyl groups, and $C_{1-12}$ alkyl phenyl-$C_{1-12}$ alkyl groups.

—Arylalkoxy Group—

In the present specification, the number of carbon atoms in the arylalkoxy group is generally 7 to 60. Examples of the arylalkoxy group include phenyl-$C_{1-12}$ alkoxy groups, $C_{1-12}$ alkoxy phenyl-$C_{1-2}$ alkoxy groups, $C_{1-12}$ alkyl phenyl-$C_{1-12}$ alkoxy groups and the like.

—Substituted Amino Group—

In the present specification, the number of carbon atoms in the substituted amino group is generally 2 to 60. Examples of the substituted amino group include an amino group in which a hydrogen atom in the group is substituted with an alkyl group, an aryl group, an aralkyl group, or a monovalent aromatic heterocyclic group. In the substituted amino group, a plurality of substituents in the group may be directly bonded or bonded via a carbon atom, an oxygen atom, a sulfur atom and the like, thus forming a condensed ring. The substituted amino group is preferably dialkyl-substituted amino groups or diaryl-substituted amino groups. Specific examples of the substituted amino group include a dimethylamino group, a diethylamino group, a diphenylamino group, a di-4-tolylamino group, a di-4-tert-butylphenylamino group, a bis(3,5-di-tert-butylphenyl)amino group, an N-carbazolyl group, an N-phenoxazinyl group, an N-acridinyl group, and an N-phenothiazinyl group.

—Substituted Carbonyl Group—

In the present specification, the number of carbon atoms in the substituted carbonyl group is generally 2 to 60. Examples of the substituted carbonyl group include a carbonyl group in which a hydrogen atom in the group is substituted with an alkyl group, an aryl group, an aralkyl group, or a monovalent aromatic heterocyclic group. Specific examples of the substituted carbonyl group include an acetyl group, a butyryl group, and a benzoyl group.

—Substituted Carboxyl Group—

In the present specification, the number of carbon atoms in the substituted carboxyl group is generally 2 to 60. Examples of the substituted carboxyl group include a carboxyl group in which a hydrogen atom in the group is substituted with an alkyl group, an aryl group, an aralkyl group, or a monovalent aromatic heterocyclic group. Specific examples of the substituted carboxyl group include a methoxycarbonyl group, an ethoxycarbonyl group, a butoxycarbonyl group, a phenoxycarbonyl group, and a benzyloxycarbonyl group.

—Arylene Group—

In the present specification, the arylene group means a remaining atomic group obtained by removing two hydrogen atoms from an aromatic hydrocarbon compound, and the term "arylene group" is used to include a group having a condensed ring. The number of carbon atoms in the arylene group is generally 6 to 60, and a hydrogen atom in the arylene group may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom, or a cyano group. The above number of carbon atoms does not comprise the number of carbon atoms in a substituent. Examples of the arylene group include: phenylene groups such as a 1,4-phenylene group represented by the formula 001 below, a 1,3-phenylene group represented by the formula 002 below, a 1,2-phenylene group represented by the formula 003 below; naphthalenediyl groups such as a naphthalene-1,4-diyl group represented by the formula 004 below, a naphthalene-1,5-diyl group represented by the formula 005 below, and a naphthalene-2,6-diyl group represented by the formula 006 below; dihydrophenanthrenediyl groups such as a 9,10-dihydrophenanthrene-2,7-diyl group represented by the formula 007 below; and fluorenediyl groups such as a fluorene-3,6-diyl group represented by the formula 008 below and a fluorene-2,7-diyl group represented by the formula 009 below.

[Chemical formula 13]

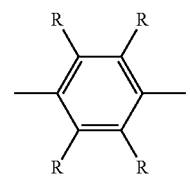

001

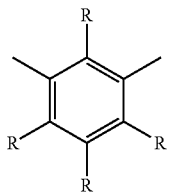

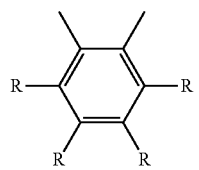

[Chemical formula 14]

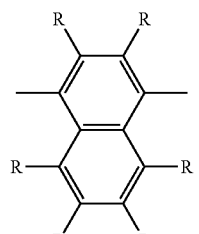

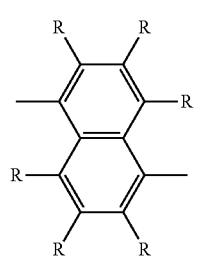

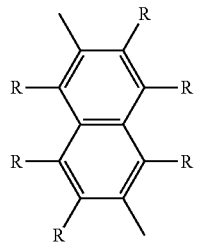

[Chemical formula 15]

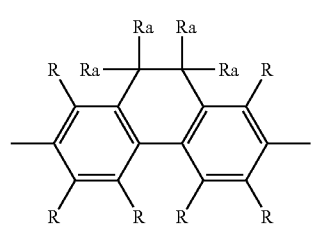

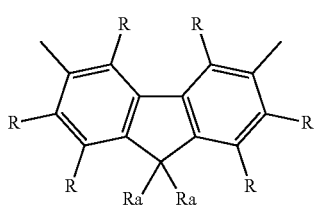

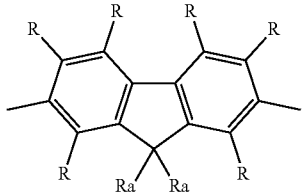

In the formulae 001 to 009, R and Ra are as defined above.

In the formulae 001 to 009, each R is preferably a hydrogen atom, an alkyl group, an aryl group, a monovalent aromatic heterocyclic group, an alkoxy group, an aryloxy group, an aralkyl group, or a substituted amino group and is more preferably a hydrogen atom, an alkyl group, or an aryl group.

In the formulae 001 to 009, each Ra is preferably an aryl group optionally having a substituent or an alkyl group optionally having a substituent and is more preferably an aryl group optionally substituted with an alkyl group, an alkoxy group, or an aryl group or an alkyl group optionally substituted with an alkyl group, an alkoxy group, or an aryl group.

In the formulae 001 to 009, a cyclic structure that may be formed when a plurality of Ras are present is preferably a cyclopentyl ring optionally substituted with an alkyl group, a cyclohexyl ring optionally substituted with an alkyl group, or a cycloheptyl ring optionally substituted with an alkyl group.

—Bivalent Aromatic Heterocyclic Group—

In the present specification, the bivalent aromatic heterocyclic group is a remaining atomic group obtained by removing two hydrogen atoms from an aromatic heterocyclic compound, and the term "bivalent aromatic heterocyclic group" is used to comprise a group having a condensed ring. The number of carbon atoms in the bivalent aromatic heterocyclic group is generally 3 to 60. The above number of carbon atoms does not comprise the number of carbon atoms in a substituent. Examples of the bivalent aromatic heterocyclic group include: pyridinediyl groups such as a pyridine-2,5-diyl group represented by the formula 101 below and a pyridine-2,6-diyl group represented by the formula 102 below; pyrimidinediyl groups such as a pyrimidine-4,6-diyl group represented by the formula 103 below; a triazine-2,4-diyl group represented by the formula 104 below; pyrazinediyl groups such as a pyrazine-2,5-diyl group represented by the formula 105 below; pyridazinediyl groups such as a pyridazine-3,6-diyl group represented by the formula 106 below; quinolinediyl groups such as a quinoline-2,6-diyl group represented by the formula 107 below; isoquinolinediyl groups such as an isoquinoline-1,4-diyl group represented by the formula 108 below; quinoxalinediyl groups such as a quinoxaline-5,8-diyl group represented by the formula 109 below; carbazolediyl groups represented by, for example, formulae 110 and 111 below; dibenzofurandiyl groups represented by, for example, formulae 112 and 113 below; dibenzothiophenediyl groups represented by, for example, formulae 114 and 115 below; dibenzosilolediyl groups represented by, for example, formulae 116 and 117 below; phenoxazinediyl groups represented by, for example, formulae 118 and 119 below; phenothiazinediyl groups represented by, for example, formulae 120 and 121 below; dihydroacridinediyl groups represented by, for example, formula 122 below; a bivalent group represented by the formula 123 below; pyrrolediyl groups such as a pyrrole-2,5-diyl group represented by the formula 124 below; furandiyl groups such as a furan-2,5-diyl group represented by the formula 125 below; thiophenediyl groups such as a thiophene-2,5-diyl group represented by the formula 126 below; diazolediyl groups such as a diazole-2,5-diyl group represented by the formula 127 below; triazolediyl groups such as a triazole-2,5-diyl group represented by the formula 128 below; oxazolediyl groups such as an oxazole-2,5-diyl group represented by the formula 129 below; an oxadiazole-2,5-diyl group represented by the formula 130 below; thiazolediyl groups such as a thiazole-2,5-diyl group represented by the formula 131 below; and a thiadiazole-2,5-diyl group represented by the formula 132 below. A hydrogen atom in each of the above bivalent aromatic heterocyclic groups may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom, or a cyano group.

[Chemical formula 16]

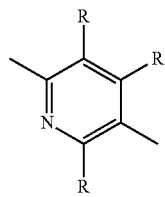
101

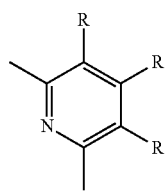
102

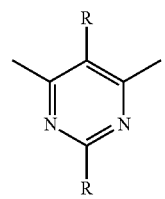
103

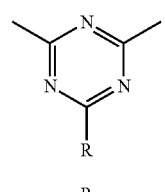
104

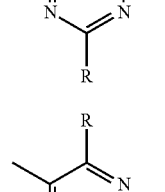
105

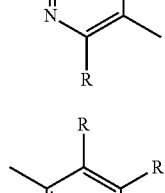
106

[Chemical formula 17]

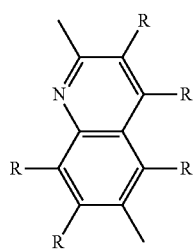
107

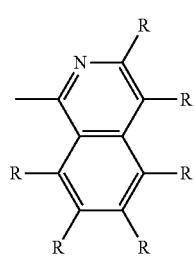
108

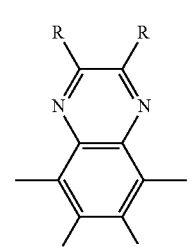
109

[Chemical formula 18]

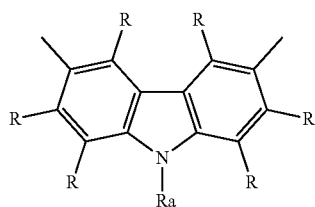
110

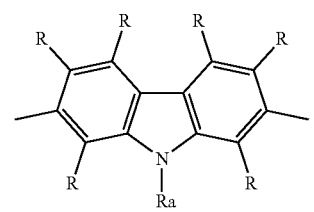
111

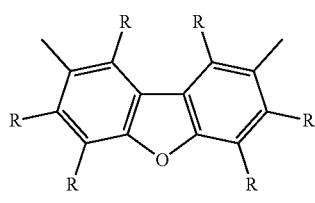
112

-continued
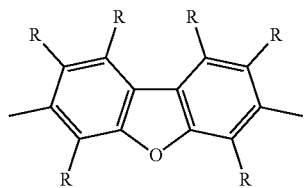
113
[Chemical formula 19]
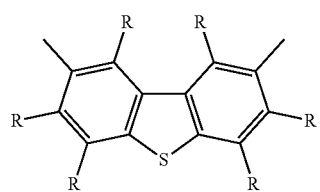
114
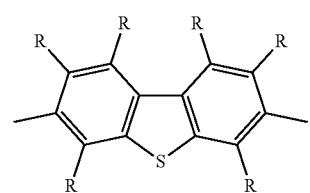
115
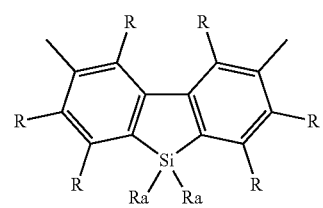
116
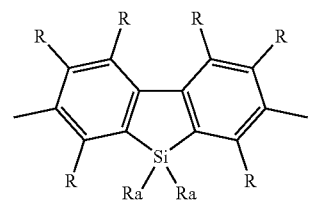
117
[Chemical formula 20]
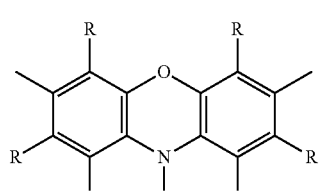
118
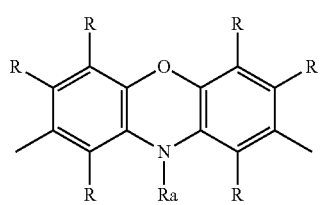
119
-continued
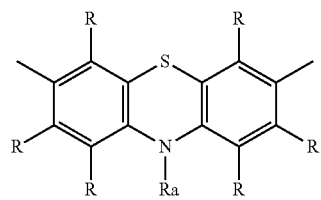
120
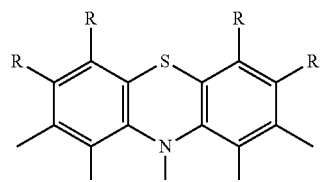
121
[Chemical formula 21]
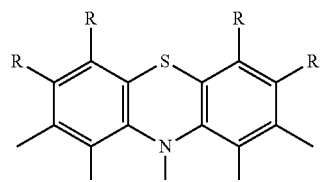
122
123
[Chemical formula 22]
124
125
126

-continued

[Chemical formula 23]

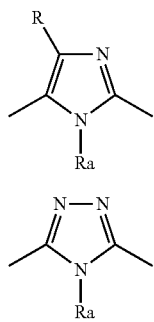

127

128

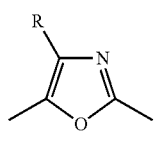

129

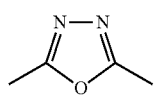

130

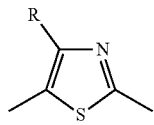

131

132

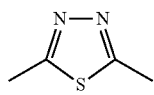

In the formulae 101 to 132, R and Ra are as defined above.
—Alkenyl Group—
In the present specification, the alkenyl group may be any of linear, branched, and cyclic groups, and the number of carbon atoms in the alkenyl group is generally 2 to 20. Examples of the alkenyl group include a group obtained by replacing a direct bond between two adjacent carbon atoms in any of the above alkyl groups having 2 or more carbon atoms with a double bond.
—Alkynyl Group—
In the present specification, the alkynyl group may be any of linear, branched, and cyclic groups, and the number of carbon atoms in the alkynyl group is generally 2 to 20. Examples of the alkynyl group include a group obtained by replacing a direct bond between two adjacent carbon atoms in any of the above alkyl groups having 2 or more carbon atoms with a triple bond.
—Halogen Atom—
In the present specification, examples of the halogen atom include a fluorine atom, a chlorine atom, a bromine atom, and an iodine atom.

<Metal Complex>
The metal complex of the present invention is represented by the formula (1) below. Hereinafter, a metal complex N represented by the formula (1) and a metal complex a represented by the formula (1) are collectively described as a metal complex represented by the formula (1).

[Chemical formula 24]

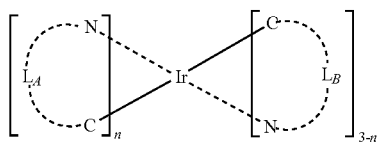

(1)

In the formula (1), n represents an integer of 1 to 3. $L_A$ and $L_B$ each independently represent a moiety of a group bonded to an iridium atom, except for coordinating atoms.

Namely, the metal complex represented by the formula (1) above is composed of an iridium atom and bidentate ligands.

In the formula (1), n is preferably 1 or 2 in terms of the solubility of the metal complex in a solvent, in terms of the applicability of the metal complex to the step of forming a film by a coating method, or in terms of the formation of a film by a vacuum evaporation method.

In the formula (1), n is preferably 1 or 2 because higher light-emitting efficiency is obtained when a device is formed with a light-emitting layer containing the metal complex.

In the formula (1), n is preferably 3 in terms of easy synthesis of the metal complex.

In the formula (1), when n is 1, a plurality of groups represented by the formula (L2) preferably have the same structure, in terms of easy synthesis of the metal complex.

In the formula (1), when n is 1, the plurality of groups represented by the formula (L2) preferably have mutually different structures, in terms of the solubility of the metal complex in a solvent or in terms of the applicability of the metal complex to the step of forming a film by a coating method.

In the formula (1), when n is 2, a plurality of groups represented by the formula (L1) preferably have the same structure, in terms of easy synthesis of the metal complex.

In the formula (1), when n is 2, the plurality of groups represented by the formula (L1) preferably have mutually different structures, in terms of the solubility of the metal complex in a solvent or in terms of the applicability of the metal complex to the process of forming a film by a coating method.

In the formula (1), when n is 3, the plurality of groups represented by the formula (L1) preferably have the same structure, in terms of easy synthesis of the metal complex.

In the formula (1), when n is 3, at least one of the plurality of groups represented by the formula (L1) preferably has a structure different from the structure of the other groups, in terms of the solubility of the metal complex in a solvent or in terms of the applicability of the metal complex to the step of forming a film by a coating method.

In the formula (1), the group represented by the formula (1-1) below:

[Chemical formula 25]

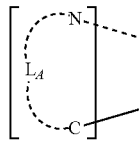

(1-1)

means a group represented by the formula (L1) below.

[Chemical formula 26]

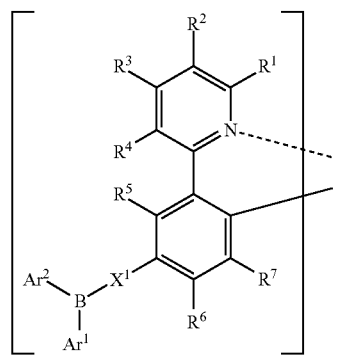

(L1)

In the formula (L1), $R^1$, $R^2$, $R^3$, $R^4$, $R^5$, $R^6$, and $R^7$ each independently represent a hydrogen atom, an alkyl group, an aryl group, a monovalent aromatic heterocyclic group, an alkoxy group, an aryloxy group, an aralkyl group, an aryalkoxy group, a substituted amino group, a substituted carbonyl group, a substituted carboxyl group, an alkenyl group, an alkynyl group, a halogen atom, or a cyano group. $Ar^1$ and $Ar^2$ each independently represent an aryl group or a monovalent aromatic heterocyclic group. $X^1$ represents an arylene group, a bivalent aromatic heterocyclic group, an ethynylene group, a direct bond or a bivalent group in which two or more groups selected from among the group consisting of arylene groups, bivalent aromatic heterocyclic groups, and an ethynylene group are directly bonded to each other.

In the formula (L1), two of the groups represented by $R^1$, $R^2$, $R^3$, $R^4$, $R^5$, $R^6$, and $R^7$ may be directly bonded to each other or bonded via a group represented by —O—, a group represented by —S—, a group represented by —C(=O)—, a group represented by —C(=O)—O—, a group represented by —N($R^4$)—, a group represented by —C(=O)—N($R^4$)—, or a group represented by —C($R^4$)$_2$— to thereby form a five-membered ring, a six-membered ring, or a seven-membered ring. Here, $R^4$ represents an alkyl group, an aryl group, or a monovalent aromatic heterocyclic group.

When two of the groups represented by $R^1$, $R^2$, $R^3$, $R^4$, $R^5$, $R^6$, and $R^7$ in the formula (L1) above form a five-membered ring, a six-membered ring, or a seven-membered ring, examples of the group represented by the formula (L1) include structures represented by the formulae L1-Cy001 to L1-Cy009 below. In terms of easy synthesis of the metal complex, L1-Cy001, L1-Cy002 and L1-Cy005 are preferable, and L1-Cy001 is more preferable.

[Chemical formula 27]

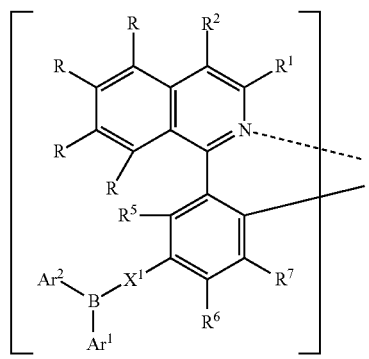

L1-Cy001

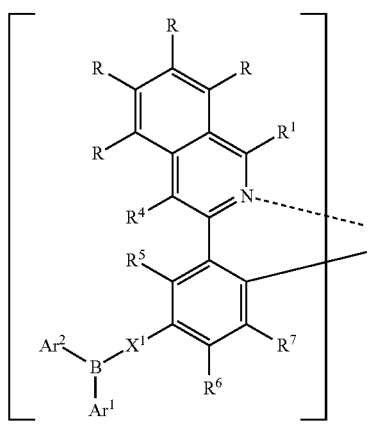

L1-Cy002

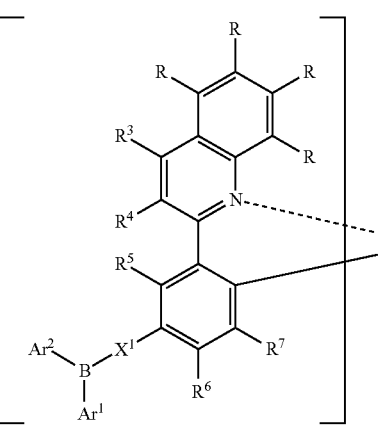

L1-Cy003

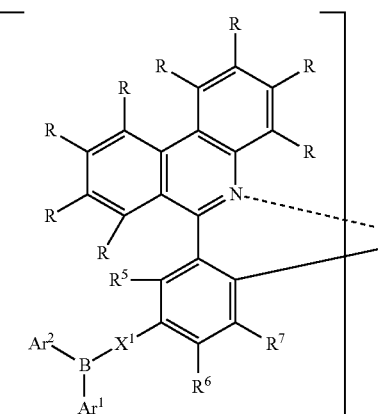

L1-Cy004

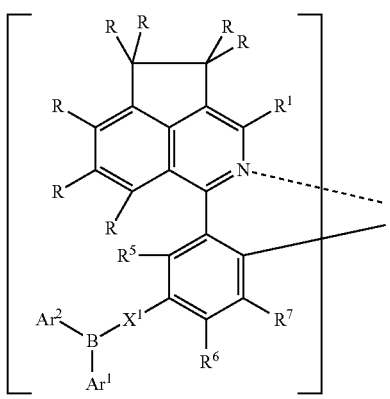
L1-Cy005

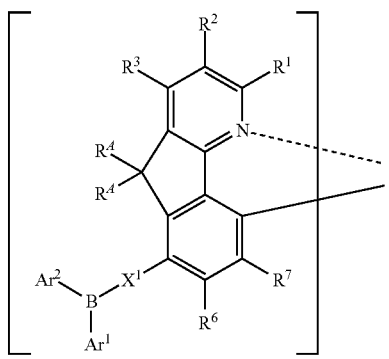
L1-Cy006

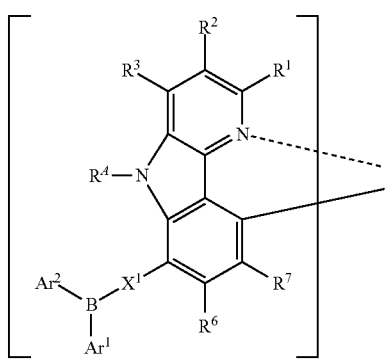
L1-Cy007

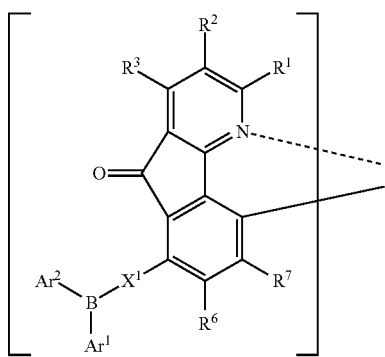
L1-Cy008

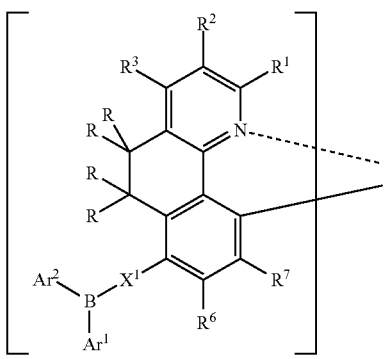
L1-Cy009

In the formulae L1-Cy001 to L1-Cy009, R, $R^4$, $R^1$, $R^2$, $R^3$, $R^4$, $R^5$, $R^6$, $R^7$, $X^1$, $Ar^1$, and $Ar^2$ are as defined above.

In the formula (L1), $R^1$, $R^2$, $R^3$, $R^4$, $R^5$, $R^6$, and $R^7$ are each preferably a hydrogen atom because of easy synthesis of the metal complex.

In the formula (L1), $X^1$ is preferably a single bond or an arylene group and more preferably a single bond, in terms of the light-emitting characteristics of a device to be formed.

In the formula (L1), in terms of easy synthesis of the metal complex, $X^1$ is preferably a single bond, an arylene group, or a group represented as a combination of an arylene group and an ethynylene group and more preferably a single bond.

In the formula (L1), when $X^1$ is an arylene group, $X^1$ is preferably a 1,4-phenylene group or a 4,4'-biphenylene group and more preferably a 1,4-phenylene group. These arylene groups may have a substituent, and the substituent is preferably an alkyl group, an aryl group, a monovalent aromatic heterocyclic group, or an aralkyl group and more preferably an alkyl group or an aralkyl group.

In the formula (L1), the groups represented by $Ar^1$ and $Ar^2$ are each preferably an aryl group optionally having a substituent or a monovalent aromatic heterocyclic group optionally having a substituent, more preferably an aryl group optionally having a substituent, still more preferably an aryl group having a substituent selected from among the group consisting of alkyl groups, alkoxy groups, and aryl groups, particularly preferably a phenyl group having an aromatic dendrimer structure and having a substituent selected from among the group consisting of alkyl groups and alkoxy groups, and more particularly preferably a phenyl group having an aromatic dendrimer structure and having an alkyl group as a substituent, in terms of the solubility of the metal complex in a solvent and in terms of the light-emitting characteristics of a device to be formed. Preferred examples of the aryl group optionally having a substituent include a phenyl group, a 1-naphthyl group, a 2-naphthyl group, and a 9-anthryl group, and examples of the phenyl group having an aromatic dendrimer structure and having an alkyl group as a substituent include a 1,1':3',1''-terphenyl-5-yl group having an alkyl group as a substituent and a 5',5'''-diphenyl-[1,1':3', 1'':3'',1''':3''',1''''-quinquephenyl]-5-yl group having an alkyl group as a substituent.

In the formula (L1), the groups represented by $Ar^1$ and $Ar^2$ are each preferably an aryl group optionally having a substituent and more preferably a phenyl group optionally having a substituent or a 9-anthryl group optionally having a substituent, in terms of easy synthesis of the metal complex.

In the formula (L1), the groups represented by $Ar^1$ and $Ar^2$ preferably have the same structure, in terms of easy synthesis of the metal complex.

Examples of the group represented by the formula (L1) above include groups represented by the formulae (L1-001) to (L1-037) below. In terms of the light-emitting characteristics of a device to be formed, the formula (L1) is preferably any of (L1-001) to (L1-004), (L1-008) to (L1-011), (L1-025), (L1-027), (L1-029), and (L1-030), more preferably (L1-001), (L1-003), (L1-004), (L1-025), (L1-027), (L1-029), or (L1-030), and still more preferably (L1-001), (L1-003), or (L1-004).
[Chemical formula 28]
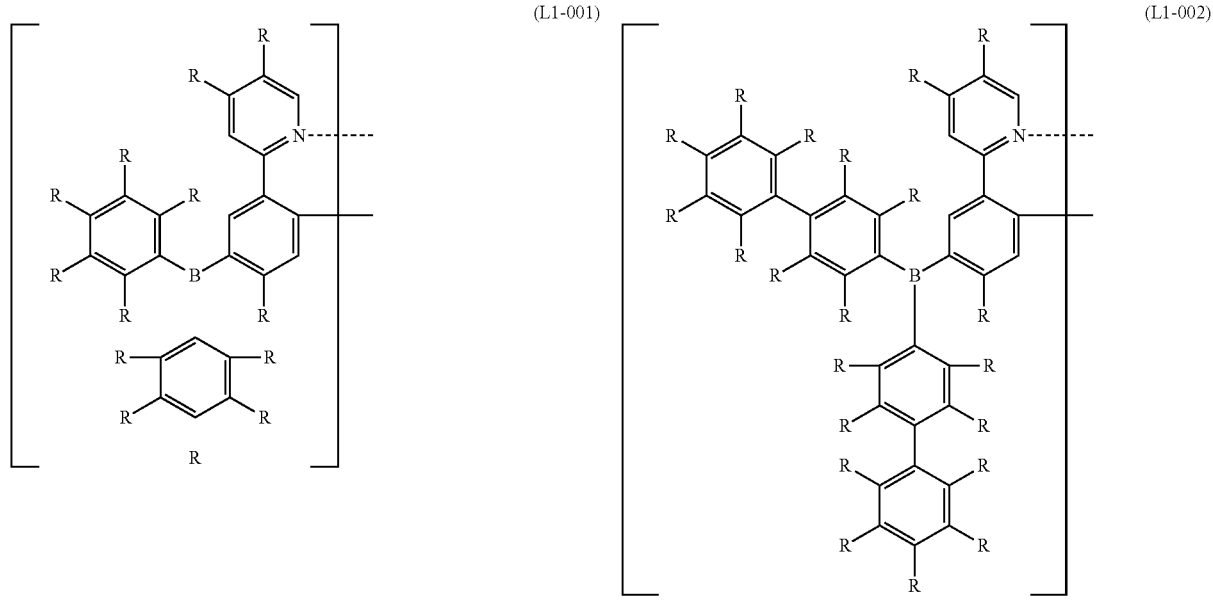
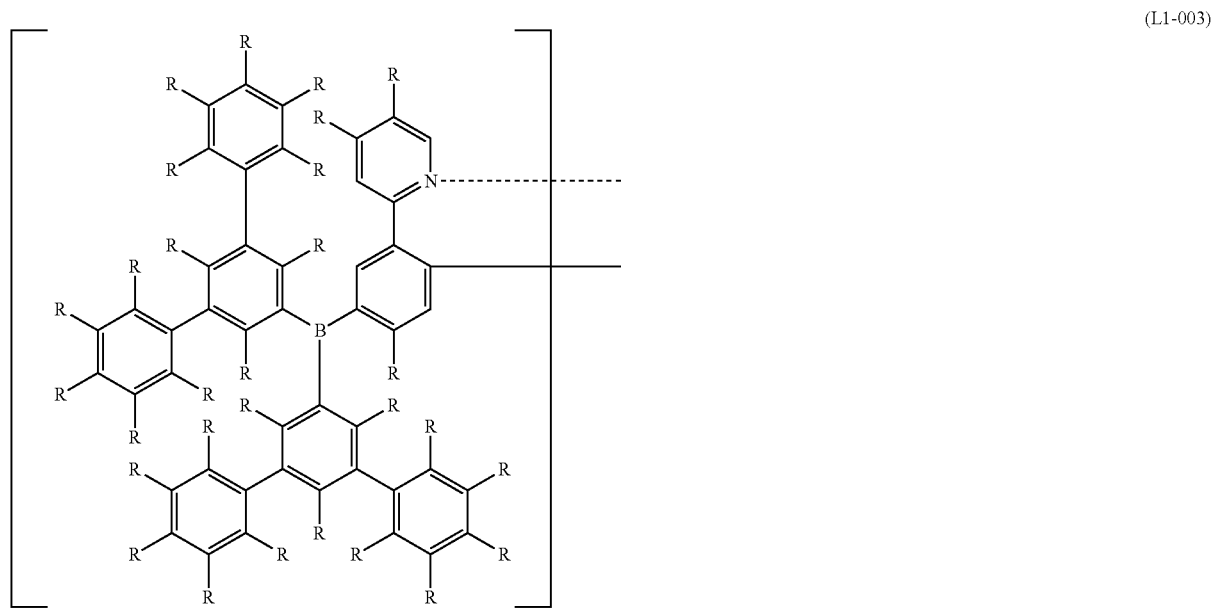

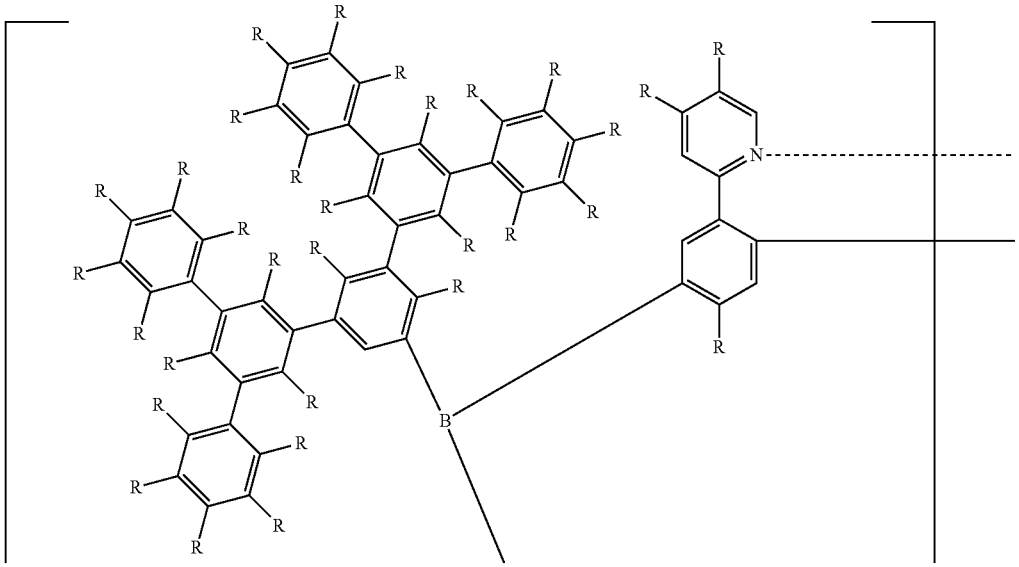
(L1-004)
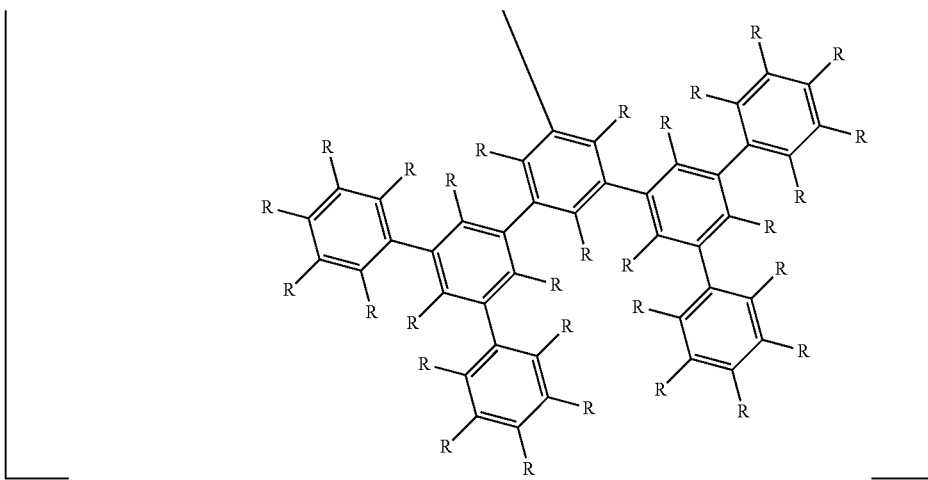
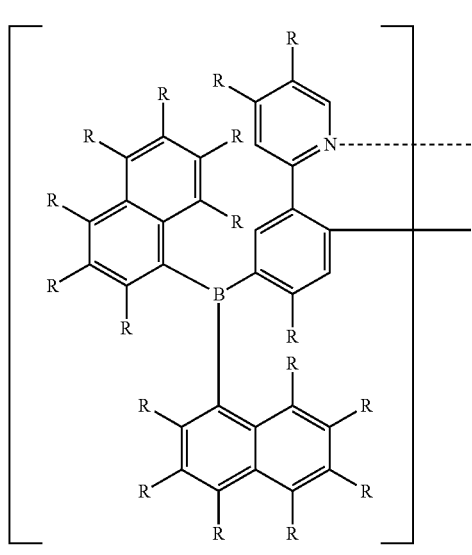
(L1-005)
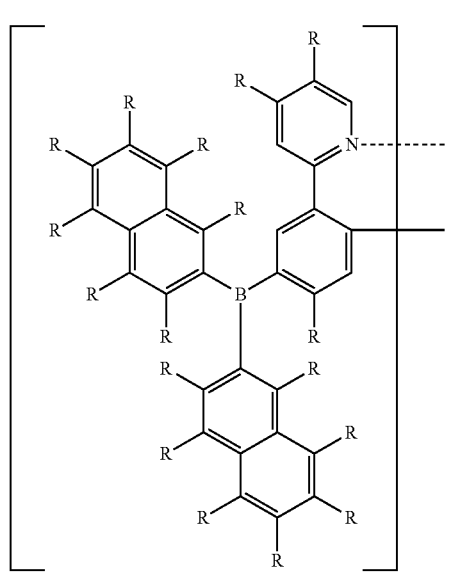
(L1-006)

-continued
(L1-007) 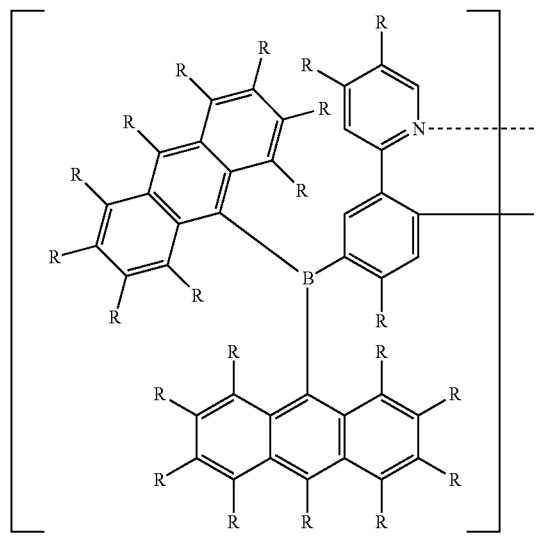
(L1-008) 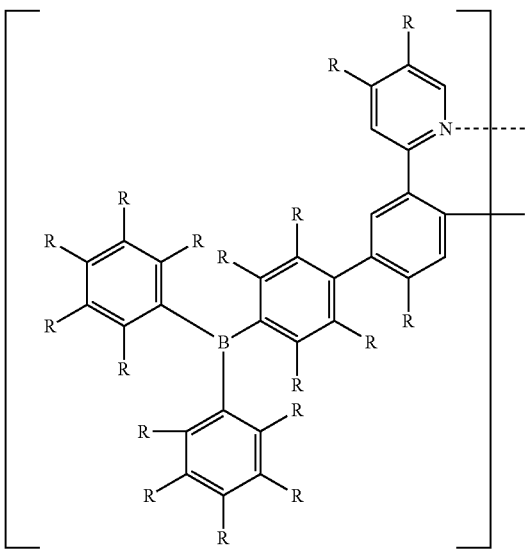
[Chemical formula 29]
(L1-009) 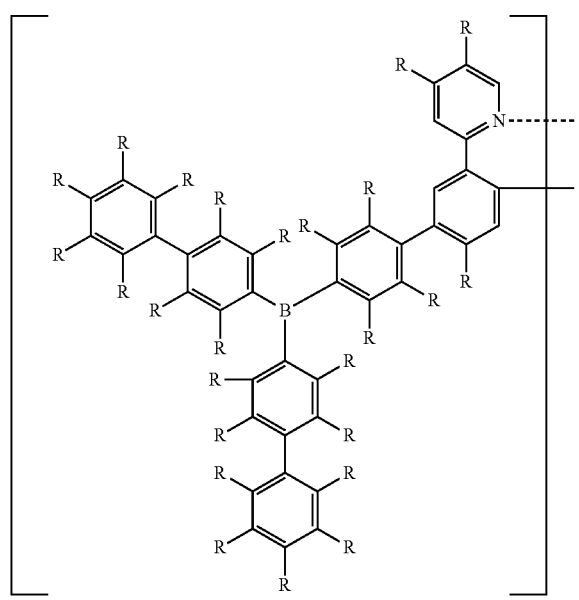
(L1-010) 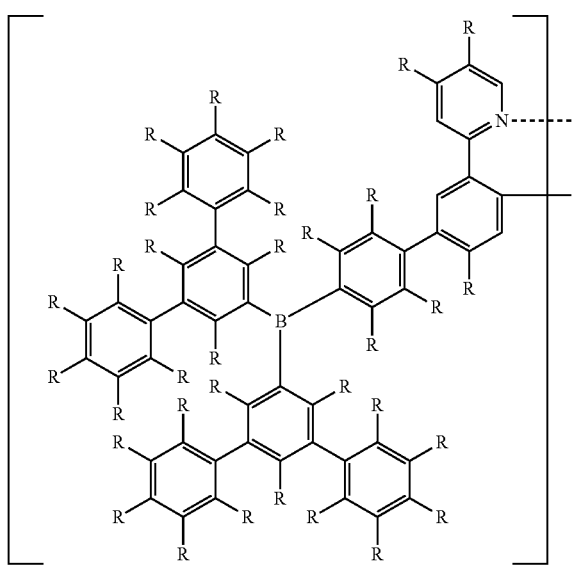

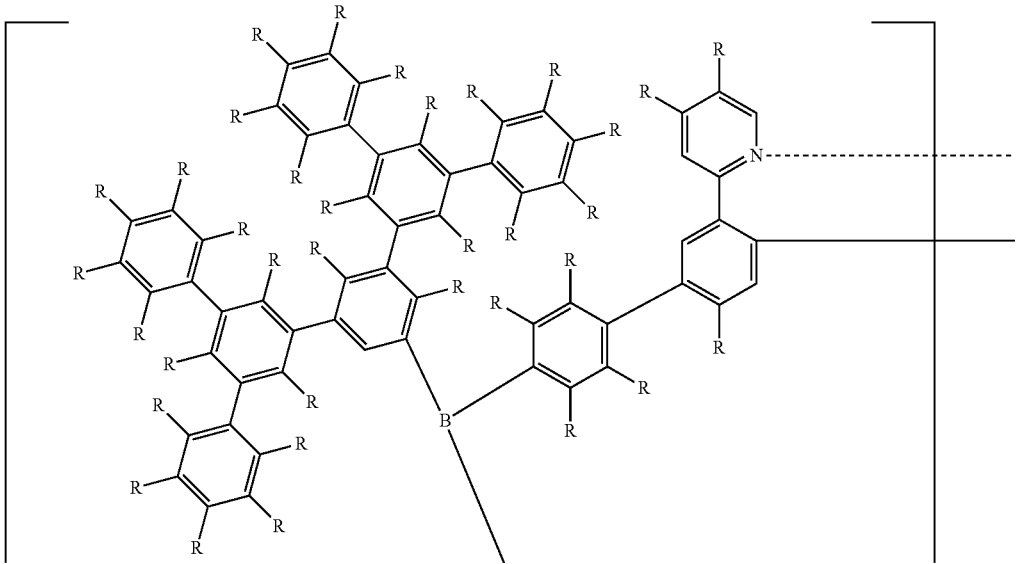
(L1-011)
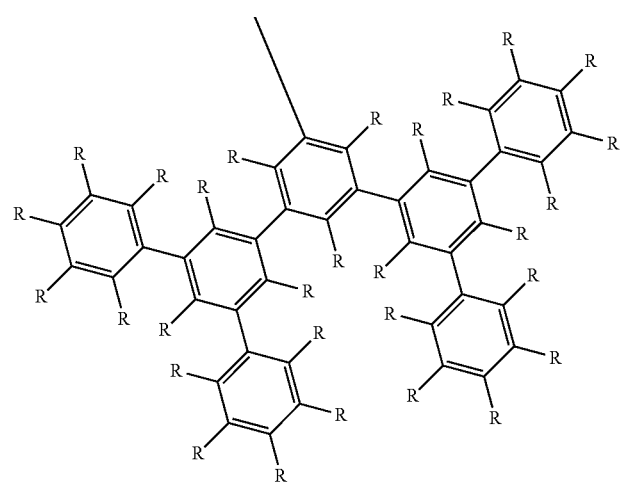

[Chemical formula 30]
(L1-012)
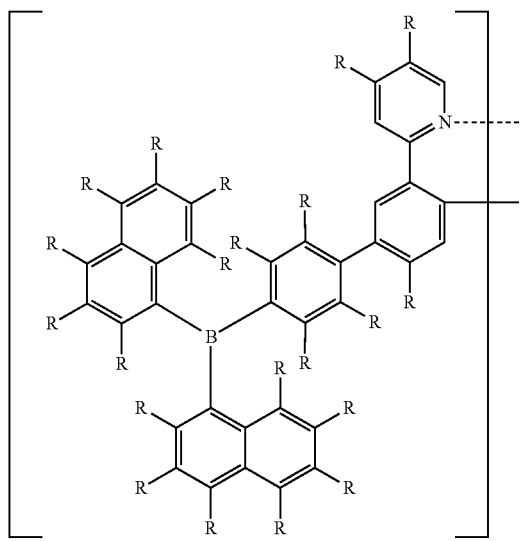
(L1-013)
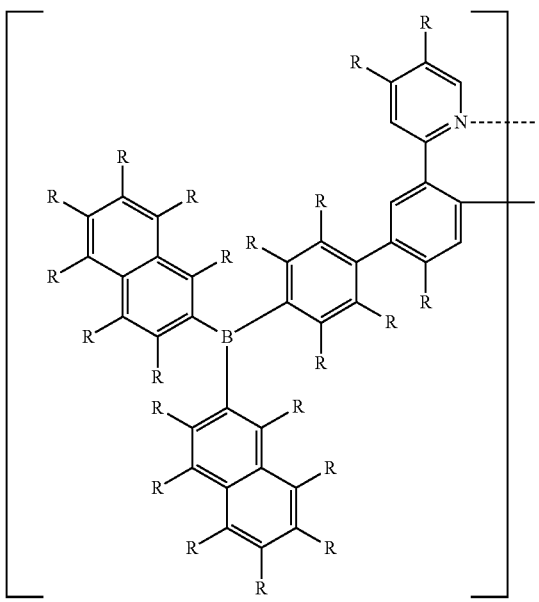
(L1-014)
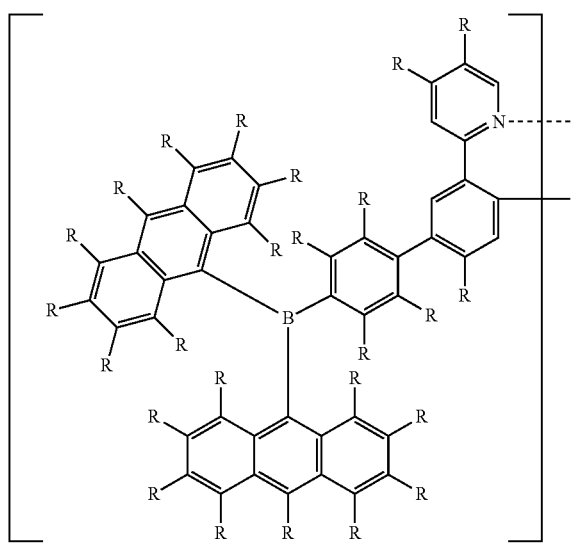

[Chemical formula 31]
(L1-015)
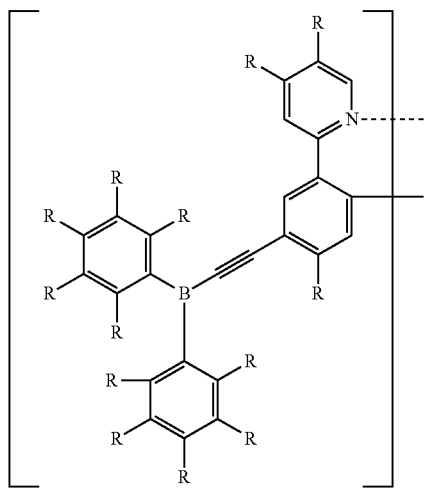
(L1-016)
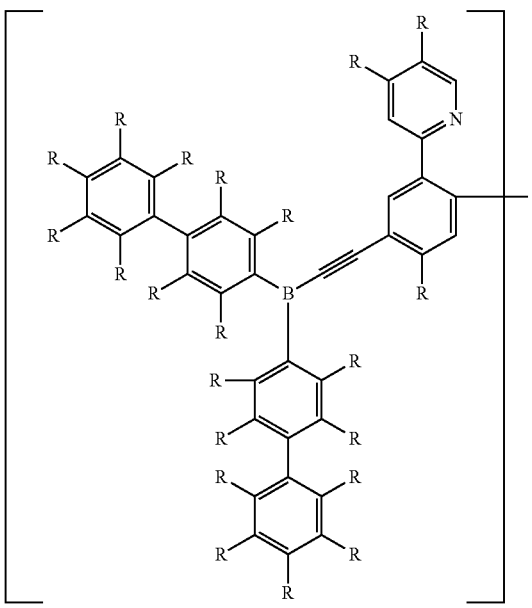
(L1-017)
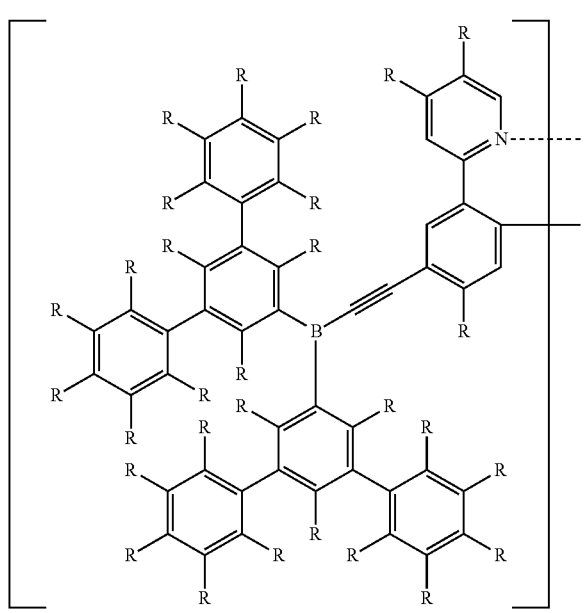

[Chemcial formula 32]
(L1-018)
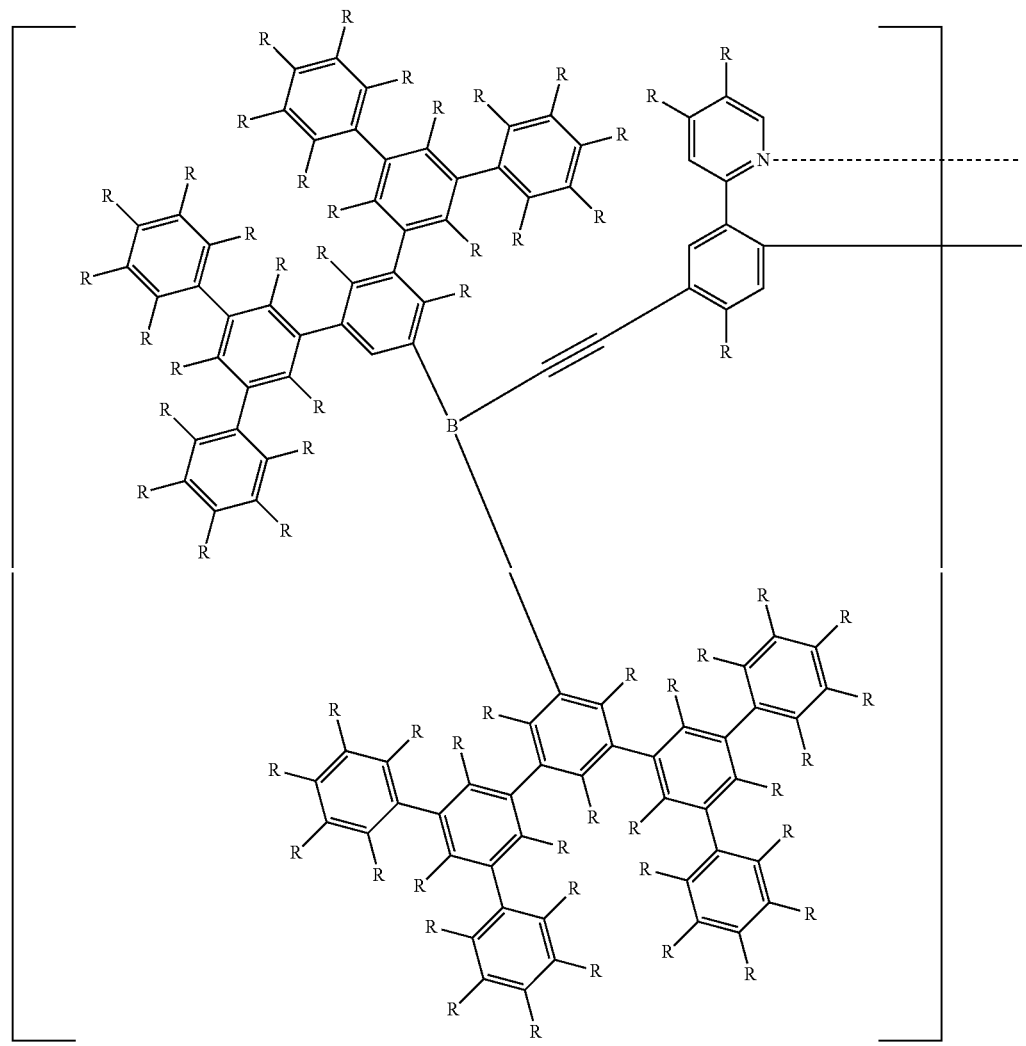
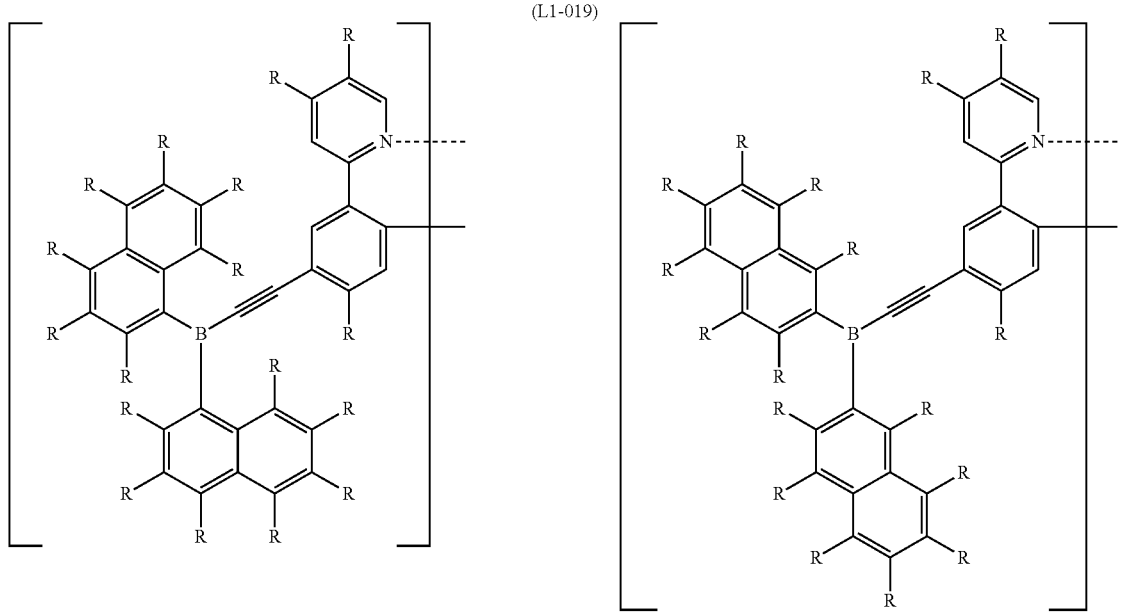

-continued
[Chemical formula 33]
(L1-021)
(L1-022)
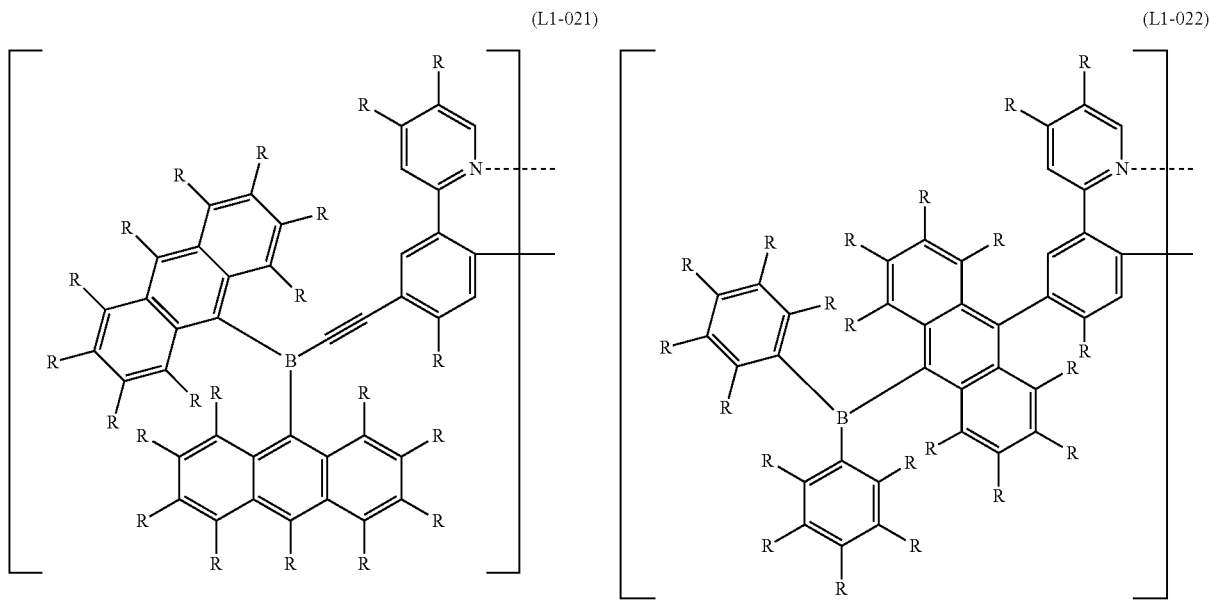
(L1-022)
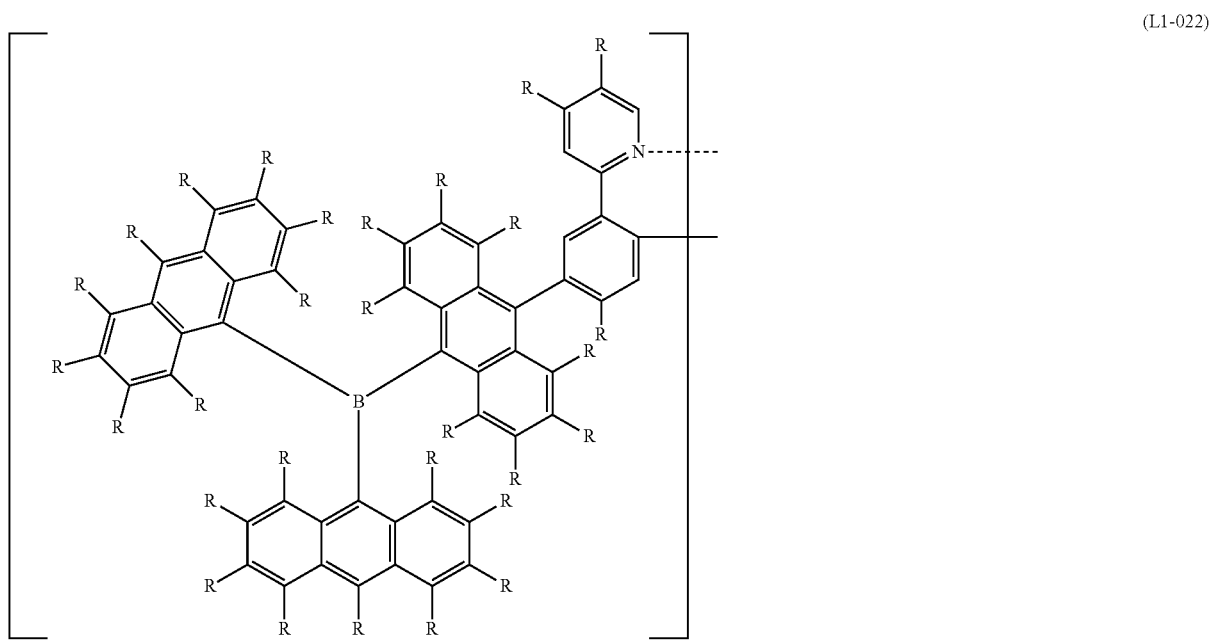

[Chemical formula 34]
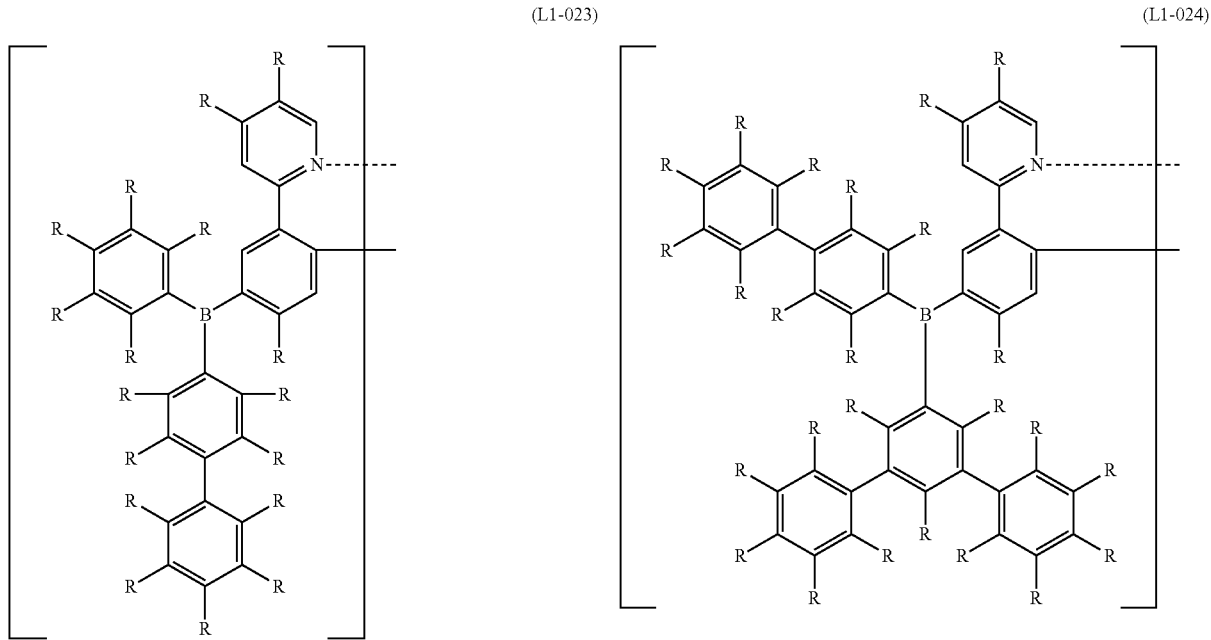
(L1-023) (L1-024)
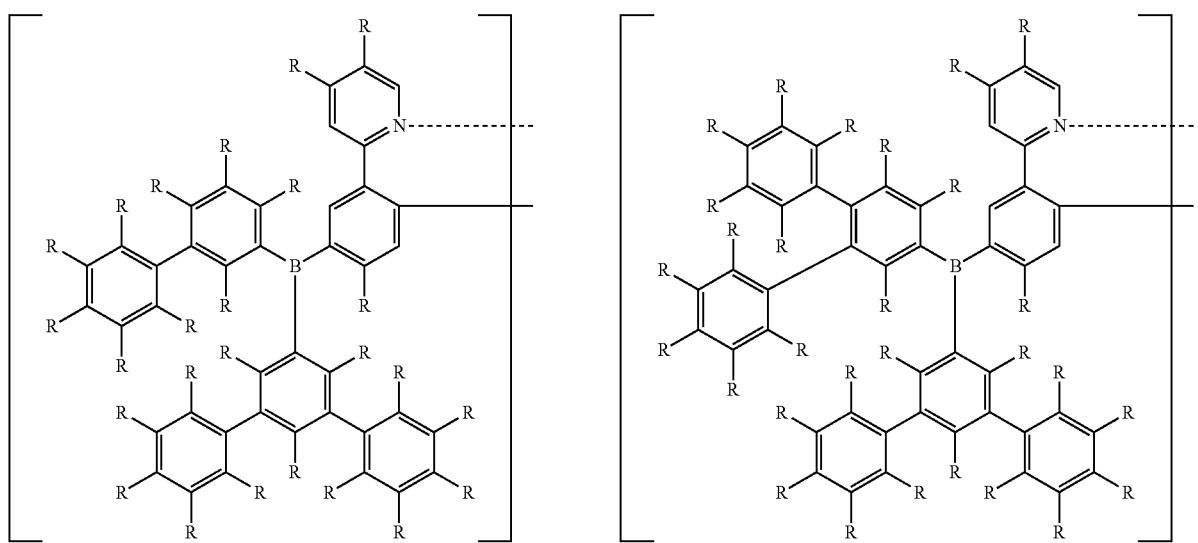
(L1-025) (L1-026)

-continued
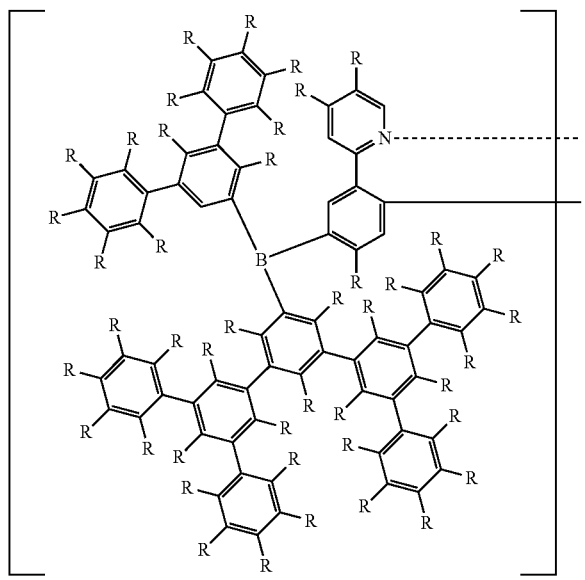
(L1-027)
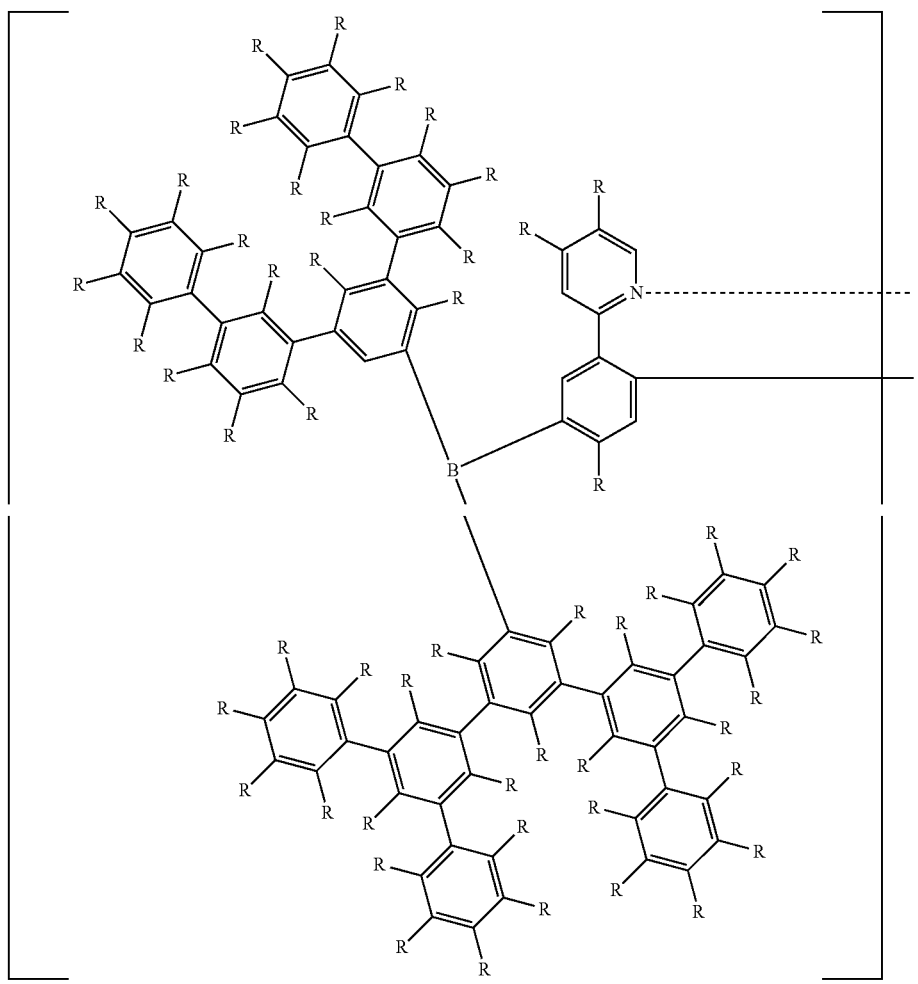
(L1-028)

(L1-029)
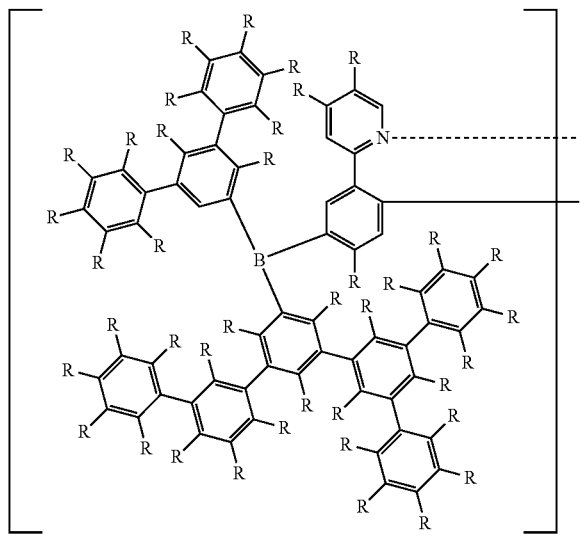
[Chemical formula 36]
(L1-030)
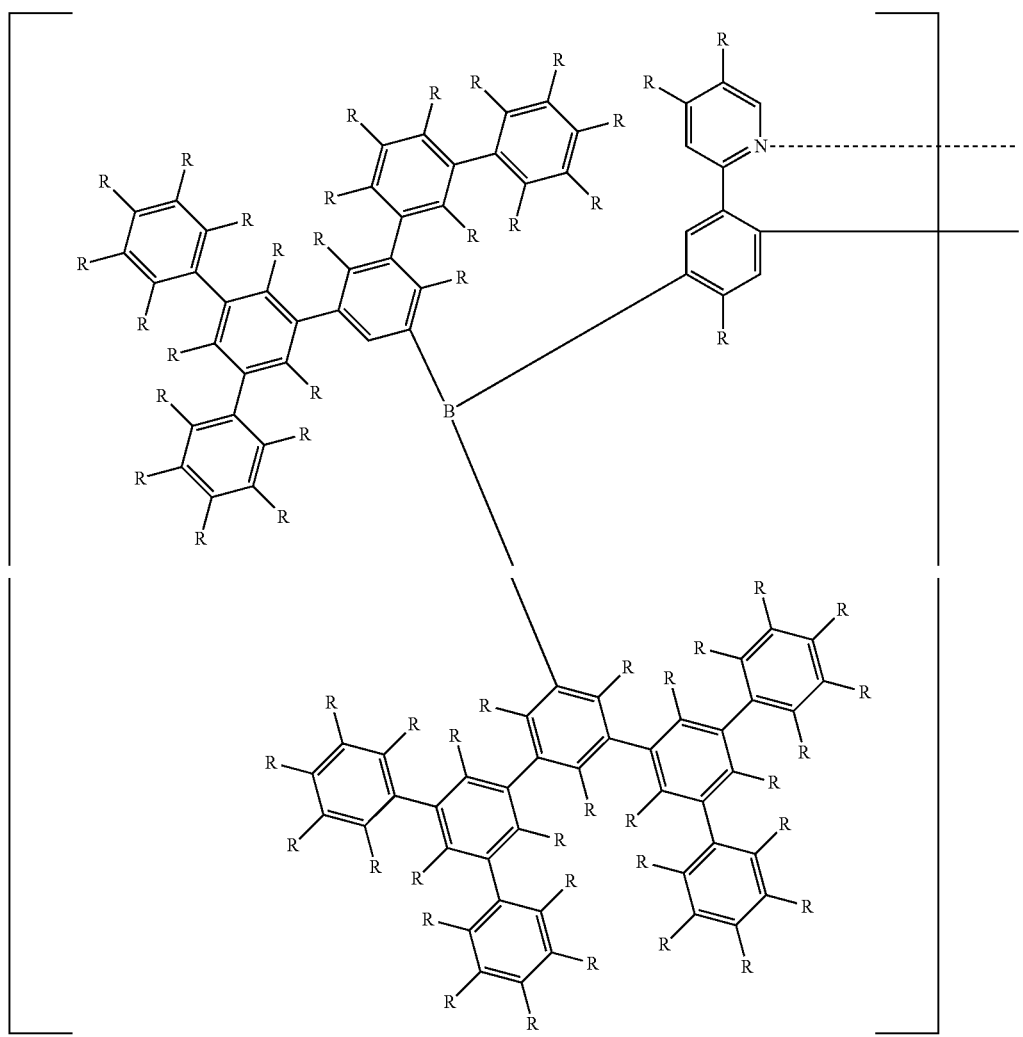

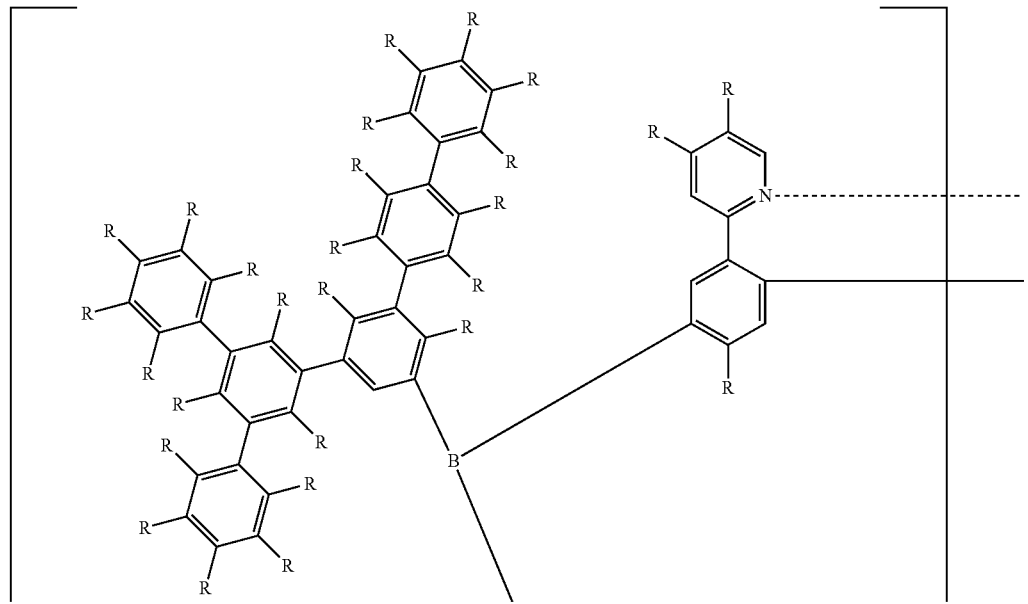
(L1-031)
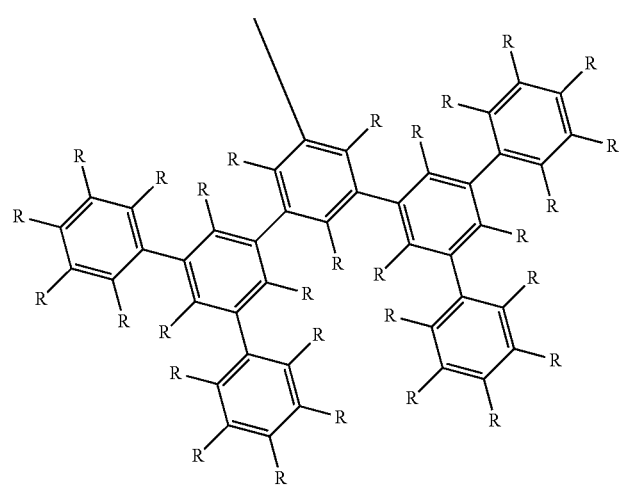

(L1-032)
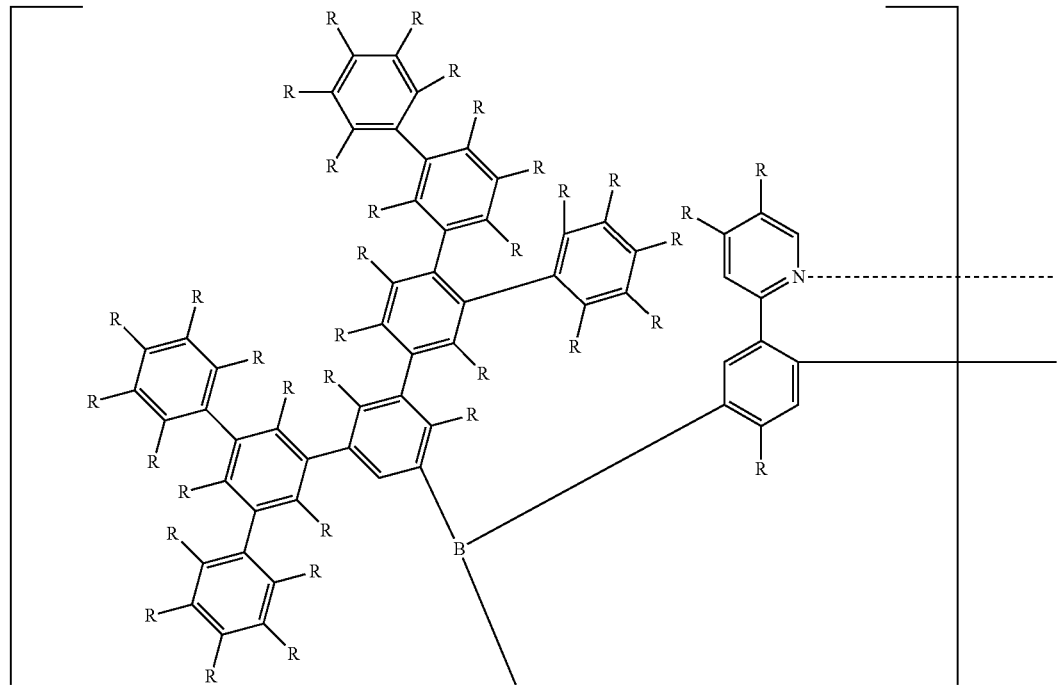
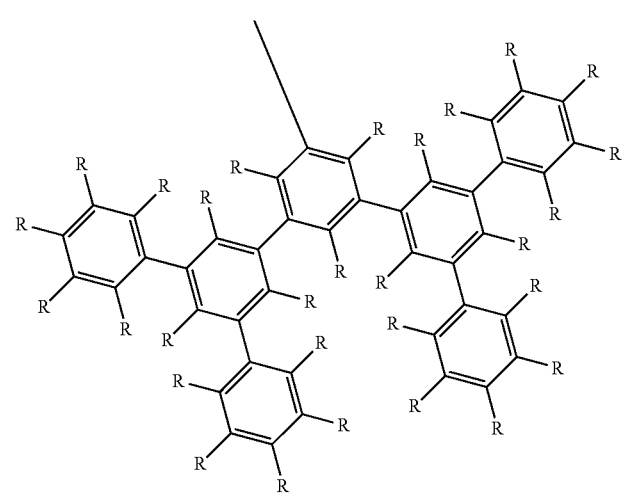

[Chemical formula 37]
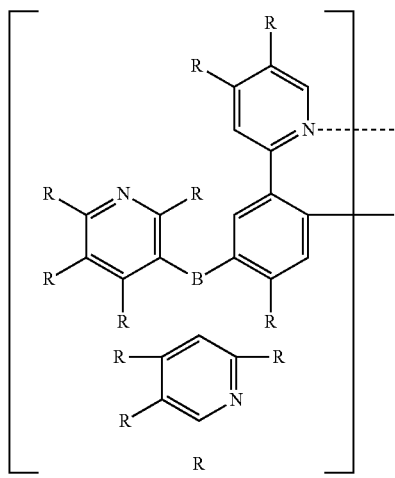 (L1-033)
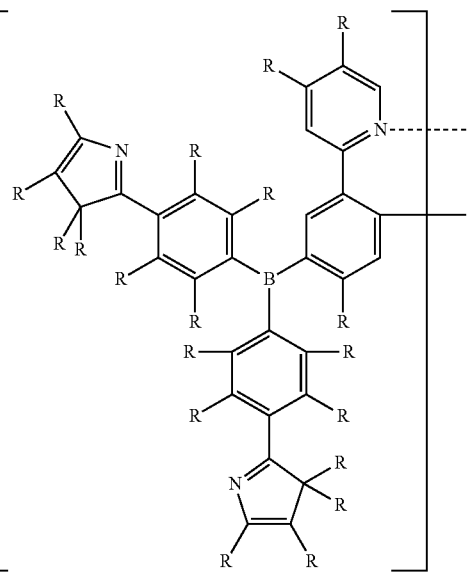 (L1-034)
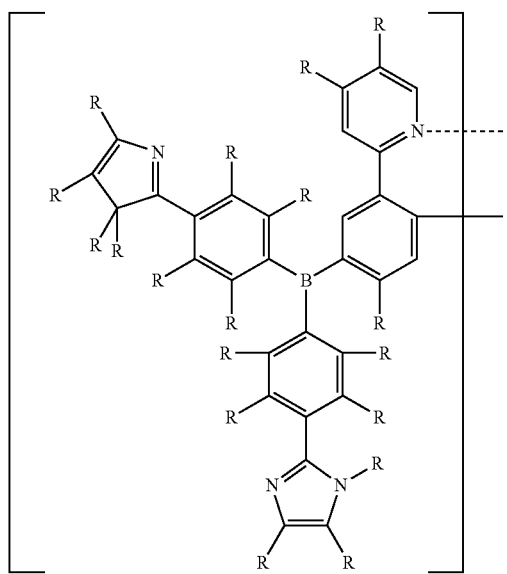 (L1-035)
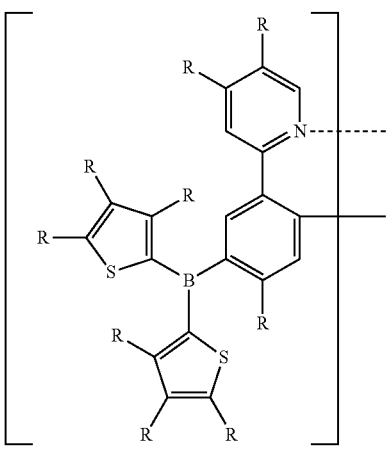 (L1-036)

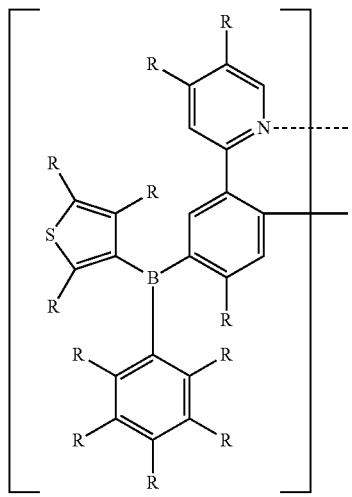

(L1-037)

In the formulae (L1-001) to (L1-037), R is as defined above.

One preferred structure of the group represented by the formula (L1) is a group represented by the formula (L1-1) below.

[Chemical formula 38]

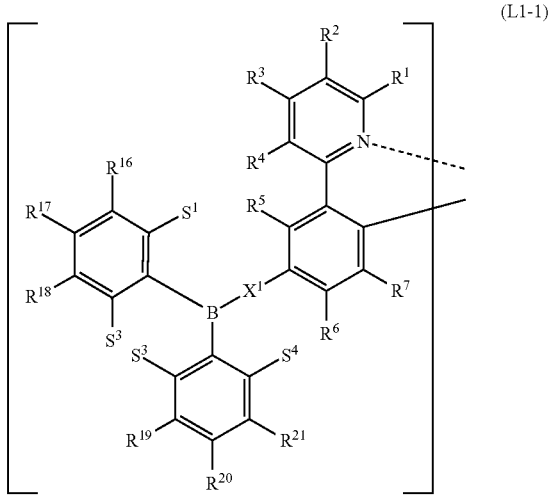

(L1-1)

In the formula (L1-1), $R^1$, $R^2$, $R^3$, $R^4$, $R^5$, $R^6$, $R^7$, and $X^1$ are as defined above. $R^{16}$, $R^{17}$, $R^{18}$, $R^{19}$, $R^{20}$, and $R^{21}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group. These groups may optionally have a substituent.

In the formula (L1-1), $S^1$, $S^2$, $S^3$, and $S^4$ each independently represent an alkyl group, an alkoxy group, an aryl group, an aralkyl group, a substituted amino group, or a monovalent aromatic heterocyclic group. These groups may optionally have a substituent.

In the formula (L1-1), Preferred examples of the $R^1$, $R^2$, $R^3$, $R^4$, $R^5$, $R^6$, $R^7$, and $X^1$ are the same as the preferred examples of the $R^1$, $R^2$, $R^3$, $R^4$, $R^5$, $R^6$, $R^7$, and $X^1$ defined for the formula (L1).

In the formula (L1-1), preferably, $R^{16}$, $R^{17}$, $R^{18}$, $R^{19}$, $R^{20}$, and $R^{21}$ are each independently a hydrogen atom, an alkyl group, or an aryl group optionally having a substituent, in terms of the light-emitting characteristics of a device to be formed.

In the formula (L1-1), at least one group selected from among $R^{16}$, $R^{17}$, $R^{18}$, $R^{19}$, $R^{20}$ and $R^{21}$ is preferably an alkyl group, a substituted amino group, or an aryl group having, as a substituent, a group selected from among the group consisting of alkyl groups, aryl groups, substituted amino groups, and alkoxy groups, more preferably an alkyl group or an aryl group having, as a substituent, a group selected from among the group consisting of alkyl groups, alkoxy groups, and aryl groups, and still more preferably an alkyl group or an aryl group having an aryl group as a substituent, in terms of the solubility of the metal complex in a solvent. Particularly preferably, in the formula (L1-1), $R^{17}$ and $R^{21}$ are each independently a hydrogen atom or an alkyl group, and $R^{16}$, $R^{18}$, $R^{19}$, and $R^{21}$ are each independently an alkyl group or a phenyl group having, as a substituent, a phenyl group substituted with an alkyl group. In addition, a substituent of the boron atom in the formula (L1-1) is particularly preferably a phenyl group having an alkyl group as a substituent and having an aromatic dendrimer structure. Examples of the phenyl group having an alkyl group as a substituent and having an aromatic dendrimer structure include a 1,1':3',1"-terphenyl-5-yl group having an alkyl group as a substituent and a 5',5'''-diphenyl-[1,1':3',1":3",1''':3''',1''''-quinquephenyl]-5-yl group having an alkyl group as a substituent.

In the formula (L1-1), preferably, among $R^{16}$, $R^{17}$, $R^{18}$, $R^{19}$, $R^{20}$, and $R^{21}$, $R^{16}$, $R^{18}$, $R^{19}$ and $R^{21}$ are each a hydrogen atom, and $R^{17}$ and $R^{20}$ are each an alkyl group, in terms of the easy synthesis of the metal complex. In addition, when n in the formula (1) represents 3, $R^{17}$ and $R^{20}$ are each preferably an alkyl group having two or more carbon atoms, in consideration of the solubility of the metal complex in a solvent.

In the formula (L1-1), $S^1$, $S^2$, $S^3$, and $S^4$ are each preferably an alkyl group or an aryl group and more preferably an alkyl group, in terms of the light-emitting characteristics of a device to be formed.

Examples of the group represented by the formula (L1-1) include groups represented by the formulae (L1-1-001) to (L1-1-019) below. In terms of the light-emitting characteristics of a device to be formed, the formula (L1-1) is preferably (L1-1-001) to (L1-1-004), (L1-1-010) to (L1-1-014), and (L1-1-016), more preferably (L1-1-001), (L1-1-003), (L1-1-004), (L1-1-010), (L1-1-011), and (L1-1-016), and still more preferably (L1-1-001), (L1-1-003), and (L1-1-004).
[Chemical formula 39]
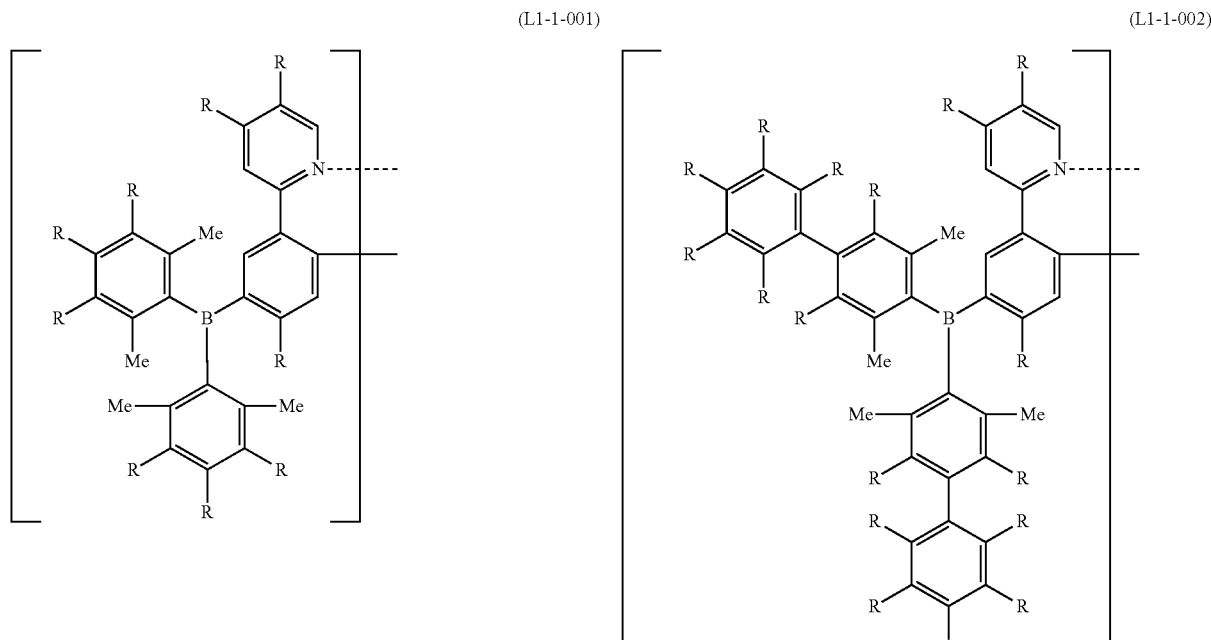
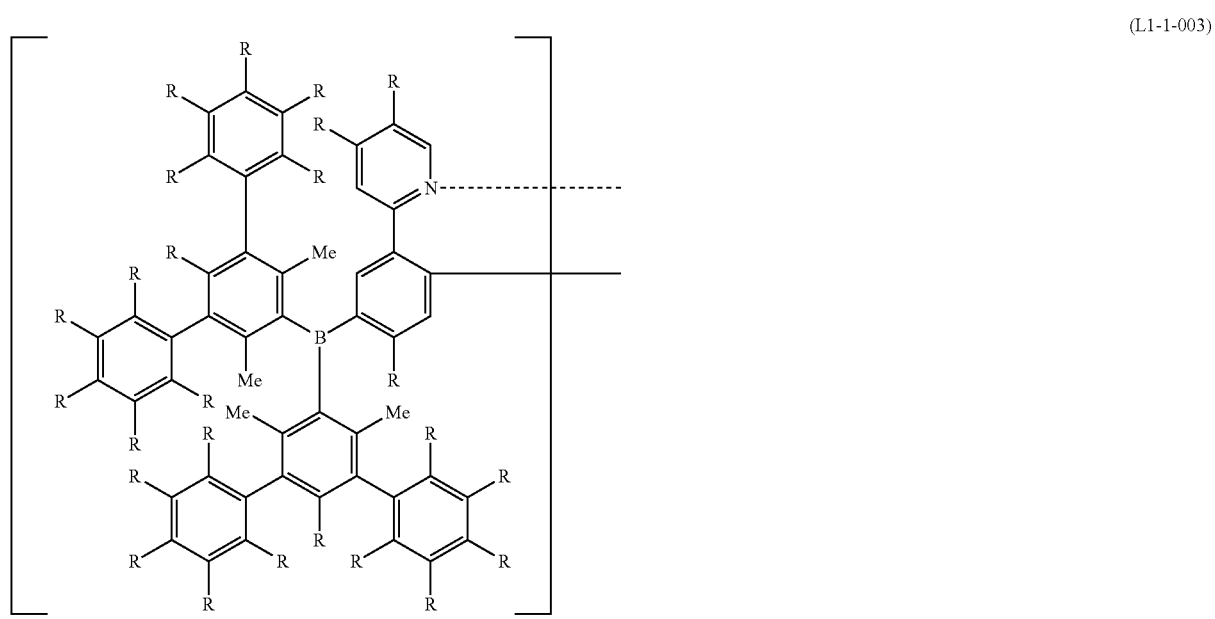

-continued
(L1-1-004)
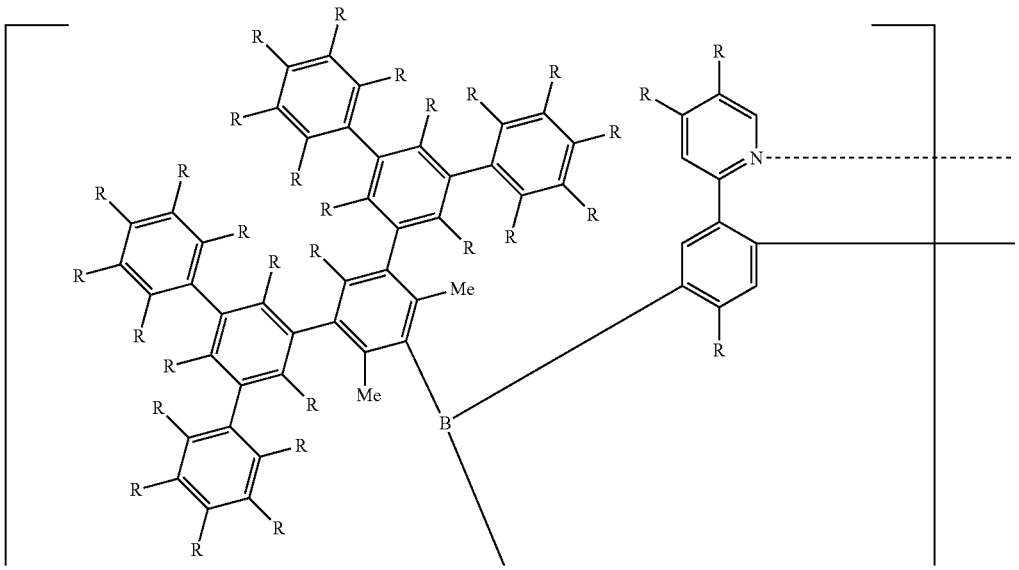
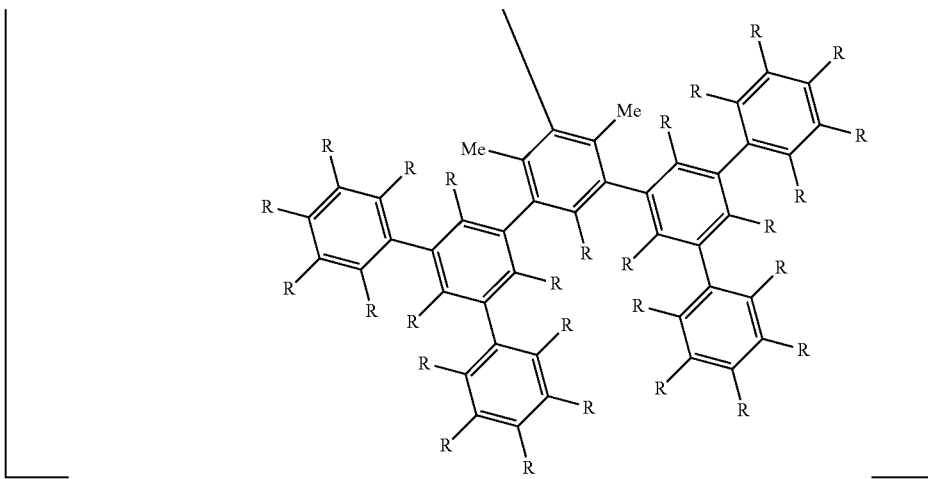

-continued
[Chemical formula 40]
(L1-1-005)
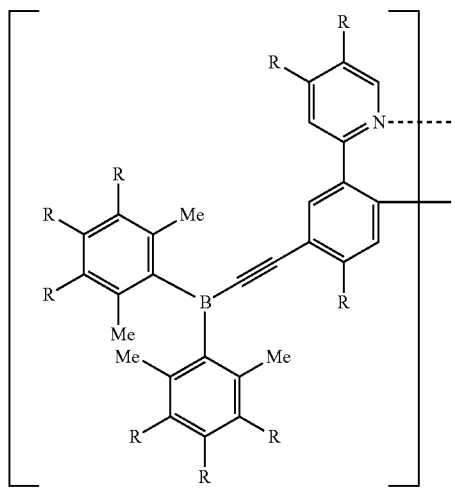
(L1-1-006)
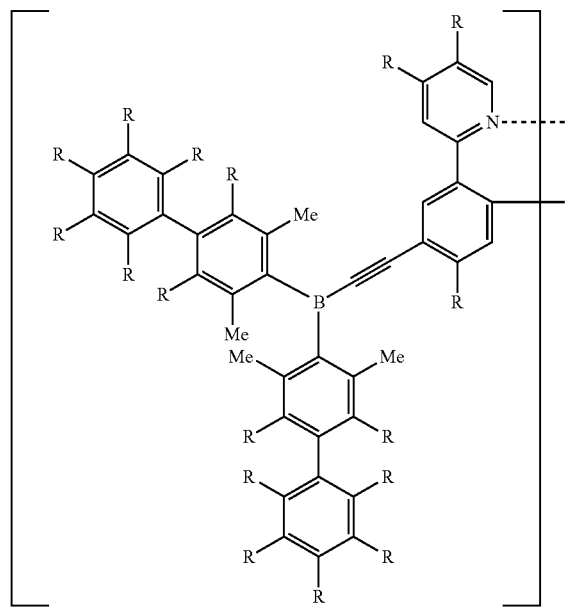
(L1-1-007)
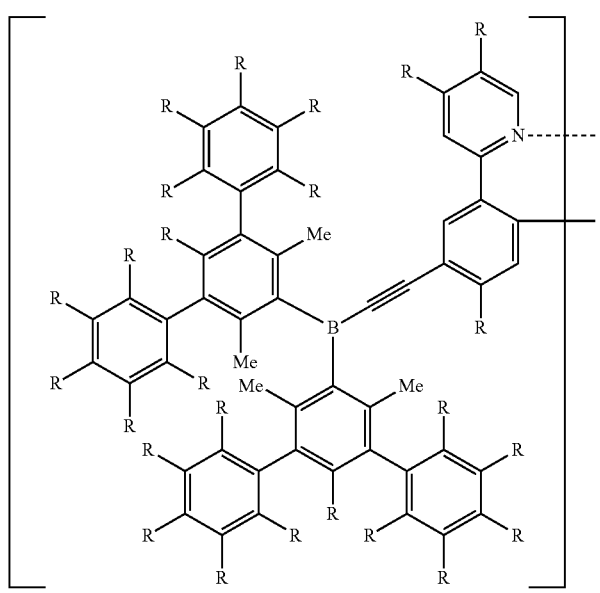

-continued
[Chemical formula 41]
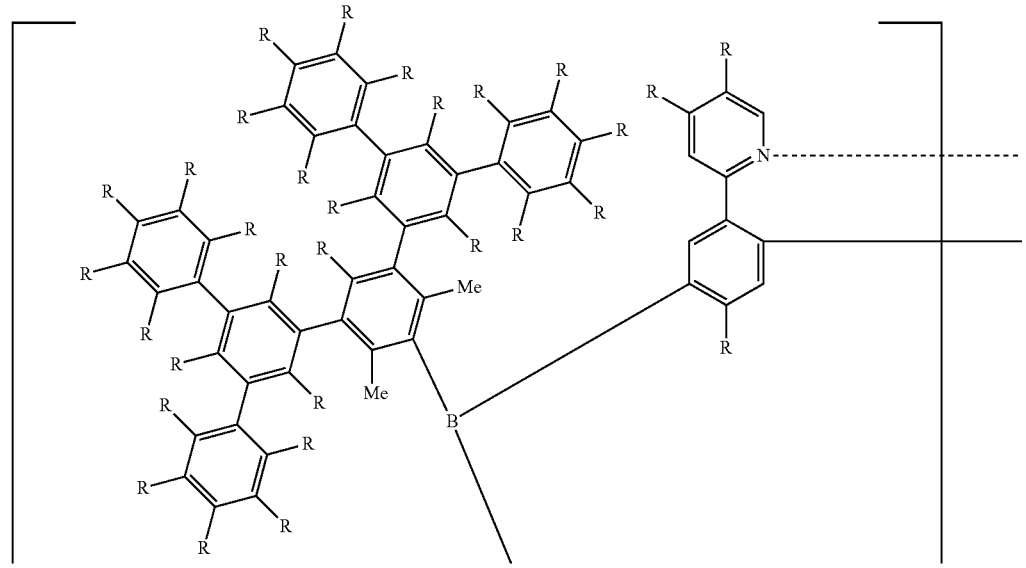
(L1-1-008)
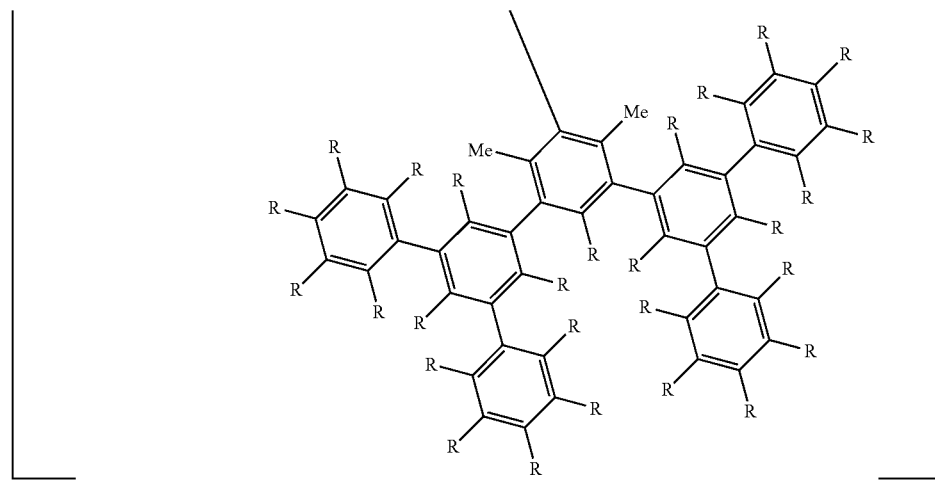
(L1-1-009)
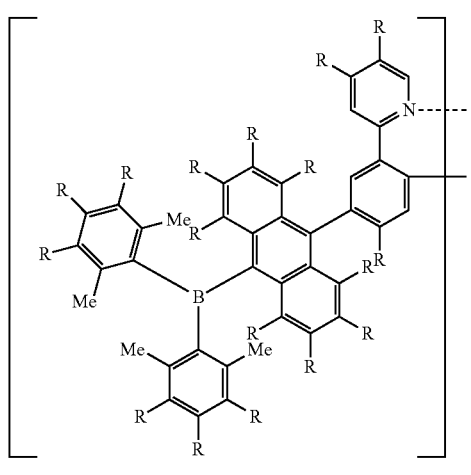
(L1-1-009)
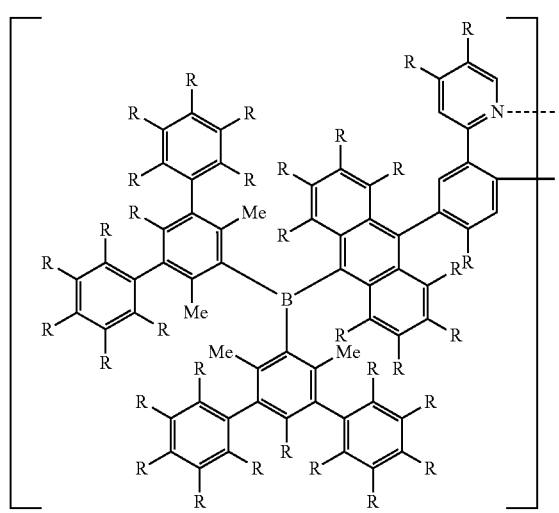

[Chemical formula 42]
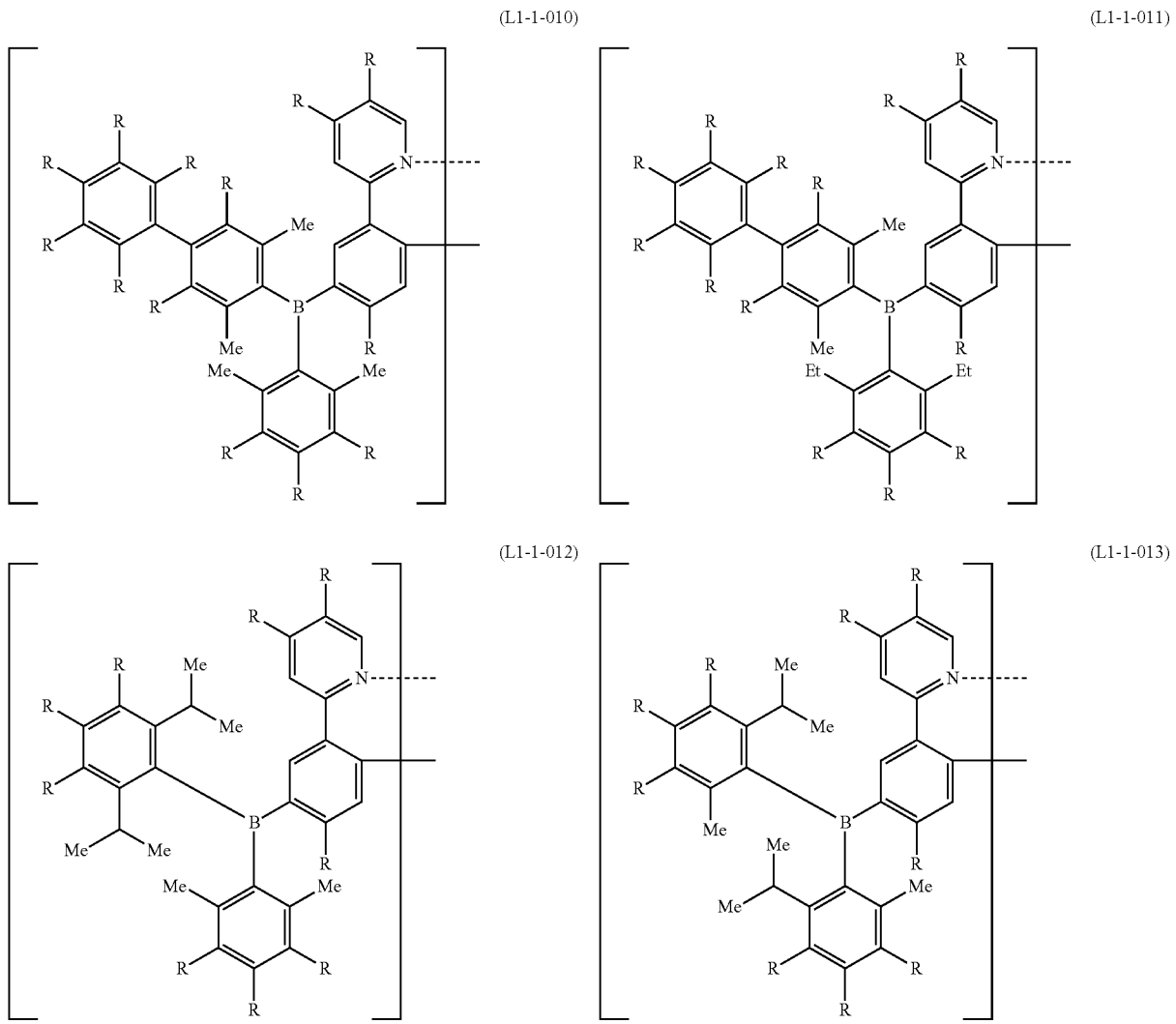
[Chemical formula 43]
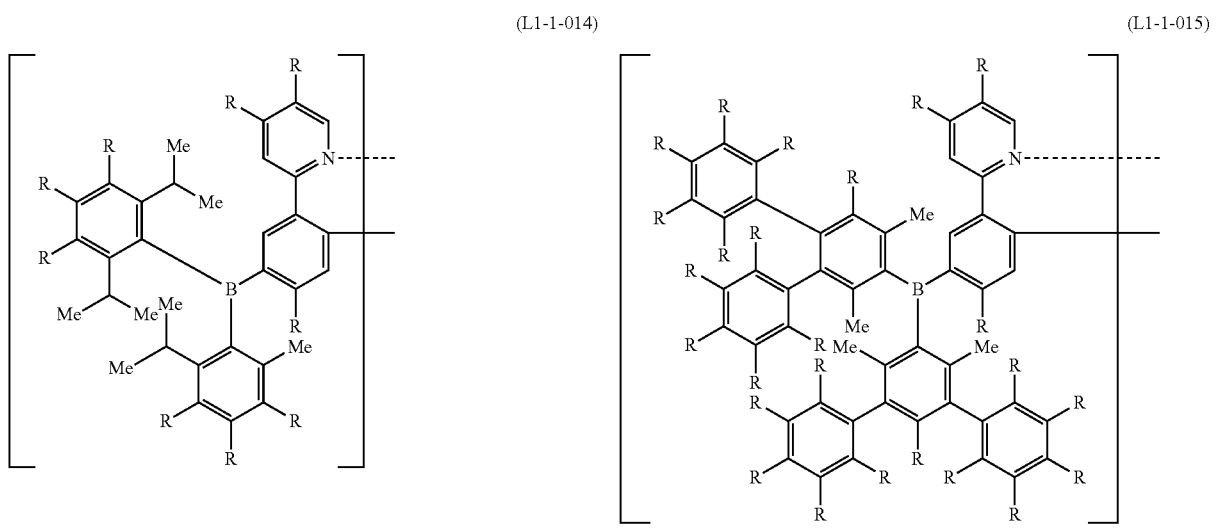

(L1-1-016)
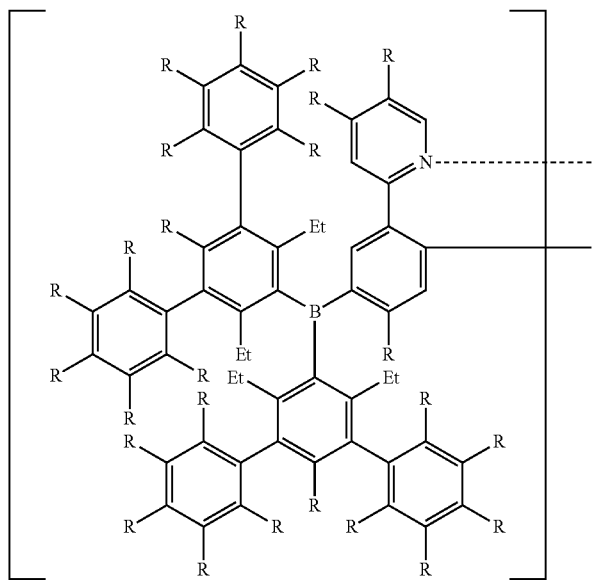
[Chemical formula 44]
(L1-1-017)
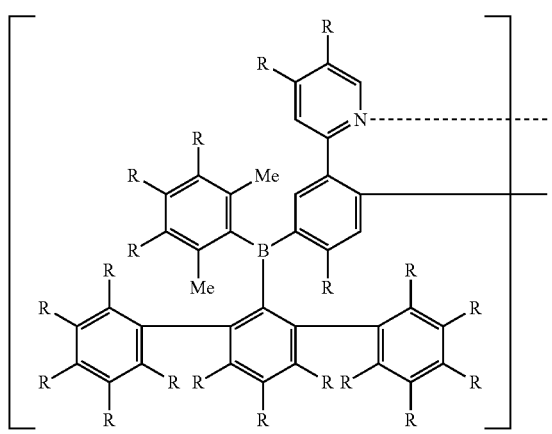
(L1-1-018)
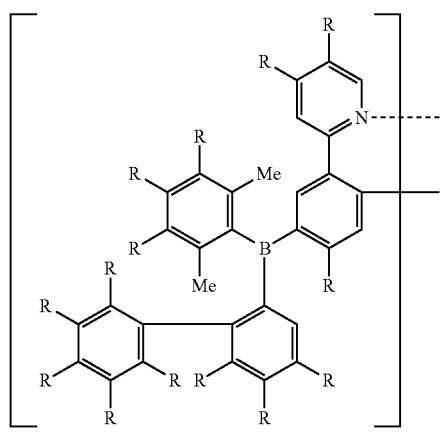
(L1-1-019)
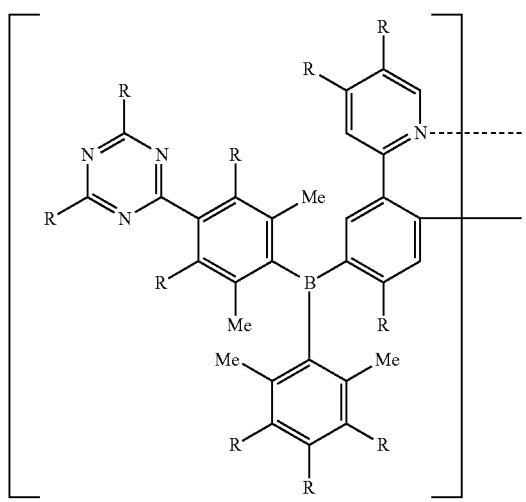

In the formulae (L1-1-001) to (L1-1-019), R is as defined above.

In the formula (1), the group represented by the formula (1-2) below:

[Chemical formula 45]

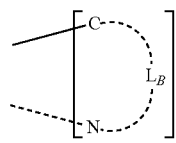

(1-2)

is different from the group represented by the formula (1-1) and means a group represented by the formula (L2) below.

[Chemical formula 46]

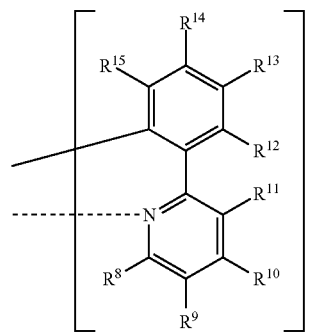

(L2)

In the formula (L2), $R^8$, $R^9$, $R^{10}$, $R^{11}$, $R^{12}$, $R^{13}$, $R^{14}$, and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxy group, an alkenyl group, an alkynyl group, a halogen atom, or a cyano group.

Two of the groups represented by $R^8$, $R^9$, $R^{10}$, $R^{11}$, $R^{12}$, $R^{13}$, $R^{14}$, and $R^{15}$ may be bonded directly to each other or bonded via a group represented by —O—, a group represented by —S—, a group represented by —C(=O)—, a group represented by —C(=O)—O—, a group represented by —N($R^A$)—, a group represented by —C(=O)—N($R^A$)—, or a group represented by —C($R^A$)$_2$— to thereby form a five-membered ring, a six-membered ring, or a seven-membered ring. Here, $R^A$ represents an alkyl group, an aryl group, or a monovalent aromatic heterocyclic group.

In the formula (L2), $R^8$, $R^9$, $R^{10}$, $R^{11}$, $R^{12}$, $R^{13}$, $R^{14}$, and $R^{15}$ are each preferably a hydrogen atom, an alkyl group, an aryl group, or a monovalent aromatic heterocyclic group, in terms of the light-emitting characteristics of a device to be formed.

In the formula (L2), $R^8$, $R^9$, $R^{10}$, $R^{11}$, $R^{12}$, $R^{13}$, $R^{14}$, and $R^{15}$ are each preferably a hydrogen atom, an alkyl group, or an aryl group in terms of the solubility of the metal complex, and at least one of them is preferably an alkyl group or an aryl group, more preferably a hydrogen atom, an alkyl group, or an aryl group, and more preferably an aryl group. More preferably, the aryl group is a phenyl group having an alkyl group as a substituent and having an aromatic dendrimer structure. Examples of the phenyl group having an alkyl group as a substituent and having an aromatic dendrimer structure include a 1,1':3',1"-terphenyl-5-yl group having an alkyl group as a substituent and a 5',5'"-diphenyl-[1,1':3',1":3",1"':3"',1""-quinquephenyl]-5-yl group having an alkyl group as a substituent.

Examples of the group represented by the formula (L2) include groups represented by the formulae L2-001 to L2-009 below.

[Chemical formula 47]

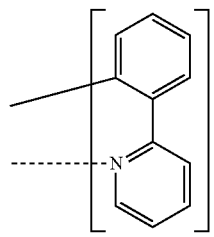

L2-001

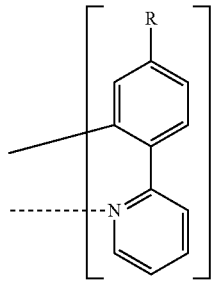

L2-002

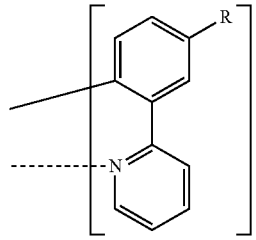

L2-003

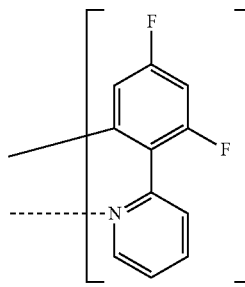

L2-004

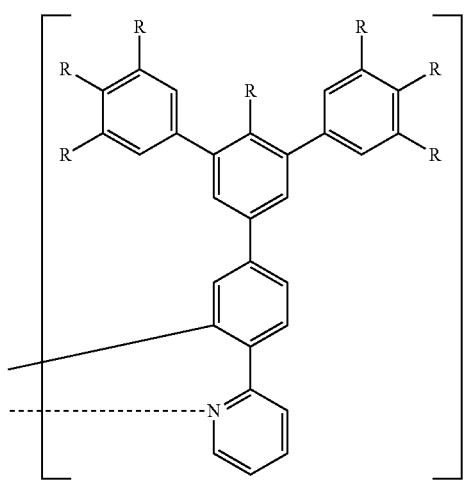

L2-005

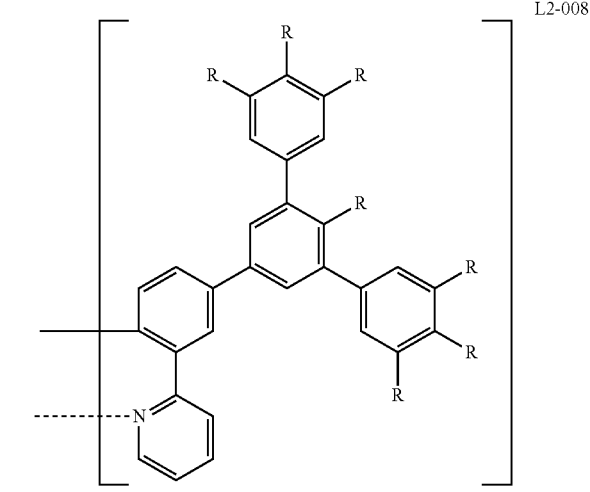

L2-008

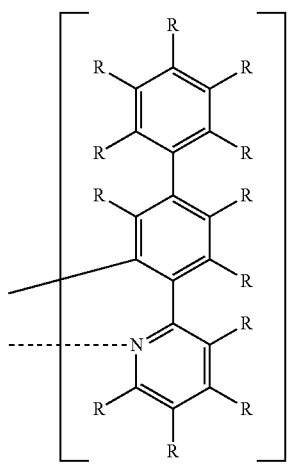

L2-006

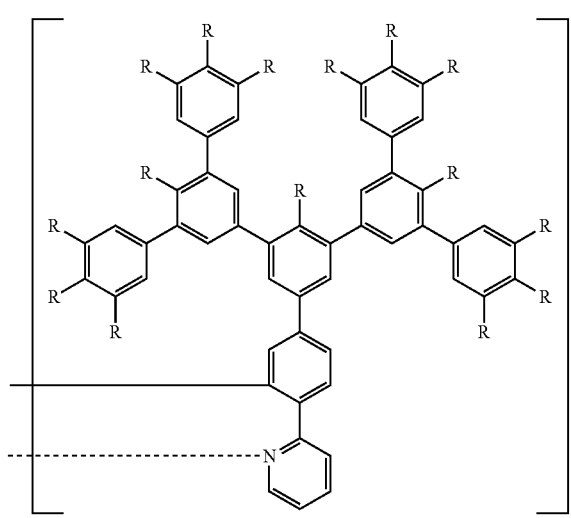

L2-007

L2-009

In the formulae L2-001 to L2-009, R is as defined above.

When there are two or three groups represented by the formula (1-1), the two or three groups represented by the formula (1-1) may be the same as or different from each other. When there are two groups represented by the formula (1-2), the two groups represented by the formula (1-2) may be the same as or different from each other. In terms of the solubility of the metal complex in a solvent, the group represented by the formula (L2) is preferably a group having, as a substituent, an aromatic dendrimer structure and represented by the formula L2-005, formula L2-007, formula L2-008, or formula L2-009. Particularly, the groups represented by the formulae L2-008 and L2-009 are more preferred, and a group in which at least one of a plurality of Rs is an alkyl group is still more preferred.

However, when n is 3 and all the groups represented by the formula (L1) have the same structure, namely, in the case of a metal complex represented by the formula (1-3) below, it is not preferable to use this metal complex only as the present invention or use a composition consisting of this metal complex and a solvent as the present invention.

[Chemical formula 48]

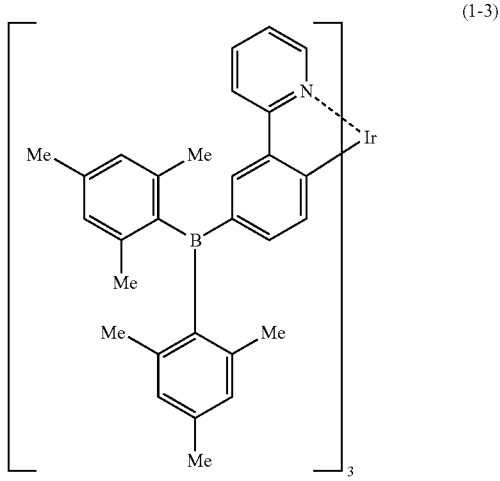

(1-3)

The metal complex represented by the formula (1) may have a plurality of geometrical isomers. The metal complex represented by the formula (1) may be any of these geometrical isomers and is preferably a facial isomer because a device to be formed may have good light-emitting characteristics.

<Method for Preparing Metal Complex>

The metal complex of the present invention may be prepared by any method. For example, the metal complex can be prepared by a method in which a ligand, a compound, and an iridium compound are reacted in a solvent. In this method, a base and a silver salt compound may be present in the reaction system.

Examples of the above method include methods described in: J. Am. Chem. Soc. 1984, 106, 6647; Inorg. Chem. 1991, 30, 1685; Inorg. Chem. 1994, 33, 545; Inorg. Chem. 2001, 40, 1704; and Chem. Lett., 2003, 32, 252.

The reaction temperature in the reaction in the above method may be generally set to a temperature between the melting point of a solvent present in the reaction system under normal pressure and its boiling point under normal pressure. Preferably, the reaction temperature is set to a temperature between −90° C. and the boiling point of the solvent under normal pressure. When a sealed reaction vessel is used in the above method, for example, when a microwave reaction apparatus is used, the reaction can be performed at a temperature equal to or higher than the boiling point of the solvent.

The reaction time in the above reaction is generally 30 minutes to 150 hours. When a microwave reaction apparatus is used for the reaction, the reaction time is generally several minutes to several hours.

A compound serving as the ligand can be synthesized by a coupling reaction such as Suzuki coupling, Grignard coupling, Stille coupling or the like of a 2-phenylpyridine derivative and an aromatic heterocyclic compound. For example, the compound serving as the ligand can be synthesized by dissolving the 2-phenylpyridine derivative and the aromatic heterocyclic compound in an organic solvent and reacting them using a base and an appropriate catalyst at a temperature equal to or higher than the melting point of the organic solvent and equal to or lower than its boiling point. This synthesis may be performed with reference to: "Organic Syntheses," Collective Volume VI, pp. 407-411, John Wiley & Sons, Inc., 1988; Chem. Rev., vol. 106, p. 2651 (2006); Chem. Rev., vol. 102, p. 1359 (2002); Chem. Rev., vol. 95, p. 2457 (1995); and J. Organomet. Chem., vol 576, p. 147 (1999).

The aromatic heterocyclic compound can be synthesized by methods described in: "HOUBEN-WEYL METHODS OF ORGANIC CHEMISTRY 4TH EDITION," vol. E9b, p. 1, GEORG THIEME VERLAG STUTTGART; HOUBEN-WEYL METHODS OF ORGANIC CHEMISTRY 4TH EDITION, vol. E9c, p. 667, GEORG THIEME VERLAG STUTTGART; and the like.

The catalyst used in the coupling reaction is preferably a palladium catalyst.

Examples of the palladium catalyst include palladium acetate, bis(triphenylphosphine)palladium(II) dichloride, tetrakis(triphenylphosphine)palladium(0), [1,1'-bis(diphenylphosphino)ferrocene]dichloropalladium(II), and tris(dibenzylideneacetone)dipalladium(0). The palladium catalyst is preferably tetrakis(triphenylphosphine)palladium(0), [1,1'-bis(diphenylphosphino)ferrocene]dichloropalladium(II), or tris(dibenzylideneacetone)dipalladium(0).

The palladium catalyst may be used in combination with a phosphorus compound such as triphenylphosphine, tri(o-tolyl)phosphine, tri(tert-butyl)phosphine, tricyclohexylphosphine, or 1,1'-bis(diphenylphosphino)ferrocene.

Examples of the compound serving as the ligand include compounds serving as bidentate ligands represented by the formulae (L1) and (L2). Namely, examples of the compound serving as the ligand include compounds represented by the formulae (L1-H) and (L2-H) below.

[Chemical formula 49]

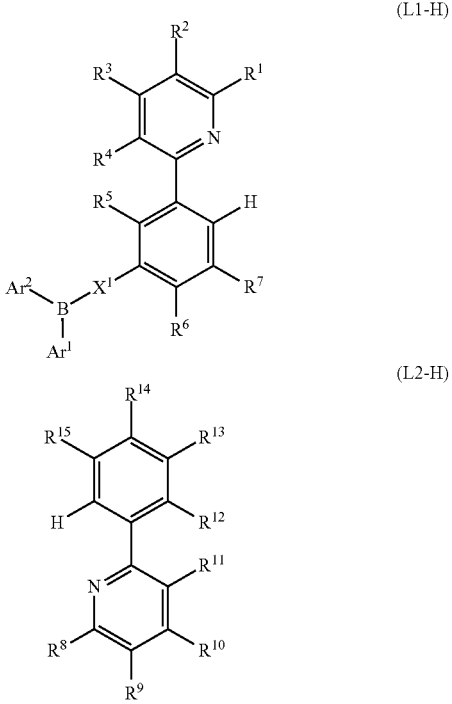

In the formulae (L1-H) and (L2-H), groups represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $X^1$, $Ar^1$, and $Ar^2$ are the same as the groups represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $X^1$, $Ar^1$, and $Ar^2$ defined for the formulae (L1) and (L2).

In the compound serving as the bidentate ligand represented by the formula (L1-H), when $Ar^1$ and $Ar^2$ are the same, the compound can be synthesized according to the following scheme.

[Chemical formula 50]

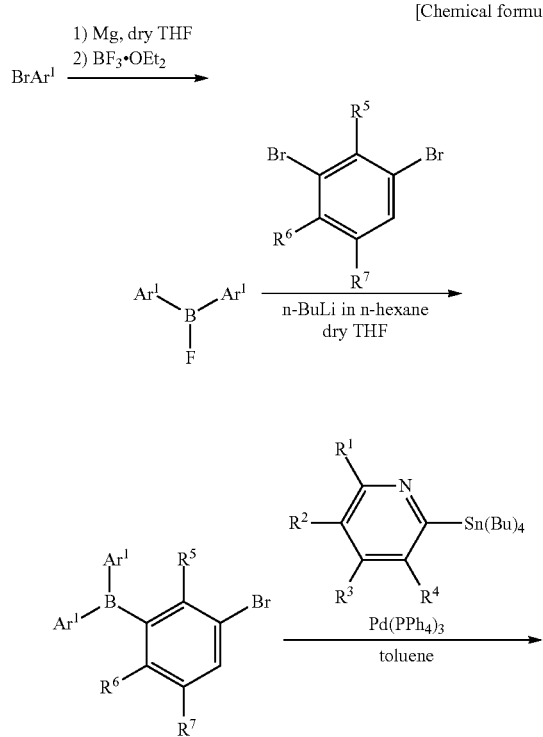

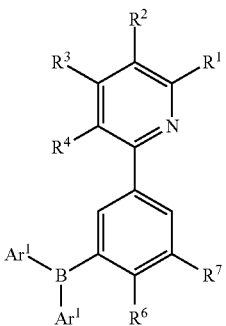

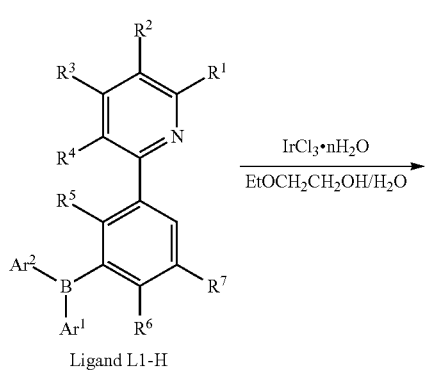

Ligand L1-H

An example of the method for preparing the metal complex of the present invention will be specifically described.

In the metal complex represented by the formula (1), when n is 2, this metal complex can be prepared as follows. For example, iridium chloride(III) n-hydrate and a ligand represented by the formula (L1-H) in an amount of at least 2 equivalents with respect to the iridium chloride(III) n-hydrate are heated and stirred in a solvent mixture of 2-ethoxyethanol and water under inert gas atmosphere, whereby binuclear complex DM-L1 can be prepared. Then the ligand represented by the formula (L2-H) is further added in an amount of 6 equivalents. The mixture is heated in 2-ethoxyethanol under inert gas atmosphere in the presence of silver(I) trifluoromethanesulfonate, whereby metal complex Ir (n=2) or the metal complex represented by the formula (1) above with n being 2 can be prepared.

[Chemical formula 51]

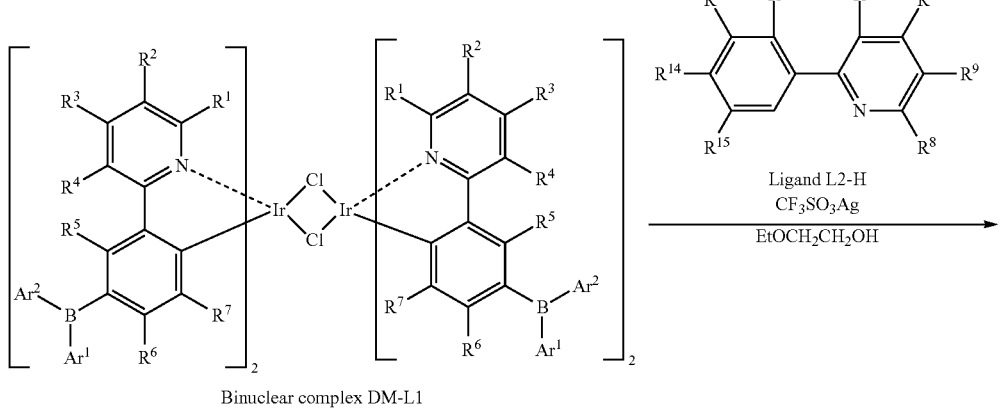

Binuclear complex DM-L1

Ligand L2-H

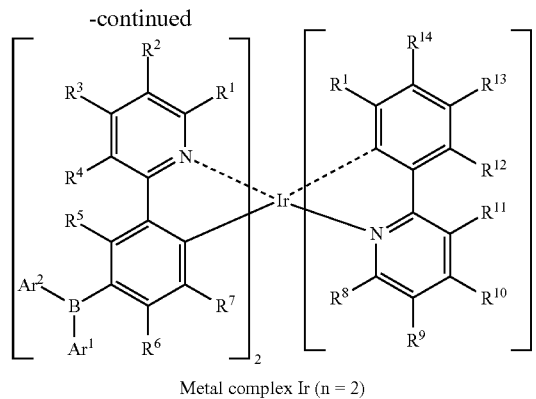

Metal complex Ir (n = 2)

The prepared metal complex of the present invention can be identified and analyzed by elementary analysis, nuclear magnetic resonance (NMR) analysis, mass spectroscopy (MS), infrared absorption (IR) analysis and the like.

<Metal-Containing Polymer Compound>

The metal-containing polymer compound of the present invention is a polymer compound containing, as a structural unit, a group (residue) derived from the metal complex represented by the formula (1).

The group derived from the metal complex represented by the formula (1) and comprised in the metal-containing polymer compound of the present invention as a structural unit is a residue obtained by removing one hydrogen atom from the metal complex represented by the formula (1), a residue obtained by removing two hydrogen atoms from the metal complex represented by the formula (1), or a residue obtained by removing three hydrogen atoms from the metal complex represented by the formula (1).

When the structural unit is a residue obtained by removing three hydrogen atoms from the metal complex represented by the formula (1), the metal-containing polymer compound of the present invention is branched at the position of the structural unit. The residue obtained by removing one hydrogen atom from the metal complex represented by the formula (1) may be a substituent on an arylene group or a bivalent aromatic heterocyclic group contained in the metal-containing polymer compound or may be a terminal group of the metal-containing polymer compound.

The metal-containing polymer compound of the present invention may be a non-conjugated polymer compound or a conjugated polymer compound. The metal-containing polymer compound of the present invention is preferably a conjugated polymer compound and more preferably a conjugated polymer compound having an aromatic ring in its main chain, because high conductivity is achieved. The phrase "the metal-containing polymer compound of the present invention is a conjugated polymer compound" means a metal-containing polymer compound in which the ratio of aromatic rings bonded to the main chain of the metal-containing polymer compound directly, via a vinylene group, via an ethynylene group, or via a group represented by a combination of a vinylene group and an ethynylene group is 50% to 100%, particularly 60% to 100%, and more particularly 70% to 100%.

The metal-containing polymer compound of the present invention is preferably a metal-containing polymer compound having at least one structural unit selected from among the group consisting of bivalent aromatic amine residues, arylene groups, and bivalent heterocyclic groups.

The metal-containing polymer compound is also preferably a metal-containing polymer compound having at least two structural units selected from among the group consisting of bivalent aromatic amine residues, arylene groups, and bivalent heterocyclic groups.

In the metal-containing polymer compound of the present invention, the ratio of the total number of moles of the structural unit derived from the metal complex represented by the formula (1) to the total number of moles of all the structural units is generally 0.0001 to 0.4, preferably 0.001 to 0.3, and more preferably 0.001 to 0.25.

The polystyrene-equivalent number average molecular weight of the metal-containing polymer compound of the present invention is preferably $1\times10^3$ to $1\times10^8$, more preferably $1\times10^3$ to $1\times10^7$, and still more preferably $1\times10^4$ to $1\times10^6$ because long half brightness life can be obtained when the metal-containing polymer compound is used for a light-emitting device.

<Composition>

Only one metal complex or metal-containing polymer compound of the present invention or a combination of two or more thereof may be used, and also composition may contain additional elements. The number of types of additional elements may be one or two or more.

Preferable examples of the additional elements that may be contained in the composition of the present invention in addition to the metal complex and/or metal-containing polymer compound of the present invention include a charge transporting material because it can reduce the driving voltage of a light-emitting device obtained using the composition of the present invention.

Examples of the charge transporting material contained in the composition of the present invention include low-molecular compounds having charge transporting characteristic and polymer compounds having charge transporting characteristic. The charge transporting material contained in the composition of the present invention is preferably a polymer compound having charge transporting characteristic. A well-known material can be used for such a charge transporting material.

Preferably, the polymer compound contained in the composition of the present invention is a charge transporting material and is also a polymer compound having at least one structural unit selected from among the group consisting of bivalent aromatic amine residues, arylene groups, and bivalent heterocyclic groups.

Also preferably, the polymer compound contained in the composition of the present invention is a charge transporting material and is also a polymer compound having at least two structural units selected from among the group consisting of bivalent aromatic amine residues, arylene groups, and bivalent heterocyclic groups.

The number of types of structural units comprised in the polymer compound contained in the composition of the present invention is preferably two or more and more preferably three or more.

The amount of the metal complex and/or the metal-containing polymer compound contained in the composition of the present invention is generally 1 to 60 parts by weight based on 100 parts by weight of the total of the charge transporting material and the metal complex and/or the metal-containing polymer compound. In terms of the light-emitting characteristics of a device to be formed, the amount is preferably 1 to 50 parts by weight and preferably 3 to 50 parts by weight.

The polystyrene-equivalent number average molecular weight of the polymer compound contained in the composition of the present invention is preferably $1 \times 10^3$ to $1 \times 10^8$, more preferably $1 \times 10^3$ to $1 \times 10^7$, and still more preferably $1 \times 10^4$ to $1 \times 10^6$ because long half brightness life can be obtained when the composition is used for a light-emitting device.

Another additional elements that may be contained in the composition of the present invention in addition to the metal complex and/or metal-containing polymer compound of the present invention is preferably a solvent or a dispersion medium because high film forming ability can be obtained.

The number of types of solvents and/or dispersion media that may be contained in the composition of the present invention may be one or two or more in the composition.

Any solvent and dispersion medium may be used so long as solids contained in the metal complex and/or metal-containing polymer compound of the present invention can be dissolved or dispersed therein. Examples of the solvent (and the dispersion medium) include: chlorine solvents (such as chloroform, methylene chloride, 1,2-dichloroethane, 1,1,2-trichloroethane, chlorobenzene, and o-dichlorobenzene); ether solvents (dispersion media) (such as tetrahydrofuran and dioxane); aromatic hydrocarbon solvents (dispersion media) (such as benzene, toluene, and xylene); aliphatic hydrocarbon solvents (dispersion media) (such as cyclohexane, methylcyclohexane, n-pentane, n-hexane, n-heptane, n-octane, n-nonane, and n-decane); ketone solvents (dispersion media) (such as acetone, methyl ethyl ketone, and cyclohexanone); ester solvents (dispersion media) (such as ethyl acetate, butyl acetate, and ethyl cellosolve acetate); polyols and derivatives thereof (such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol); alcohol solvents (dispersion media) (such as methanol, ethanol, propanol, 2-propanol, and cyclohexanol); sulfoxide solvents (dispersion media) (such as dimethyl sulfoxide); and amide solvents (dispersion media) (such as N-methyl-2-pyrrolidone and N,N-dimethylformamide).

When a solvent or dispersion medium is used, no particular limitation is imposed on the amount of the solvent or dispersion medium contained in the composition of the present invention, and the amount may be determined according to the type of the solvent or dispersion medium. For example, when a film is formed using a coating method such as a spin coating method or an inkjet method, the amount of the solvent or dispersion medium contained in the composition of the present invention is preferably 500 to 200000 parts by weight and more preferably 1000 to 100000 parts by weight based on 100 parts by weight of the total of solids other than the solvent or dispersion medium (namely, the metal complex and/or the metal-containing polymer compound and the optional charge transporting material), in terms of film forming ability.

<Device>

The device of the present invention is a device comprising a film containing the above metal complex, the above metal-containing polymer compound, or the above composition and is a device comprising, for example, electrodes comprising an anode and a cathode and a film provided between the electrodes and containing the above metal complex, the above metal-containing polymer compound, or the above composition.

A description will be given of a representative device when the device of the present invention is a light-emitting device.

The device of the present invention is a device comprising a pair of electrodes comprising an anode and a cathode and a film provided between the electrodes and having one layer (a single-layer device) or a plurality of layers (a multilayer device) comprising a light-emitting layer. At least one of the layers constituting the film contains the above metal complex, the above metal-containing polymer compound, or the above composition. The amount of the above metal complex, the above metal-containing polymer compound, or the above composition contained in the film is generally 0.1% by weight to 100% by weight, preferably 0.1% by weight to 80% by weight, and more preferably 0.5% by weight to 60% by weight based on the total of the light-emitting layer. Preferably, the device of the present invention contains, as the material of the light-emitting layer, the above metal complex, the above metal-containing polymer compound, or the above composition.

When the device of the present invention is of the single layer type, the film is the light-emitting layer, and this light-emitting layer contains the above metal complex, the above metal-containing polymer compound, or the above composition.

When the device of the present invention is of the multilayer type, at least one of a hole injection layer, a hole transport layer, the light-emitting layer, an electron transport layer, and an electron injection layer may contain the above metal complex, the above metal-containing polymer compound, or the above composition. Preferably, at least one of the hole transport layer, the light-emitting layer, and the electron transport layer contains the above metal complex, the above metal-containing polymer compound, and the above composition. More preferably, the light-emitting layer contains the above metal complex or the above metal-containing polymer compound.

When the device of the present invention is of the multilayer type, specific examples of the possible layer structure of the film sandwiched between the anode and cathode are as follows:

(a) anode/hole transport layer/light-emitting layer/cathode;

(b) anode/hole injection layer/hole transport layer/light-emitting layer/cathode;

(c) anode/light-emitting layer/electron transport layer/cathode;

(d) anode/light-emitting layer/electron transport layer/electron injection layer/cathode;

(e) anode/hole transport layer/light-emitting layer/electron transport layer/cathode;

(f) anode/hole injection layer/hole transport layer/light-emitting layer/electron transport layer/cathode; and (g) anode/hole injection layer/hole transport layer/light-emitting layer/electron transport layer/electron injection layer/cathode.

Note that the symbol "/" means that layers sandwiching the symbol "/" are stacked adjacent to each other.

The anode in the device of the present invention supplies holes to the hole injection layer, the hole transport layer, the light-emitting layer, and has a work function of preferably 4.5 eV or higher.

A metal, an alloy, a metal oxide, an electric conductive compound, a mixture thereof and the like may be used as the material of the anode. Examples of the material of the anode include: conductive metal oxides such as tin oxide, zinc oxide, indium oxide, and indium-tin oxide (ITO); metals such as gold, silver, chromium, and nickel; mixtures and stacked bodies of any of these conductive metal oxides and metals; inorganic conductive materials such as copper iodide and copper sulfide; organic conductive materials such as polyaniline, polythiophene (PEDOT and the like), and polypyrrole; and stacked bodies of ITO and any of these materials.

The cathode in the device of the present invention supplies electrons to the electron injection layer, the electron transport layer, the light-emitting layer.

A metal, an alloy, a metal halide, a metal oxide, an electric conductive compound, or a mixture thereof can be used as the material of the cathode. Examples of the material of the cathode include alkali metals (such as lithium, sodium, potassium, and cesium), fluorides thereof, oxides thereof, alkaline-earth metals (such as magnesium, calcium, and barium), fluorides thereof, oxides thereof, gold, silver, lead, aluminum, alloys and metal mixtures (such as sodium-potassium alloys, sodium-potassium metal mixtures, lithium-aluminum alloys, lithium-aluminum metal mixtures, magnesium-silver alloys, and magnesium-silver metal mixtures), rare-earth metals (such as ytterbium) and the like.

The hole injection layer and hole transport layer in the device of the present invention have the function of injecting holes from the anode, the function of transporting holes, or the function of blocking electrons injected from the cathode.

Any known materials can be used as the materials of the hole injection layer and the hole transport layer. Examples of the materials of the hole injection layer and the hole transport layer include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, organic silane derivatives, and polymers containing the above materials. Other examples of the materials of the hole injection layer and the hole transport layer include conductive polymers and oligomers such as aniline copolymers, thiophene oligomers, and polythiophene. These materials may be used alone or in combination of two or more. Each of the hole injection layer and the hole transport layer may have a single layer structure formed of one or at least two of the above materials or have a multilayer structure comprising a plurality of layers having the same composition or different compositions.

The electron injection layer and electron transport layer in the device of the present invention have the function of injecting electrons from the cathode, the function of transporting electrons, or the function of blocking holes injected from the anode.

Examples of the materials of the electron injection layer and the electron transport layer include: triazole derivatives; oxazole derivatives; oxadiazole derivatives; imidazole derivatives; fluorenone derivatives; anthraquinodimethane derivatives; anthrone derivatives; diphenylquinone derivatives; thiopyrandioxide derivatives; carbodiimide derivatives; fluorenylidene methane derivatives; distyrylpyrazine derivatives; tetracarboxylic anhydrides of aromatic rings such as naphthalene and perylene; various metal complexes typified by metal complexes of phthalocyanine derivatives and 8-quinolinol derivatives, metal phthalocyanine, and metal complexes with benzoxazole and benzothiazole as ligands; and organic silane derivatives. These materials may be used alone or in combination of two or more. The electron injection layer and the electron transport layer may have a single layer structure formed of one or at least two of the above materials or have a multilayer structure comprising a plurality of layers having the same composition or different compositions.

In the device of the present invention, insulating or semiconductive inorganic compounds can be used as the materials of the electron injection layer and the electron transport layer. When the electron injection layer and the electron transport layer are formed of insulators or semiconductors, current leakage can be effectively prevented to thereby improve an electron injection characteristic.

Examples of the insulators include alkali metal chalcogenides, alkaline-earth metal chalcogenides, halides of alkali metals, and halides of alkaline-earth metals.

CaO, BaO, SrO, BeO, BaS, and CaSe are preferred as the alkali metal chalcogenides.

Examples of the semiconductors include oxides, nitrides, and oxynitrides containing at least one device selected from among the group consisting of Ba, Ca, Sr, Yb, Al, Ga, In, Li, Na, Cd, Mg, Si, Ta, Sb, and Zn.

These materials may be used alone or in combination of two or more.

In the device of the present invention, a reducing dopant may be added to the interfacial region between the cathode and the film in contact therewith.

At least one compound selected from among the group consisting of alkali metals, alkaline-earth metals, rare-earth metals, oxides of alkali metals, halides of alkali metals, oxides of alkaline-earth metals, halides of alkaline-earth metals, oxides of rare-earth metals, halides of rare-earth metals, alkali metal complexes, alkaline-earth metal complexes, and rare-earth metal complexes is preferred as the reducing dopant.

The light-emitting layer in the device of the present invention has the function that allows holes to be injected from the anode or the hole injection layer during application of voltage, the function that allows electrons to be injected from the cathode or the electron injection layer, the function that allows the injected charges (electrons and holes) to migrate by the force of the electric field, and the function of providing sites for recombination of the electrons and holes so as to generate light.

Preferably, the light-emitting layer contains the above metal complex, the above metal-containing polymer compound, or the above composition and may further contain a host material with the above metal complex, the above metal-containing polymer compound, or the above composition as a guest material.

Examples of the host material include compounds having a fluorene skeleton, compounds having a carbazole skeleton, compounds having a diarylamine skeleton, compounds having a pyridine skeleton, compounds having a pyrazine skeleton, compounds having a triazine skeleton, and compounds having an arylsilane skeleton. Preferably, the T1 (the energy level of the lowest triplet excited state) of the host material is higher than that of the guest material. More preferably, the difference in T1 is larger than 0.2 eV. The host material may be a low molecular compound or a polymer compound.

A light-emitting layer in which the host material is doped with the above metal complex, the above metal-containing polymer compound, or the above composition can be formed by application of a mixture of the host material and the above metal complex, the above metal-containing polymer compound, or the above composition or by codeposition of these materials.

The thickness of each of the layers constituting the film comprised in the device of the present invention varies depending on the types of materials and the layer structure. The thickness of each of the layers constituting the film comprised in the device of the present invention is preferably several nm to 1 µm.

<Method for Manufacturing the Device>

The method for manufacturing the device of the present invention is a method for manufacturing a device comprising an anode, a cathode, and a film sandwiched (arranged) between the anode and the cathode. The method comprises the step of forming a film by a vacuum deposition film method using the metal complex represented by the formula (1) or a composition containing the metal complex represented by the formula (1) or comprises the step of preparing a coating liquid by dissolving the metal complex defined by the formula (1), the above metal-containing polymer compound, or the above composition in a solvent and the step of applying the prepared liquid to form a film containing the above metal complex, the above metal-containing polymer compound, or the above composition.

Examples of the method for forming each of the layers provided in the device of the present invention include vacuum deposition methods (such as a resistive heating deposition method and an electron beam method), a sputtering method, an LB method, a molecular stacking method, and coating methods (such as casting method, spin coating method, bar coating method, blade coating method, role coating method, gravure printing method, screen printing method, and inkjet printing method).

Of these forming methods, a coating method is preferred because the manufacturing step can be simplified. When a film containing the metal complex, metal-containing polymer compound, or composition of the present invention is formed, a coating method can be used.

When the film containing the metal complex, metal-containing polymer compound, or composition of the present invention is formed using a coating method, a coating liquid (composition) is prepared by dissolving in a solvent (dispersing in a dispersion medium) the metal complex, metal-containing polymer compound, or composition of the present invention. Then the prepared coating liquid is applied to a prescribed layer (or an electrode) to form a film, and the film is dried.

When the coating method that uses a coating liquid to form a film is used, the film can be formed in air without using a large-scale facility such as a vacuum system. Therefore, a manufacturing step can be simplified, and the manufacturing cost can be reduced.

When the other layers are formed by a coating method, the same step may be used by using appropriate materials, solvents and the like.

The coating liquid may further contain a host material, an anti-oxidant, a viscosity modifier, and a resin serving as a binder.

The resin may be dissolved or dispersed in the solvent. Examples of the resin include polymer compounds such as polyvinylcarbazole and polyolefin. Specific examples of the resin include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethyl cellulose, vinyl acetate, ABS resins, polyurethane, melamine resins, unsaturated polyester resins, alkyd resins, epoxy resins, and silicone resins.

<Use Applications of the Device>

Examples of the use applications of the device of the present invention include a planar light source, a lighting device, a sign, a backlight, a display device, and a printer head. Any configuration such as a segment type or a dot-matrix type using a well-known driving technique, a well known driving circuit and the like can be selected for the display device.

EXAMPLES

Examples will next be described specifically. However, the present invention is not limited to the following Examples.

A number average molecular weight and a weight average molecular weight were determined using size exclusion chromatography (SEC) as a polystyrene-equivalent number average molecular weight and a polystyrene-equivalent weight average molecular weight. The SEC using an organic solvent as a mobile phase is referred to as gel permeation chromatography (GPC). The measurement of molecular weights by GPC was performed under the following (GPC-condition 1) or (GPC-condition 2).

(GPC-Condition 1)

A polymer compound used for the measurement was dissolved in tetrahydrofuran at a concentration of about 0.05% by weight, and 10 µL of the obtained solution was injected into a GPC (product name: LC-10Avp, manufactured by Shimadzu Corporation). Tetrahydrofuran was used as the mobile phase of the GPC and supplied thereto at a flow rate of 2.0 mL/min. PLgel MIXED-B (manufactured by Polymer Laboratories) was used as a column. The detector used was a UV-VIS detector (product name: SPD-10Avp, manufactured by Shimadzu Corporation).

(GPC-Condition 2)

A polymer compound used for the measurement was dissolved in tetrahydrofuran at a concentration of about 0.05% by weight, and 30 µL of the obtained solution was injected into a GPC (product name: LC-10Avp, manufactured by Shimadzu Corporation). Tetrahydrofuran was used as the mobile phase of the GPC and supplied thereto at a flow rate of 0.6 mL/min. Two TSKgel SuperHM-H columns (manufactured by TOSOH Corporation) and one TSKgel SuperH2000 column (manufactured by TOSOH Corporation) were connected in series. The detector used was a differential refractometer (product name: RID-10A, manufactured by Shimadzu Corporation).

NMR measurement was performed using a method under the following (NMR measurement condition 1) or (NMR measurement condition 2).

(NMR Measurement Condition 1)

5 mg to 10 mg of a measurement sample was dissolved in about 0.5 mL of deuteriochloroform and subjected to measurement using an NMR apparatus (product name: JME-EX270 FT-NMR system, manufactured by JEOL Ltd.).

(NMR Measurement Condition 2)

5 mg to 30 mg of a measurement sample was dissolved in about 0.5 mL of deuteriochloroform and subjected to measurement using an NMR apparatus (product name: MERCURY 300, manufactured by Varian, Inc.).

Infrared absorption spectrum (IR) measurement was performed using a spectrometer (product name: FTIR-8300, manufactured by Shimadzu Corporation).

ESI-MS measurement was performed using a spectrometer (device name: micromass ZQ, manufactured by Waters).

LC-MS measurement was performed by the following method. A measurement sample was dissolved in chloroform or tetrahydrofuran at a concentration of about 2 mg/mL, and 1 μL of the prepared solution was injected into an LC-MS (product name: 1100LCMSD, manufactured by Agilent Technologies). Ion exchanged water, acetonitrile, tetrahydrofuran, and a solution mixture thereof were used as the mobile phase of the LC-MS, and acetic acid was added if necessary. The column used was an L-column 2 ODS (3 μm) (inner diameter: 2.1 mm, length: 100 mm, particle diameter: 3 μm, manufactured by Chemicals Evaluation and Research Institute, Japan).

TLC-MS measurement was performed by the following method. A measurement sample was dissolved in chloroform, toluene, or tetrahydrofuran, and a small amount of the obtained solution was applied to the surface of a pre-cut TLC glass plate (product name: Silica gel 60 $F_{254}$, manufactured by Merck). The measurement was performed in a TLC-MS (product name: JMS-T100TD, manufactured by JEOL Ltd.) using helium gas heated to 240° C. to 350° C.

Synthesis Example 1

Synthesis of Low Molecular Compound M-1: Synthesis Method 1

A low molecular compound M-1 was synthesized according to the following scheme.

[Chemical formula 52]

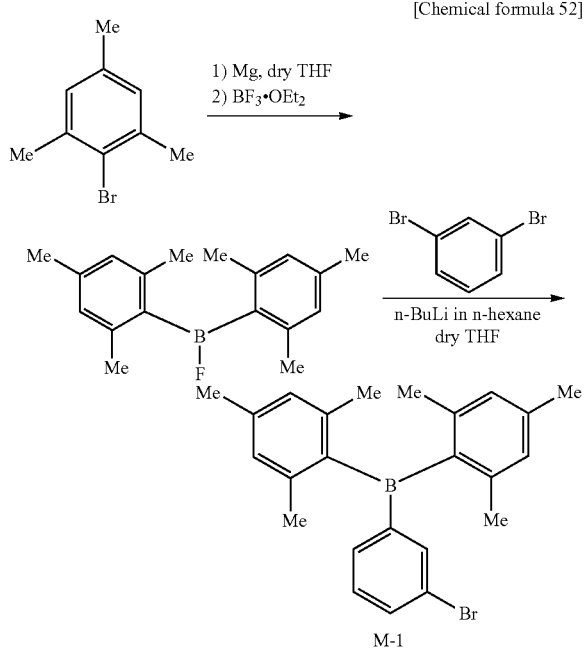

A pre-heated and dried three-neck flask was charged with magnesium (2.40 g, 98.8 mmol), and the atmosphere in the flask was replaced with an argon gas. Then dehydrated THF (50 mL) and 2-bromomesitylene (15 mL, 100 mmol) were added. The mixture was heated and refluxed under stirring for 2 hours. The reaction mixture was cooled to 0° C. using an ice bath, and a boron trifluoride-ethyl ether complex (6.3 mL, 50 mol) was added dropwise. The reaction mixture was heated and refluxed under stirring for 2 hours and then cooled to room temperature, thereby obtaining a suspension containing dimesitylfluoroborane (hereinafter may be referred to as "suspension A").

A pre-heated and dried Schlenk flask in which its internal atmosphere had been replaced with an argon gas was charged with 1,3-dibromobenzene (0.400 mL, 3.37 mmol) and dehydrated THF (30 mL), and the mixture was cooled to −78° C. using an acetone/dry ice bath. A 1.6 M n-hexane solution of n-butyl lithium (2.06 mL, 3.30 mmol) was added dropwise. While the temperature was maintained at −78° C., stirring was performed for 30 minutes, and the suspension A (10 mL) was added. The reaction solution was heated to room temperature and further stirred at room temperature for 10 hours. Then water and diethyl ether were added, and the organic layer was extracted. The extracted organic layer was washed with 1M hydrochloric acid and further with brine and dehydrated with anhydrous magnesium sulfate, and the solvent was removed under reduced pressure. The obtained residue was recrystallized using n-hexane, thereby obtaining 0.737 g of the low molecular compound M-1 as colorless crystals (yield; 59%). The synthesis of the low molecular compound M-1 was repeated a plurality of times, thereby obtaining the necessary amount of the low molecular compound M-1.

Melting point: 138.3° C. to 147.9° C.

IR $v_{max}/cm^{-1}$ 2916 ($CH_3$), 1605 (Ar), 1433 (Ar), 1238 (Ar), 843 (Ar).

$^1$H-NMR ($CDCl_3$, 270 MHz: (NMR measurement condition 1)) δ (ppm) 1.98 (s, 12H, $CH_3$, ortho), 2.30 (s, 6H, $CH_3$, para), 6.81 (s, 4H, mes-Ar—H), 7.21 (t, 1H, J=7.8 Hz, 4-Ar—H), 7.40 (d, 1H, J=7.3 Hz, 5-Ar—H), 7.58 (d, 1H, J=9.4 Hz, 6-Ar—H), 7.61 (s, 1H, 2-Ar—H).

Synthesis Example 2

Synthesis of Ligand BppyH: Synthesis Method 1

A ligand BppyH was synthesized according to the following scheme.

[Chemical formula 53]

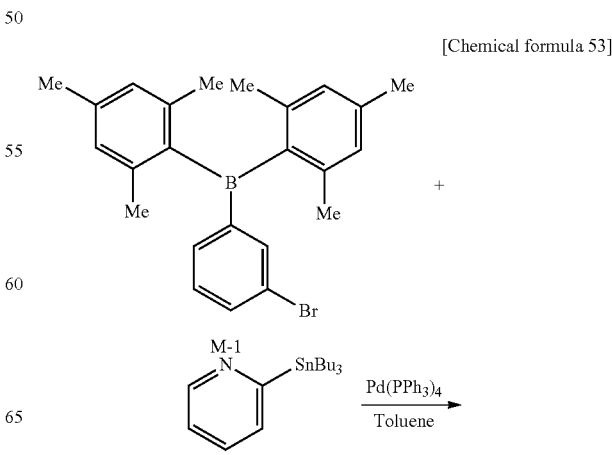

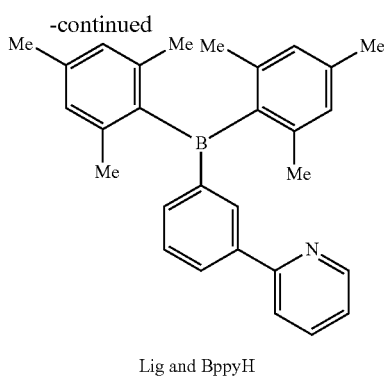

Lig and BppyH

A reaction vessel was charged with the low molecular compound M-1 (1.42 g, 3.49 mmol) obtained in Synthesis Example 1,2-(tri-n-butylstannyl)pyridine (2.57 g, 6.96 mmol), tetrakis(triphenylphosphine)palladium(0) (0.526 g, 0.449 mmol), and toluene (35 mL), and the mixture was heated and refluxed for 25 hours under stirring. After the mixture was cooled to room temperature, the solvent was removed under reduced pressure. The resultant residue was purified by column chromatography ($Al_2O_3$, developing solvent: $CHCl_3$:n-hexane=1:3 (volume ratio)) and recrystallized with n-hexane, thereby obtaining 0.488 g of the ligand BppyH as colorless needle-shaped crystals (yield: 35%).

Melting point: 164.5° C. to 166.7° C.

IR $\nu_{max}$/cm$^{-1}$ 2912 ($CH_3$), 1606 (Ar), 1590 (pyridine), 1459 (Ar), 1430 (pyridine), 1206 (pyridine), 844 (Ar), 770 (pyridine).

$^1$H-NMR ($CDCl_3$, 270 MHz: (NMR measurement condition 1)) δ (ppm) 2.02 (s, 12H, $CH_3$, ortho), 2.31 (s, 6H, $CH_3$, para), 6.82 (s, 4H, mes-Ar—H), 7.20 (ddd, 1H, J=1.3, 4.9, 7.3 Hz, 5-Ar—H), 7.47 (t, 1H, J=7.5 Hz, 4-Ar—H), 7.56 (td, 1H, J=1.3, 7.7 Hz, 4'-Ar—H), 7.61 (td, 1H, J=1.0, 8.1 Hz, 3-Ar—H), 7.70 (dt, 1H, J=1.8, 7.6 Hz, 5'-Ar—H), 8.03 (m, 1H, 2'-Ar—H), 8.17 (td, 1H, J=2.0, 7.6 Hz, 6'-Ar—H), 8.66 (ddd, 1H, J=0.89, 1.6, 4.9 Hz, 6-Ar—H).

Anal. Calcd. For $C_{29}H_{30}BN$: C, 86.35; H, 7.50; N, 3.47. Found: C, 86.27; H, 7.72; N, 3.49.

MS (ESI-MS) m/z 403 ($M^+$).

Synthesis Example 3

Synthesis of Binuclear Complex DM-1

A binuclear complex DM-1 was synthesized according to the following scheme.

[Chemical formula 54]

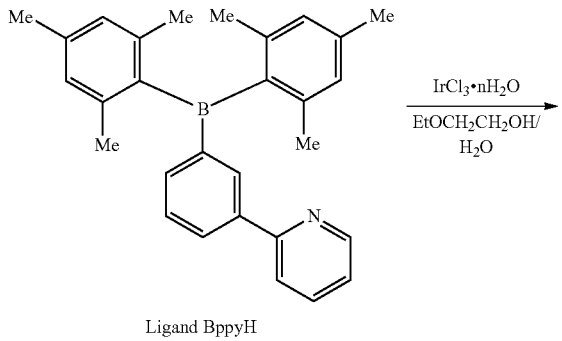

Ligand BppyH

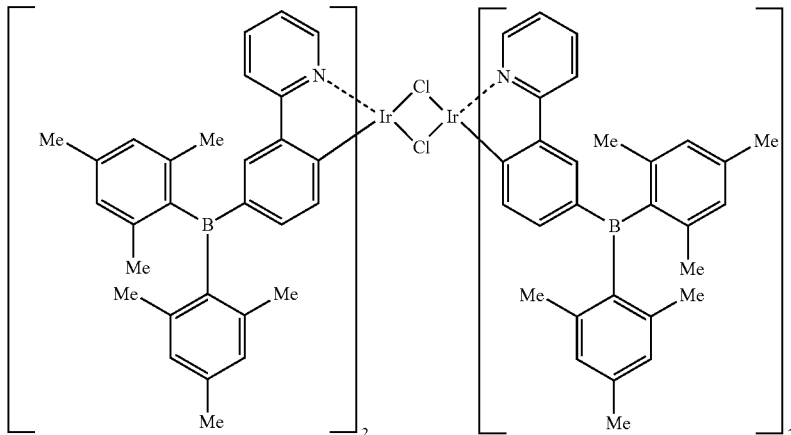

Binuclear complex DM-1

A reaction vessel was charged with iridium chloride(III) n-hydrate (0.131 g), the ligand BppyH (0.533 g, 1.32 mmol), 2-ethoxyethanol (32 mL), and water (11 mL), and the mixture was stirred at 145° C. in an argon gas atmosphere for 12 hours. Then the temperature was reduced to room temperature, and the resulting yellow precipitate was separated by filtration and washed with a large amount of water, thereby obtaining 0.310 g of the binuclear complex DM-1 as a yellow powder.

$^1$H-NMR (CDCl$_3$, 270 MHz: (NMR measurement condition 1)) δ (ppm) 1.89 (48H, s, CH$_3$, ortho), 2.26 (24H, s, CH$_3$, para), 5.88 (4H, d, J=7.9 Hz, 5-Ar—H), 6.63 (4H, dd, J=0.99, 8.0 Hz, 4-Ar—H), 6.73 (16H, s, mes-Ar—H), 7.00-7.20 (4H, m, 4'-Ar—H), 7.66 (4H, s, 2'-Ar—H), 7.69 (4H, t, J=6.8 Hz, 5'-Ar—H), 7.74 (4H, d, J=9.5 Hz, 3-Ar—H), 9.20 (4H, dd, J=0.97, 6.0 Hz, 6-Ar—H).

MS (ESI-MS) m/z 998 ([M-Ir(Bppy)$_2$Cl$_2$]$^+$).

Synthesis Example 4

Synthesis of Binuclear Complex DM-2

A binuclear complex DM-2 was synthesized according to the following scheme.

[Chemical formula 55]

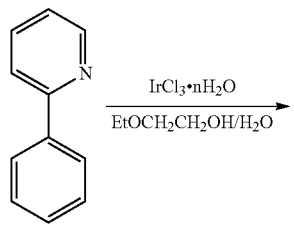

A reaction vessel was charged with iridium chloride(III) n-hydrate (65.5 mg), 2-phenylpyridine (0.102 g, 0.657 mmol), 2-ethoxyethanol (16 mL), and water (5.5 mL), and the mixture was stirred at 145° C. in an argon gas atmosphere for 12 hours. Then the temperature was reduced to room temperature, and the generated yellow precipitate was separated by filtration and washed with a large amount of water, thereby obtaining the binuclear complex DM-2 as a yellow powder.

$^1$H-NMR (CDCl$_3$, 270 MHz: (NMR measurement condition 1)) δ (ppm) 5.93 (4H, dd, J=1.0, 7.9 Hz, 2'-Ar—H), 6.56 (4H, dt, J=1.3, 7.4 Hz, 3'-Ar—H), 6.67-6.85 (8H, m, 4,4'-Ar—H), 7.48 (4H, dd, J=1.5, 7.8 Hz, 5'-Ar—H), 7.73 (4H, dt, J=1.5, 7.8 Hz, 5-Ar—H), 7.87 (4H, dd, J=0.70, 7.9 Hz, 3-Ar—H), 9.24 (4H, ddd, J=0.63, 1.6, 7.4 Hz, 6-Ar—H)

MS (ESI-MS) m/z 500 ([M-Ir(ppy)$_2$Cl$_2$]$^+$)

Example 1

Synthesis of Complex Ir-1

A complex Ir-1 was synthesized according to the following scheme.

[Chemical Formula 56]

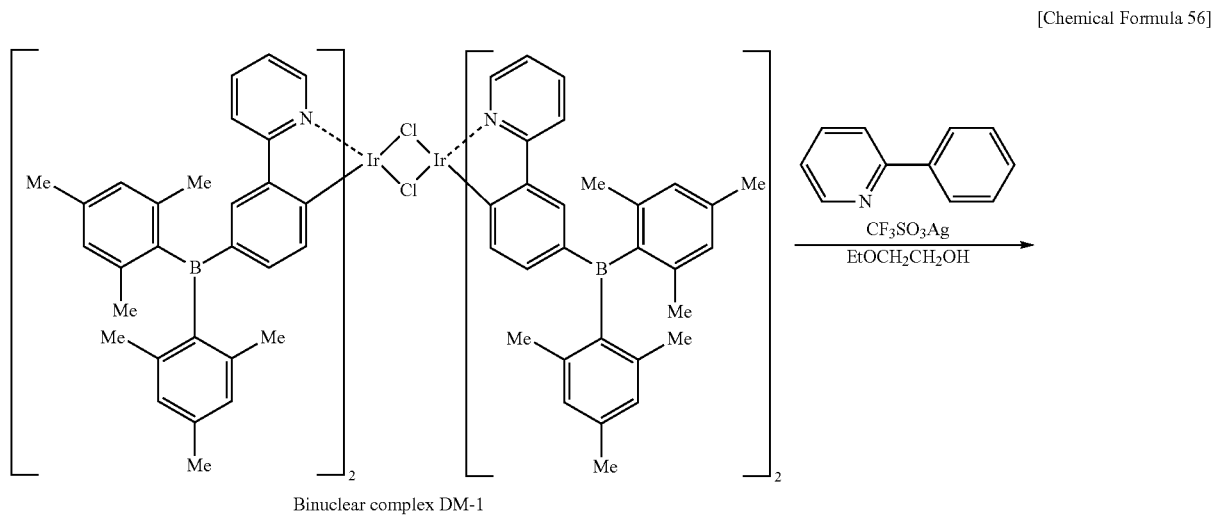

Binuclear complex DM-1

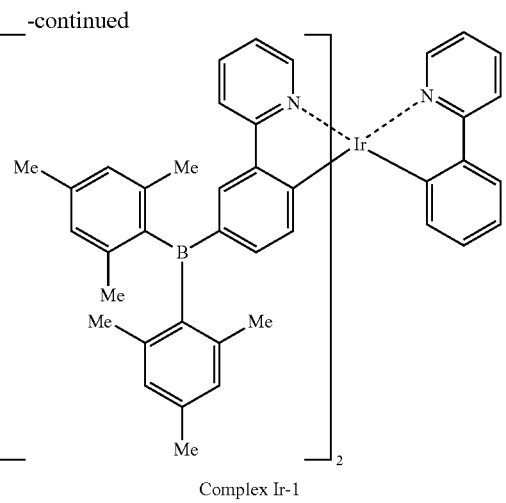

Complex Ir-1

A reaction vessel was charged with the binuclear complex DM-1 (32.1 mg, 0.0155 mmol), 2-phenylpyridine (14.6 mg, 0.0943 mmol), silver(I) trifluoromethanesulfonate (11.7 mg, 0.0446 mmol), and 2-ethoxyethanol (0.6 mL), and the mixture was stirred at 145° C. under an argon atmosphere for 15 hours. After the reaction mixture was cooled to room temperature, water was added, and the generated yellow precipitate was collected by filtration. The precipitate was purified by column chromatography (Sephadex (registered trademark) LH-20, developing solvent: chloroform) and subjected to two-phase diffusion (chloroform/n-hexane), thereby obtaining the complex Ir-1 as a yellow powder.

IR $\nu_{max}$/cm$^{-1}$ 2921 (CH$_3$), 1688 (Ar), 1558 (Ar-py), 1476 (Ar), 1346 (py), 1215 (py), 851 (Ar), 760 (py)

MS (ESI-MS) m/z 1153 (M$^+$).

Example 2

Synthesis of Complex Ir-2

A complex Ir-2 was synthesized according to the following scheme.

[Chemical Formula 57]

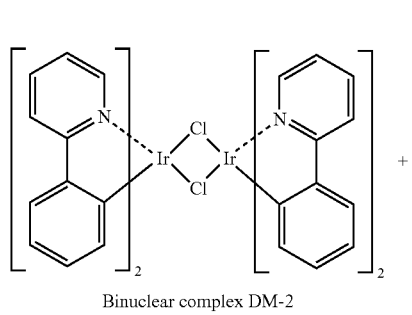

Binuclear complex DM-2

+

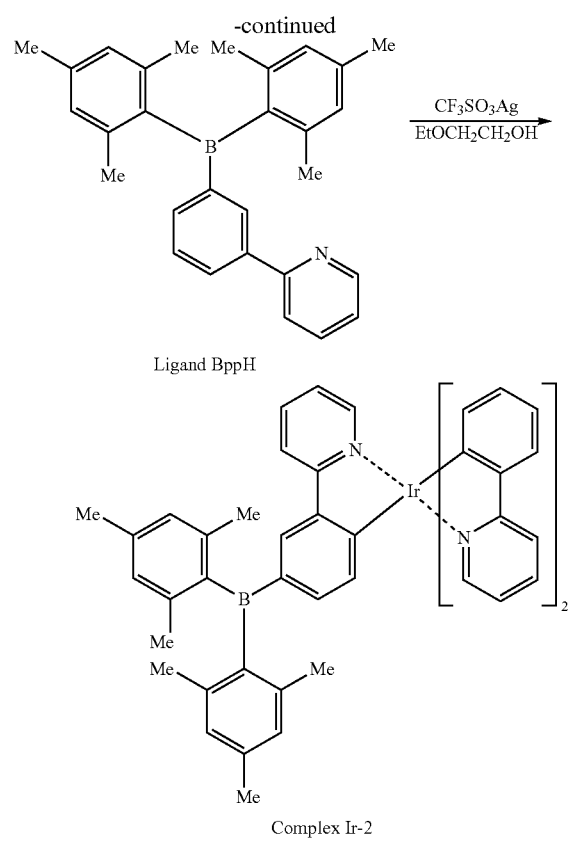

Ligand BppH

Complex Ir-2

A reaction vessel was charged with the binuclear complex DM-2 (21.1 mg, 0.0191 mmol), the ligand BppyH (36.6 mg, 0.0912 mmol), silver(I) trifluoromethanesulfonate (24.4 mg, 0.0949 mmol), and 2-ethoxyethanol (0.8 mL), and the mixture was stirred at 145° C. under an argon atmosphere for 6 hours. After the reaction mixture was cooled to room temperature, 3 mL of water was added, and the generated yellow precipitate was collected by filtration. The precipitate was purified by column chromatography (Sephadex (registered trademark) LH-20, developing solvent: chloroform) and subjected to two-phase diffusion (chloroform/n-hexane), thereby obtaining the complex Ir-2 as a yellow powder.

IR $\nu_{max}$/cm$^{-1}$ 2917 (CH$_3$), 1680 (Ar), 1587 (Ar-py), 1457 (Ar), 1414 (py), 1220 (py), 832 (Ar), 753 (py)
MS (ESI-MS) m/z 904 (M$^+$).

Synthesis Example 5

Synthesis of complex Ir-0

A complex Ir-0 (corresponding to a complex described as the metal complex represented by the formula (1-3)) was synthesized according to the following scheme.

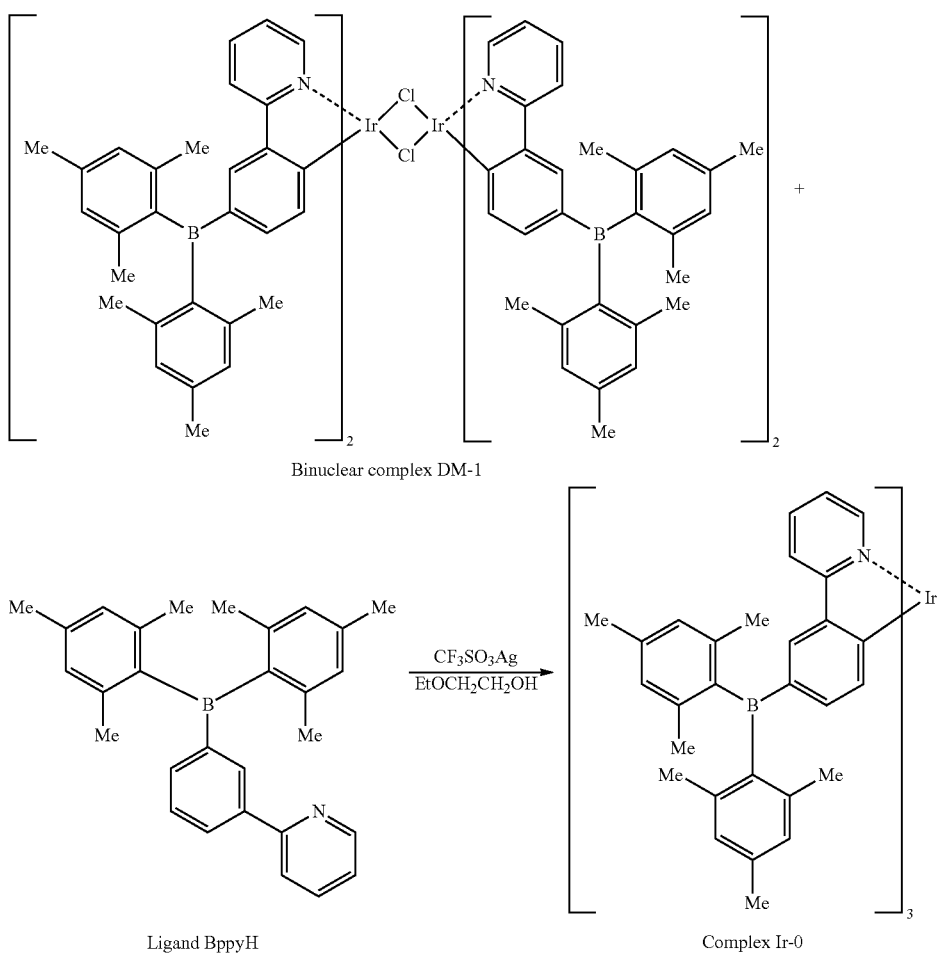

Binuclear complex DM-1

Ligand BppyH

Complex Ir-0

A reaction vessel was charged with the binuclear complex DM-1 (26.5 mg, 0.0128 mmol), the ligand BppyH (22.0 mg, 0.0546 mmol), silver(I) trifluoromethanesulfonate (7.0 mg, 0.0272 mmol), and 2-ethoxyethanol (0.5 mL), and the mixture was stirred at 145° C. under an argon atmosphere for 6 hours. After the reaction mixture was cooled to room temperature, water was added, and the generated yellow precipitate was collected by filtration. The precipitate was purified by column chromatography (Sephadex (registered trademark) LH-20, developing solvent: chloroform) and subjected to two-phase diffusion (chloroform/diethyl ether), thereby obtaining 0.01 g of the complex Ir-0 as a yellow powder.

$^1$H-NMR (CDCl$_3$, 270 MHz: (NMR measurement condition 1)) δ (ppm) 2.00 (36H, s, CH$_3$, ortho), 2.30 (18H, s, CH$_3$, para), 6.77 (12H, s, mes-Ar—H), 6.84-6.94 (9H, m, 4,5,4'-Ar—H), 7.47 (3H, d, J=5.1 Hz, 3-Ar—H), 7.56 (3H, t, J=7.7 Hz, 5'-Ar—H), 7.70-7.80 (6H, m, 6,2'-Ar—H).

Anal. Calcd. for C$_{87}$H$_{87}$B$_3$N$_3$Ir (0.1CH$_2$Cl$_2$): C, 74.31; H, 6.24; N, 2.98. Found: C, 74.03; H, 6.32; N, 2.93.
MS (ESI-MS) m/z 1401 (M$^+$).

<Solubility of Metal Complexes>

The solubilities of the complexes Ir-1 and Ir-2 in chloroform, toluene, n-hexane, diethyl ether, tetrahydrofuran, and ethanol as solvents were higher than that of tris(2-phenylpyridine)iridium. The solubilities in n-hexane and diethyl ether having low polarity were particularly higher.

[Chemical Formula 58]

<Light-Emitting Efficiency of Devices>

The above metal complexes Ir-1 and Ir-2 as the materials of the light-emitting layers of devices are dissolved in solvents to prepare solutions, and the devices having light-emitting layers formed by applying the solutions have high light-emitting efficiency.

Synthesis Example 6

Synthesis of Low Molecular Compound M-2

A low molecular compound M-2 was synthesized according to the following scheme.

[Chemical Formula 59]

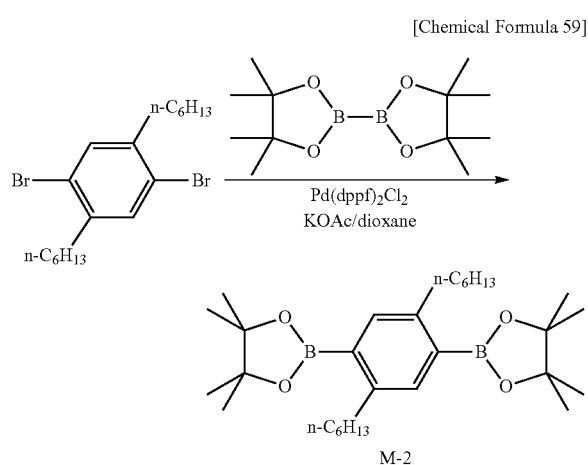

A 300 mL four-necked flask was charged with 1,4-dihexyl-2,5-dibromobenzene (8.08 g), bis(pinacolate)diboron (12.19 g), and potassium acetate (11.78 g), and the atmosphere in the flask was replaced with an argon gas. Then dehydrated 1,4-dioxane (100 mL) was added, and the mixture was degassed with an argon gas. [1,1'-Bis(diphenylphosphino)ferrocene]dichloropalladium(II) (Pd(dppf)$_2$Cl$_2$) (0.98 g) was added, and the mixture in the flask was degassed with an argon gas and heated and refluxed for 6 hours. Toluene was added to the mixture, and the resultant mixture was washed with ion exchanged water. Anhydrous sodium sulfate and activated carbon were added to the washed organic layer, and the resultant mixture was filtrated using a funnel pre-coated with Celite.

The obtained filtrate was concentrated, thereby obtaining 11.94 g of dark brown crystals. The crystals were recrystallized with n-hexane, and the resultant crystals were washed with methanol. The obtained crystals were dried under reduced pressure, thereby obtaining 4.23 g of the low molecular compound M-2 as white needle-shaped crystals (yield: 42%).

$^1$H-NMR (300 MHz, CDCl$_3$: (NMR measurement condition 2)) δ (ppm) 0.88 (t, 6H), 1.23-1.40 (m, 36H), 1.47-1.56 (m, 4H), 2.81 (t, 4H), 7.52 (s, 2H)

LC-MS (ESI, positive): m/z$^+$=573 [M+K]$^+$

Synthesis Example 7

Synthesis of Low Molecular Compound M-3

A low molecular compound M-3 was synthesized according to the following scheme.

[Chemical Formula 60]

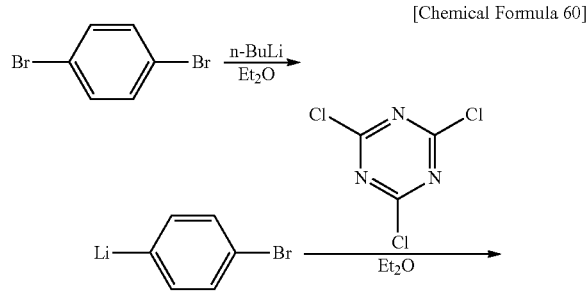

A reaction vessel in a nitrogen atmosphere was charged with a dehydrated diethyl ether solution (217 mL) containing 1,4-dibromobenzene (27.1 g) dissolved therein. The reaction vessel was cooled using a dry ice/methanol mixture bath. A 2.77M hexane solution (37.2 mL) of n-butyl lithium was slowly added dropwise to the obtained suspension, and the resultant mixture was stirred for 1 hour to prepare a lithium reagent.

In a reaction vessel, a suspension prepared by dissolving cyanuric chloride (10.0 g) in dehydrated diethyl ether (68 mL) was cooled in a nitrogen atmosphere using a dry ice/methanol mixture bath. Then the above-prepared lithium reagent was slowly added thereto, and the mixture was heated to room temperate to allow the mixture to react. The obtained product was filtrated and dried under reduced pressure. The obtained solid (16.5 g) was purified, thereby obtaining 13.2 g of needle-shaped crystals.

[Chemical Formula 61]

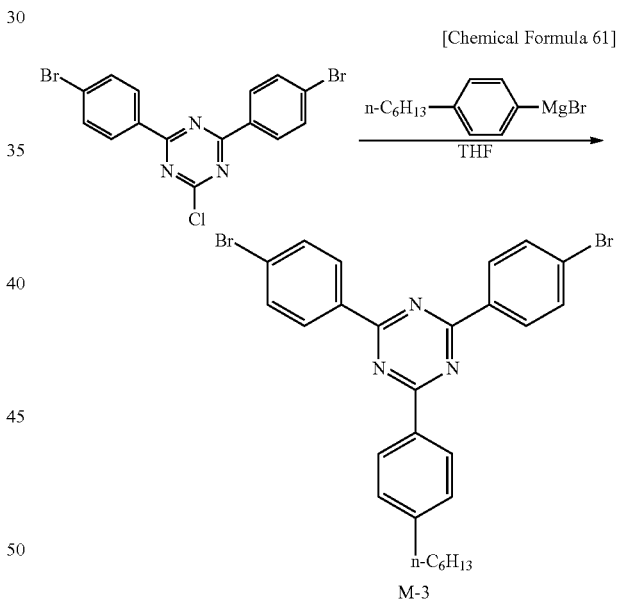

In a reaction vessel, a solution prepared by dissolving 4-hexylbromobenzene (14.2 g) in dehydrated tetrahydrofuran (15 mL) was gradually added under a nitrogen atmosphere to a suspension prepared by adding dehydrated tetrahydrofuran (65 mL) to magnesium (1.37 g), and the mixture was heated and stirred under reflux. After the reaction solution was left to cool, magnesium (0.39 g) was further added thereto, and the resultant mixture was again heated and allowed to react under reflux to prepare a Grignard reagent.

In a reaction vessel, the Grignard reagent was added, in a nitrogen atmosphere under stirring, to a suspension prepared by dissolving the above-prepared needle-shaped crystals (12.0 g) in dehydrated tetrahydrofuran (100 mL), and the mixture was heated and refluxed. After left to cool, the reaction solution was washed with an aqueous dilute hydrochloric acid solution. The organic layer and the aqueous layer were separated from each other, and the aqueous layer was extracted with diethyl ether. The obtained organic layers were mixed together, and the organic layer was again washed with water. The obtained organic layer was dehydrated with anhydrous magnesium sulfate, filtrated, and concentrated. The obtained white solid was purified using a silica gel column and further recrystallized, thereby obtaining 6.5 g of the compound M-3 as a white solid.

$^1$H-NMR (300 MHz, CDCl$_3$: (NMR measurement condition 2)) δ (ppm) 0.90 (t, J=6.2 Hz, 3H), 1.25-1.42 (m, 6H), 1.63-1.73 (m, 2H), 2.71 (t, J=7.6 Hz, 2H), 7.34 (d, J=7.9 Hz, 2H), 7.65 (d, J=7.9 Hz, 4H), 8.53-8.58 (m, 6H)

LC-MS (APCI, positive): m/z$^+$=566 [M+H]$^+$

Synthesis Example 8

Synthesis of Polymer Compound P-1

In a reaction vessel, the low molecular compound M-2 (3.13 g), the low molecular compound M-3 (0.70 g), 2,7-dibromo-9,9-dioctylfluorene (2.86 g), palladium acetate(II) (2.1 mg), tris(2-methoxyphenyl)phosphine (13.4 mg), and toluene (80 mL) were mixed under a nitrogen atmosphere, and the mixture was heated to 100° C. under stirring. A 20% by weight aqueous tetraethylammonium hydroxide solution (21.5 mL) was added dropwise to the reaction solution, and the resultant mixture was refluxed for 5 hours. Phenylboronic acid (78 mg), palladium acetate(II) (2.1 mg), tris(2-methoxyphenyl)phosphine (13.3 mg), toluene (6 mL), and a 20% by weight aqueous tetraethylammonium hydroxide solution (21.5 mL) were added to the reaction solution, and the resultant mixture was further refluxed for 17.5 hours. Then a 0.2M aqueous sodium diethyldithiocarbamate solution (70 mL) was added thereto, and the resultant mixture was stirred at 85° C. for 2 hours.

The reaction solution was cooled to room temperature and washed three times with water, three times with a 3% by weight aqueous acetic acid solution, and three times with water. The organic layer was added dropwise to methanol, and a precipitate was thereby formed. The precipitate was filtrated and dried, thereby obtaining a solid. The solid was dissolved in toluene and purified through an alumina column and a silica gel column. The obtained eluate was added dropwise to methanol, and the obtained precipitate was collected by filtration and dried, thereby obtaining 3.43 g of a polymer compound P-1. The polystyrene-equivalent number average molecular weight of the polymer compound P-1 was 1.9×10$^5$, and its polystyrene-equivalent weight average molecular weight was 5.7×10$^5$ (GPC-condition 1).

The polymer compound P-1 is a copolymer comprising a structural unit represented by the following formula:

[Chemical Formula 62]

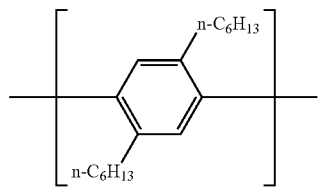

a structural unit represented by the following formula:

[Chemical Formula 63]

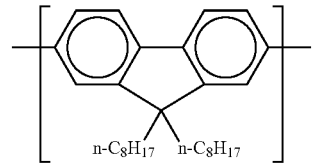

and a structural unit represented by the following formula:

[Chemical Formula 64]

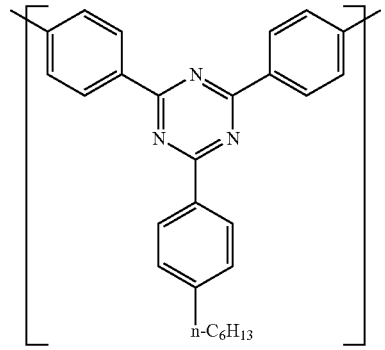

at a molar ratio of 50:40:10 as a theoretical ratio determined from the raw materials used for the preparation.

Synthesis Example 9

Synthesis of Polymer Compound P-2

The compound M-2 (2.81 g), the compound M-3 (0.62 g), 2,7-dibromo-9,9-bis(4-hexylphenyl)fluorene (2.90 g), palladium acetate(II) (1.9 mg), tris(2-methoxyphenyl)phosphine (11.9 mg), and toluene (85 mL) were mixed under a nitrogen atmosphere, and the mixture was heated to 100° C. under stirring. A 20% by weight aqueous tetraethylammonium hydroxide solution (19.1 mL) was added dropwise to the reaction solution, and the resultant mixture was refluxed for 5 hours. Phenylboronic acid (69 mg), palladium acetate(II) (1.9 mg), tris(2-methoxyphenyl)phosphine (11.9 mg), and toluene (6 mL) were added to the reaction solution, and the resultant mixture was further refluxed for 15.5 hours. After the aqueous layer was removed, a 0.2M aqueous sodium diethyldithiocarbamate solution (63 mL) was added, and the resultant mixture was stirred at 85° C. for 2 hours. The reaction solution was cooled to room temperature and washed twice with water, twice with a 3% by weight aqueous acetic acid solution, and twice with water. The organic layer was added dropwise to methanol, and a precipitate was thereby formed. The obtained precipitate was filtrated and dried, thereby obtaining a solid. The solid was dissolved in toluene and purified through an alumina column and a silica gel column. The obtained eluate was added dropwise to methanol, and the obtained precipitate was collected by filtration and dried, thereby obtaining 3.52 g of a polymer compound P-2. The polystyrene-equivalent number average molecular weight of the polymer compound P-2 was 1.5×10$^5$, and its polystyrene-equivalent weight average molecular weight was 4.7×10$^5$ (GPC-condition 2).

The polymer compound P-2 is a copolymer comprising a structural unit represented by the following formula:

[Chemical Formula 65]

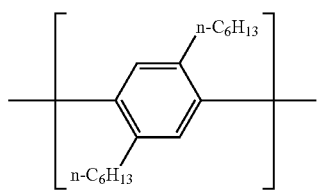

a structural unit represented by the following formula:

[Chemical Formula 66]

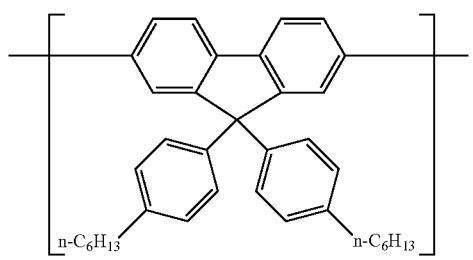

and a structural unit represented by the following formula:

[Chemical Formula 67]

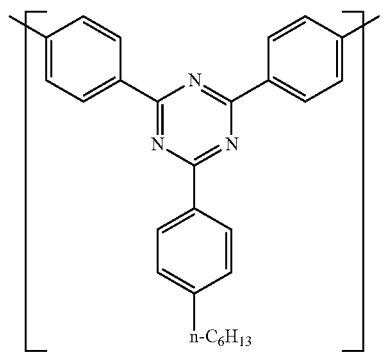

at a molar ratio of 50:40:10 as a theoretical ratio determined from the raw materials used for the preparation.

Solution Preparation Example 1

Preparation of Polymer Solution PVK

Poly(9-vinylcarbazole) (manufactured by Sigma-Aldrich, weight average molecular weight: 1,100,000 or less, powder form) (11 mg) was dissolved in chlorobenzene (manufactured by Wako Pure Chemical Industries, Ltd., Wako special grade) (1.79 g) to prepare a solution (this solution is hereinafter referred to as "polymer solution PVK").

Solution Preparation Example 2

Preparation of Complex Solution Ir-0

The complex Ir-0 (4.8 mg) was dispersed in toluene (manufactured by KANTO CHEMICAL Co., Inc., electronics industry use (EL grade)) (7.25 g). The dispersion was heated and stirred at 80° C. to completely dissolve the complex Ir-0, and a solution was thereby prepared (this solution is hereinafter referred to as "complex solution Ir-0").

Example 3

Preparation of Complex Composition Solution M0P1

The polymer compound P-1 (0.048 g) and the complex solution Ir-0 (3.80 g) were added to toluene (manufactured by KANTO CHEMICAL Co., Inc., electronics industry use (EL grade)) (1.15 g). The mixture was heated and stirred at 80° C. to completely dissolve the compound, and a solution was thereby prepared (this solution is hereinafter referred to as "complex composition solution M0P1"). The complex composition solution M0P1 contained the polymer compound P-1 and the complex Ir-0 at a weight ratio of 95:5.

Example 4

Preparation of Complex Composition Solution M0P2

The polymer compound P-2 (0.043 g) and the complex solution Ir-0 (3.45 g) were added to toluene (manufactured by KANTO CHEMICAL Co., Inc., electronics industry use (EL grade)) (1.05 g), and the mixture was heated and stirred at 80° C. to completely dissolve the compound, and a solution was thereby prepared (this solution is hereinafter referred to as "complex composition solution M0P2"). The complex composition solution M0P2 contained the polymer compound P-2 and the complex Ir-0 at a weight ratio of 95:5.

Solution Preparation Example 3

Preparation of Complex Solution Ref-1

Tris(2-phenylpyridine)iridium represented by the following formula (manufactured by Luminescence Technology Corp., Sublimed Grade) (1.8 mg) was dispersed in toluene (manufactured by KANTO CHEMICAL Co., Inc., electronics industry use (EL grade)), (3.47 g), and the mixture was heated and stirred at 80° C. However, the tris(2-phenylpyridine)iridium could not be completely dissolved.

[Chemical Formula 68]

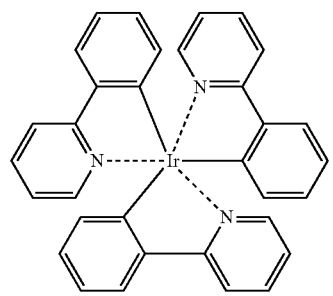

Tris (2-phenylpyridine) iridium

Solution Preparation Example 4

Preparation of Complex Solution Ref-2

Tris(2-phenylpyridine)iridium (manufactured by Luminescence Technology Corp., Sublimed Grade) (5.1 mg) was dispersed in chloroform (manufactured by Wako Pure Chemical Industries, Ltd., pure solvent for fluorescence analysis, test and research use) (7.71 g), and the dispersion was heated and stirred at 60° C. to completely dissolve the tris(2-phenylpyridine)iridium, and a solution was thereby prepared (this solution is hereinafter referred to as "complex solution Ref-2").

Comparative Example 3

Preparation of Complex Composition Solution R2P1

The polymer compound P-1 (53.2 mg) and the complex solution Ref-2 (4.25 g) were added to chloroform (manufactured by Wako Pure Chemical Industries, Ltd., pure solvent for fluorescence analysis, test and research use) (14.35 g). The mixture was heated to 60° C. and stirred to completely dissolve the compound, and a solution was thereby prepared (this solution is hereinafter referred to as "complex composition solution R2P1"). The complex composition solution R2P1 contained the polymer compound P-1 and tris(2-phenylpyridine)iridium at a weight ratio of 95:5.

Comparative Example 4

Preparation of Complex Composition Solution R2P2

The polymer compound P-2 (43.2 mg) and the complex solution Ref-2 (3.46 g) were added to chloroform (manufactured by Wako Pure Chemical Industries, Ltd., pure solvent for fluorescence analysis, test and research use) (13.35 g). The mixture was heated to 60° C. and stirred to completely dissolve the compound, and a solution was thereby prepared (this solution is hereinafter referred to as "complex composition solution R2P2"). The complex composition solution R2P2 contained the polymer compound P-2 and tris(2-phenylpyridine)iridium at a weight ratio of 95:5.

Example 5

Light-Emitting Device C01

A polythiophene-sulfonic acid-based hole injection agent AQ-1200 (manufactured by Plextronics) was placed on a glass substrate having a 45 nm-thick ITO film formed thereon by sputtering, and a film was formed by spin coating method so as to have a thickness of about 65 nm and dried on a hot plate at 170° C. for 15 minutes. The polymer solution PVK was placed on the obtained AQ-1200 film, and a film was formed by spin coating method so as to have a thickness of about 20 nm and dried at 180° C. under a nitrogen atmosphere with oxygen and water concentrations of 10 ppm or less (weight basis) for 60 minutes. Then the complex composition solution M0P1 was placed on the film obtained using the polymer solution PVK, and a light-emitting layer was formed by spin coating method so as to have a thickness of about 80 nm. Then the obtained film was dried at 130° C. in a nitrogen atmosphere with oxygen and water concentrations of 10 ppm or less (weight basis) for 10 minutes. After pressure was reduced to $1.0 \times 10^{-4}$ Pa or lower, a NaF layer serving as a cathode was formed on the film of the light-emitting layer L01 by vapor deposition so as to have a thickness of about 4 nm, and then an aluminum layer was formed on the NaF layer by vapor deposition so as to have a thickness of about 72 nm. After the vapor deposition of the NaF layer and the aluminum layer, the product was sealed with a glass substrate, thereby manufacturing a light-emitting device C01.

A voltage was applied to the obtained light-emitting device C01 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 42.9 cd/A. The maximum light-emitting efficiency was 50.2 cd/A.

Example 6

Light-Emitting Device C02

A light-emitting device C02 was manufactured as in Example 5 except that the complex composition solution M0P2 was used instead of the complex composition solution M0P1 used in Example 5.

A voltage was applied to the obtained light-emitting device C02 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 40.2 cd/A. The maximum light-emitting efficiency was 48.9 cd/A.

Comparative Example 5

Light-Emitting Device CR21

A light-emitting device CR21 was manufactured as in Example 5 except that the complex composition solution R2P1 was used instead of the complex composition solution M0P1 used in Example 5.

A voltage was applied to the obtained light-emitting device CR21 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 13.6 cd/A. The maximum light-emitting efficiency was 18.8 cd/A.

Comparative Example 6

Light-Emitting Device CR22

A light-emitting device CR22 was manufactured as in Example 5 except that the complex composition solution R2P2 was used instead of the complex composition solution M0P1 used in Example 5.

A voltage was applied to the obtained light-emitting device CR22 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 20.3 cd/A. The maximum light-emitting efficiency was 23.9 cd/A.

Synthesis Example 10

Synthesis of Ligand BppyH, Synthesis Method 2

The ligand BppyH was synthesized according to the following scheme different from the scheme in Synthesis Example 2.

[Chemical Formula 69]

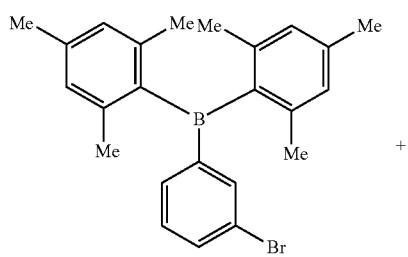

Low molecular compound M-1

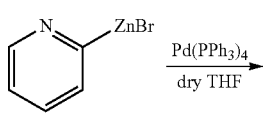

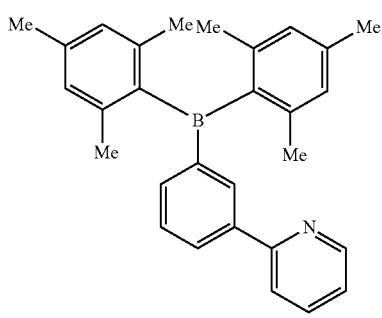

Ligand BppyH

A reaction vessel in which its interior atmosphere had been replaced with a nitrogen gas was charged with the low molecular compound M-1 (116 g, 286 mmol), tetrakis(triphenylphosphine)palladium(0) (20 g, 17.3 mmol), and dry THF (860 mL), and the mixture was stirred at room temperature. A THF solution (660 mL) of 2-pyridyl zinc bromide adjusted to 0.5 M was slowly added dropwise thereto. After completion of dropwise addition, the mixture was heated and stirred for 3 hours under reflux. Then the reaction solution was diluted with tert-butyl methyl ether (1000 mL), and the organic layer was washed with 1M hydrochloric acid (1000 mL) and then with a 1M aqueous sodium hydrogencarbonate solution (1000 mL). The obtained organic layer was dehydrated with magnesium sulfate, and the solvent was removed under reduced pressure. The obtained residue was purified by column chromatography (silica gel, developing solvent: $CHCl_3$: n-hexane=1:3 (volume ratio)) and dispersed in n-hexane, and the dispersion was stirred and filtrated, thereby obtaining 98.3 g of ligand BppyH as colorless crystals (yield: 81%).

$^1$H-NMR ($CDCl_3$, 300 MHz: (NMR measurement condition 2)) δ (ppm) 2.02 (s, 12H, $CH_3$, ortho), 2.31 (s, 6H, $CH_3$, para), 6.82 (s, 4H, mes-Ar—H), 7.18 (ddd, 1H, J=1.2, 4.8, 7.3 Hz, 5-Ar—H), 7.47 (t, 1H, J=7.5 Hz, 4-Ar—H), 7.56 (td, 1H, J=1.4, 7.5 Hz, 4'-Ar—H), 7.60 (td, 1H, J=1.0, 8.0 Hz, 3-Ar—H), 7.68 (dt, 1H, J=1.7, 7.6 Hz, 5'-Ar—H), 8.04 (brs, 1H, 2'-Ar—H), 8.17 (td, 1H, J=1.7, 7.7 Hz, 6'-Ar—H), 8.65 (ddd, 1H, J=0.8, 1.7, 4.9 Hz, 6-Ar—H).

TLC-MS (DART, positive): $m/z^+$=403 $[M+H]^+$

Example 7

Synthesis of Complex Ir-3

A complex Ir-3 was synthesized according to the following scheme.

[Chemical Formula 70]

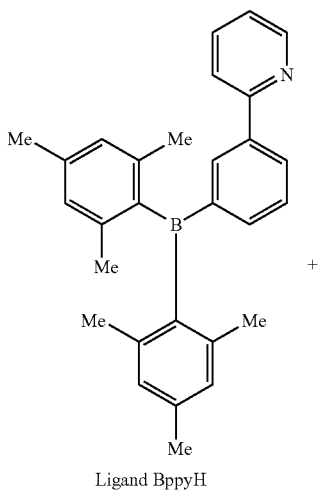

Ligand BppyH

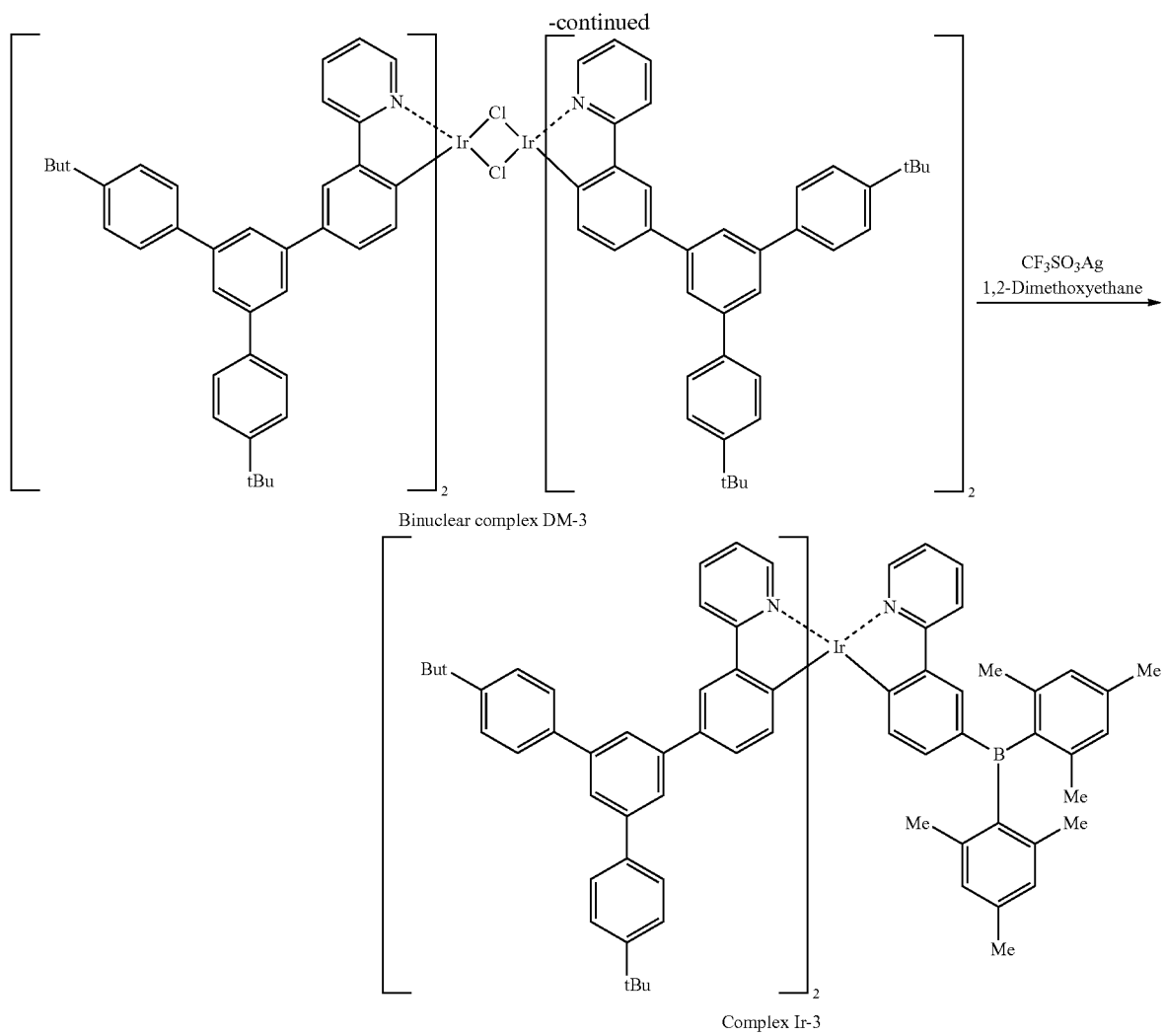

Binuclear complex DM-3

Complex Ir-3

A reaction vessel in which its interior atmosphere had been replaced with a nitrogen gas was charged with the binuclear complex DM-3 (3.65 g, 1.50 mmol), the ligand BppyH (3.63 g, 9.00 mmol), silver(I) trifluoromethanesulfonate (770 mg, 3.00 mmol), and 1,2-dimethoxyethane (60 mL), and the mixture was stirred at 105° C. under a nitrogen atmosphere for 16 hours. After the reaction mixture was cooled to room temperature, water was added, and the generated yellow precipitate was collected by filtration. The filtrated precipitate was washed with methanol and then hexane. The obtained yellow precipitate was dispersed in 100 mL of chloroform and filtrated to remove insoluble components, and the solvent was removed from the filtrate under reduced pressure. The obtained residue was purified by column chromatography (silica gel, developing solvent: $CHCl_3$:n-hexane=2:3 (volume ratio)). Finally, the residue was dispersed in n-hexane, stirred, and filtrated, thereby obtaining 1.3 g of the complex Ir-3 as a yellow powder.

$^1$H-NMR ($CDCl_3$, 300 MHz: (NMR measurement condition 2)) δ (ppm) 1.37 (brs, 36H, tBu), 2.05 (s, 12H, $CH_3$, ortho), 2.31 (s, 6H, $CH_3$, para), 6.77 (s, 4H, mes-Ar—H), 6.87-7.05 (m, 7H), 7.20-7.23 (m, 2H), 7.45-7.83 (m, 30H), 7.93-8.01 (m, 4H).

LC-MS (APCI, positive): m/z$^+$=1582 [M+H]$^+$

The binuclear complex DM-3 was synthesized according to the synthesis method described in WO02/066552. Namely, in a reaction vessel, 2-(3'-bromophenyl)pyridine was obtained under a nitrogen atmosphere by Suzuki coupling of 2-bromopyridine and 1.2 equivalents of 3-bromophenylboronic acid (catalyst: tetrakis(triphenylphosphine)palladium (0), base: 2M aqueous sodium carbonate solution, solvent: ethanol and toluene).

[Chemical Formula 71]

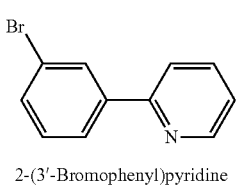

2-(3'-Bromophenyl)pyridine

Next, in a reaction vessel, under a nitrogen atmosphere, by Suzuki coupling of tribromobenzene and 2.2 equivalents of 4-tert-butylphenylboronic acid (catalyst: tetrakis(triphenylphosphine)palladium(0), base: 2M aqueous sodium carbonate solution, solvent: ethanol and toluene), a brominated compound represented by the following formula:

[Chemical Formula 72]

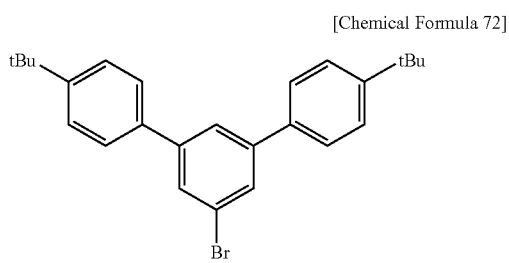 [SMILES: CC(C)(C)c1ccc(-c2cc(Br)cc(-c3ccc(C(C)(C)C)cc3)c2)cc1]

was obtained.

The obtained brominated compound was dissolved in dehydrated THF in a reaction vessel under a nitrogen atmosphere. The obtained solution was cooled to −78° C., and a small excess of tert-butyl lithium was added dropwise thereto. After cooling, B(OC$_4$H$_9$)$_3$ was added dropwise to allow the mixture to react at room temperature. The reaction solution was post-treated with 3M hydrochloric acid, thereby obtaining a compound represented by the following formula:

[Chemical Formula 73]

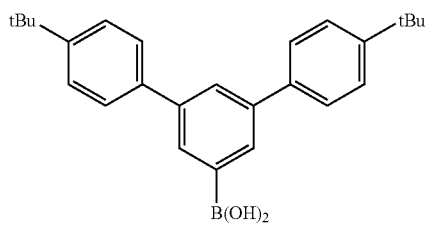

serving as a boronic acid compound.

A ligand TPppyH was obtained by Suzuki coupling of 2-(3'-bromophenyl)pyridine and 1.2 equivalents of the boronic acid compound (catalyst: tetrakis(triphenylphosphine)palladium(0), base: 2M aqueous sodium carbonate solution, solvent: ethanol and toluene).

[Chemical Formula 74]

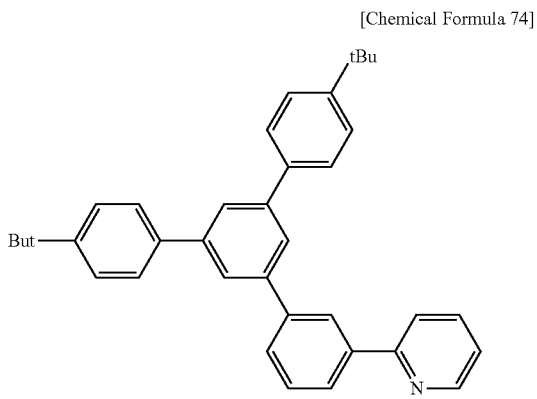

Ligand TPppyH

A reaction vessel was charged with IrCl$_3$.3H$_2$O, 2.2 equivalents of the ligand TPppyH, 2-ethoxyethanol, and ion exchanged water under an argon atmosphere, and the mixture was refluxed. The precipitated solid was subjected to suction filtration. The obtained solid was washed with ethanol and then ion exchanged water and dried, thereby obtaining a binuclear complex DM-3 as a yellow powder.

[Chemical Formula 75]

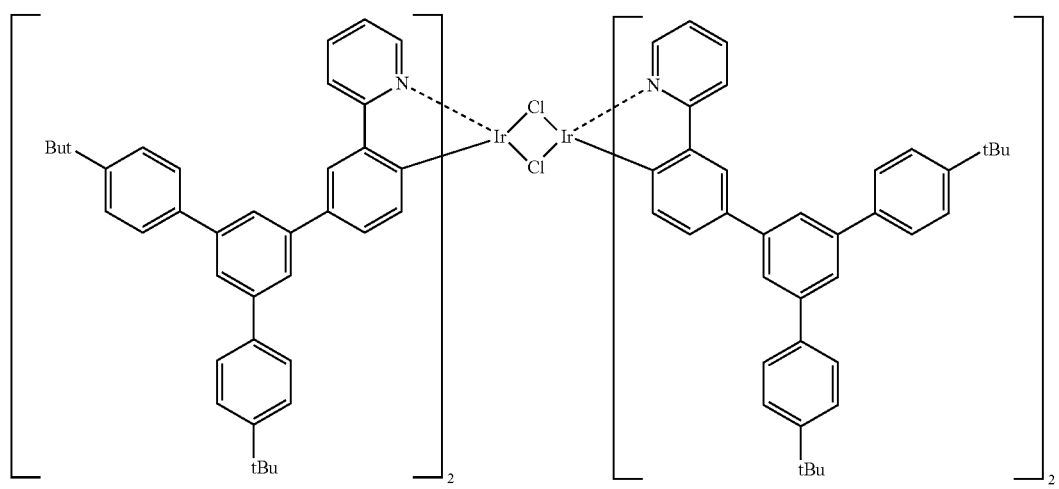

Binuclear complex DM-3

Example 8

Synthesis of Complex Ir-4

A complex Ir-3 was synthesized according to the following scheme.

A reaction vessel in which its interior atmosphere had been replaced with a nitrogen gas was charged with the binuclear complex DM-1 (4.87 g, 2.4 mmol), the ligand TPppyH (5.95 g, 12 mmol) obtained as the synthetic intermediate of the binuclear complex DM-3, silver(I) trifluoromethanesulfonate (1.03 g, 4 mmol), and 2-ethoxyethanol (80 mL), and the

[Chemical Formula 76]

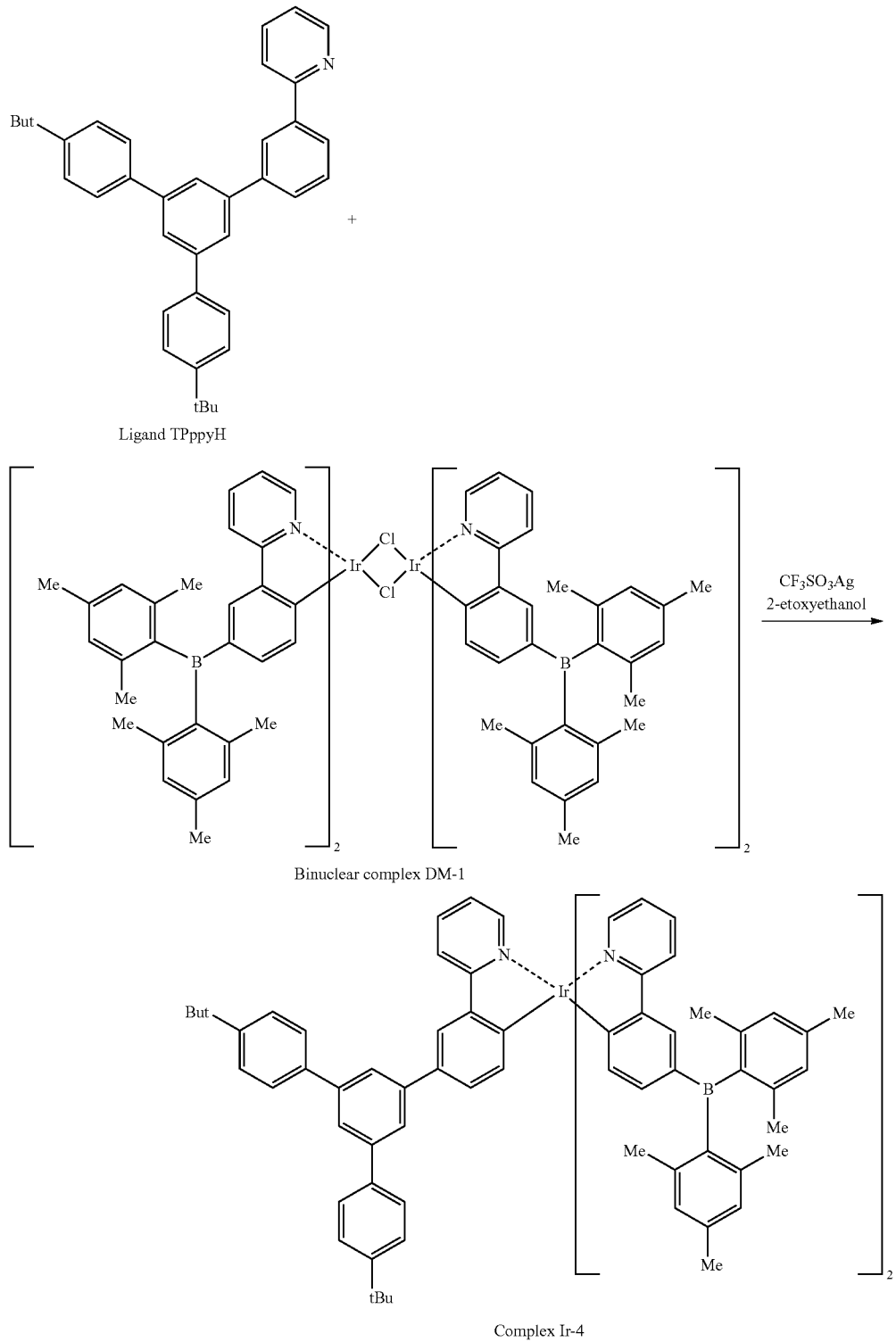

mixture was stirred at 137° C. under a nitrogen atmosphere for 8 hours. After the reaction mixture was cooled to room temperature, 80 mL of ion exchanged water was added, and the generated yellow precipitate was collected by filtration. The filtrated precipitate was washed with methanol and then hexane, dispersed in hexane, stirred, and filtrated, and the resultant precipitate was repeatedly purified by column chromatography (silica gel, developing solvent: $CHCl_3$:n-hexane=1:4 to 1:1 (volume ratio)). Finally, the precipitate was dispersed in n-hexane, stirred, and filtrated, thereby obtaining 510 mg of the complex Ir-4 as a yellow powder.

LC-MS (APCI, positive): $m/z^+$=1489 $[M+H]^+$

Example 9

Preparation of Complex Solution Ir-3

The complex Ir-3 (50 mg) was added to toluene (manufactured by KANTO CHEMICAL Co., Inc., electronics industry use (EL grade)) (2.08 g). The mixture was stirred under a room temperature condition to completely dissolve the complex, and a solution was thereby prepared. This solution was diluted with toluene (manufactured by KANTO CHEMICAL Co., Inc., electronics industry use (EL grade)) to prepare a 1.1% by weight toluene solution of the complex Ir-3 (this solution is hereinafter referred to as "complex solution Ir-3").

Example 10

Preparation of Complex Solution Ir-4

The complex Ir-4 (50 mg) was added to toluene (manufactured by KANTO CHEMICAL Co., Inc., electronics industry use (EL grade)) (2.08 g). The mixture was stirred in a room temperature condition to completely dissolve the complex, and a solution was thereby produced. This solution was diluted with toluene (manufactured by KANTO CHEMICAL Co., Inc., electronics industry use (EL grade)) to prepare a 1.1% by weight toluene solution of the complex Ir-4 (this solution is hereinafter referred to as "complex solution Ir-4").

Example 11

Preparation of Complex Composition Solution M3P1

A solution prepared by dissolving the polymer compound P-1 in toluene (manufactured by KANTO CHEMICAL Co., Inc., electronics industry use (EL grade)) at a concentration of 1.1% by weight was mixed with the complex solution Ir-3 at a weight ratio of 95:5 to prepare a solution (this solution is hereinafter referred to as "complex composition solution M3P1").

Example 12

Preparation of Complex Composition Solution M3P2

A solution prepared by dissolving the polymer compound P-2 in toluene (manufactured by KANTO CHEMICAL Co., Inc., electronics industry use (EL grade)) at a concentration of 1.1% by weight was mixed with the complex solution Ir-3 at a weight ratio of 95:5 to prepare a solution (this solution is hereinafter referred to as "complex composition solution M3P2").

Example 13

Preparation of Complex Composition Solution M4P1

A solution prepared by dissolving the polymer compound P-1 in toluene (manufactured by KANTO CHEMICAL Co., Inc., electronics industry use (EL grade)) at a concentration of 1.1% by weight was mixed with the complex solution Ir-4 at a weight ratio of 95:5 to prepare a solution (this solution is hereinafter referred to as "complex composition solution M4P1").

Example 14

Preparation of Complex Composition Solution M4P2

A solution prepared by dissolving the polymer compound P-2 in toluene (manufactured by KANTO CHEMICAL Co., Inc., electronics industry use (EL grade)) at a concentration of 1.1% by weight was mixed with the complex solution Ir-4 at a weight ratio of 95:5 to prepare a solution (this solution is hereinafter referred to as "complex composition solution M4P2").

Example 15

Light-Emitting Device C31

A polythiophene-sulfonic acid-based hole injection agent AQ-1200 (manufactured by Plextronics) was placed on a glass substrate having a 45 nm-thick ITO film formed thereon by sputtering method, and a film was formed by spin coating method so as to have a thickness of about 65 nm and dried on a hot plate at 170° C. for 15 minutes. The polymer solution PVK was placed on the obtained AQ-1200 film, and a film was formed by spin coating method so as to have a thickness of about 20 nm and dried at 180° C. under a nitrogen atmosphere with oxygen and water concentrations of 10 ppm or less (weight basis) for 60 minutes. Then the complex composition solution M3P1 was placed on the film obtained using the polymer solution PVK, and a light-emitting layer was formed by spin coating method so as to have a thickness of about 80 nm. Then the obtained film was dried at 130° C. under a nitrogen atmosphere with oxygen and water concentrations of 10 ppm or less (weight basis) for 10 minutes. After pressure was reduced to $1.0 \times 10^{-4}$ Pa or lower, NaF was vapor-deposited to a thickness of about 4 nm on the film of the light-emitting layer L31 to form a cathode, and aluminum was vapor-deposited to a thickness of about 70 nm on the NaF layer. After the vapor deposition, the product was sealed with a glass substrate, thereby manufacturing a light-emitting device C31.

A voltage was applied to the obtained light-emitting device C31 using an OLED TEST SYSTEM manufactured by Tokyo System Kaihatsu Co., Ltd. to cause the device to emit light, and green electroluminescence was observed. The light-emitting efficiency at a brightness of 1000 cd/$m^2$ was 61.9 cd/A. The maximum light-emitting efficiency was 70.1 cd/A.

Example 16

Light-Emitting Device C32

A polythiophene-sulfonic acid-based hole injection agent AQ-1200 (manufactured by Plextronics) was placed on a glass substrate having a 45 nm-thick ITO film formed thereon by sputtering method, and a film was formed by spin coating method so as to have a thickness of about 65 nm and dried on a hot plate at 170° C. for 15 minutes. The polymer solution PVK was placed on the obtained AQ-1200 film, and a film was formed by spin coating method so as to have a thickness of about 20 nm and dried at 180° C. in a nitrogen atmosphere with oxygen and water concentrations of 10 ppm or less (weight basis) for 60 minutes. Then the complex composition solution M3P2 was placed on the film obtained using the polymer solution PVK, and a light-emitting layer was formed by spin coating method so as to have a thickness of about 80 nm. Then the obtained film was dried at 130° C. under a nitrogen atmosphere with oxygen and water concentrations of 10 ppm or less (weight basis) for 10 minutes. After pressure was reduced to $1.0 \times 10^{-4}$ Pa or lower, NaF was vapor-deposited to a thickness of about 4 nm on the film of the light-emitting layer L32 to form a cathode, and aluminum was vapor-deposited to a thickness of about 70 nm on the NaF layer. After the vapor deposition, the product was sealed with a glass substrate, thereby manufacturing a light-emitting device C32.

A voltage was applied to the obtained light-emitting device C32 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 63.5 cd/A. The maximum light-emitting efficiency was 71.1 cd/A.

Example 17

Light-Emitting Device C41

A polythiophene-sulfonic acid-based hole injection agent AQ-1200 (manufactured by Plextronics) was placed on a glass substrate having a 45 nm-thick ITO film formed thereon by sputtering method, and a film was formed by spin coating method so as to have a thickness of about 65 nm and dried on a hot plate at 170° C. for 15 minutes. The polymer solution PVK was placed on the obtained AQ-1200 film, and a film was formed by spin coating method so as to have a thickness of about 20 nm and dried at 180° C. under a nitrogen atmosphere with oxygen and water concentrations of 10 ppm or less (weight basis) for 60 minutes. Then the complex composition solution M4P1 was placed on the film obtained using the polymer solution PVK, and a light-emitting layer was formed by spin coating method so as to have a thickness of about 80 nm. Then the obtained film was dried at 130° C. under a nitrogen atmosphere with oxygen and water concentrations of 10 ppm or less (weight basis) for 10 minutes. After pressure was reduced to $1.0 \times 10^{-4}$ Pa or lower, NaF was vapor-deposited to a thickness of about 4 nm on the film of the light-emitting layer L41 to form a cathode, and aluminum was vapor-deposited to a thickness of about 70 nm on the NaF layer. After the vapor deposition, the product was sealed with a glass substrate, thereby manufacturing a light-emitting device C41.

A voltage was applied to the obtained light-emitting device C41 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 61.7 cd/A. The maximum light-emitting efficiency was 69.7 cd/A.

Example 18

Light-Emitting Device C42

A polythiophene-sulfonic acid-based hole injection agent AQ-1200 (manufactured by Plextronics) was placed on a glass substrate having a 45 nm-thick ITO film formed thereon by sputtering method, and a film was formed by spin coating method so as to have a thickness of about 65 nm and dried on a hot plate at 170° C. for 15 minutes. The polymer solution PVK was placed on the obtained AQ-1200 film, and a film was formed by spin coating method so as to have a thickness of about 20 nm and dried at 180° C. under a nitrogen atmosphere with oxygen and water concentrations of 10 ppm or less (weight basis) for 60 minutes. Then the complex composition solution M4P2 was placed on the film obtained using the polymer solution PVK, and a light-emitting layer was formed by spin coating method so as to have a thickness of about 80 nm. Then the obtained film was dried at 130° C. under a nitrogen atmosphere with oxygen and water concentrations of 10 ppm or less (weight basis) for 10 minutes. After pressure was reduced to $1.0 \times 10^{-4}$ Pa or lower, NaF was vapor-deposited to a thickness of about 4 nm on the film of the light-emitting layer L42 to form a cathode, and aluminum was vapor-deposited to a thickness of about 70 nm on the NaF layer. After the vapor deposition, the product was sealed with a glass substrate, thereby manufacturing a light-emitting device C42.

A voltage was applied to the obtained light-emitting device C42 using an OLED TEST SYSTEM manufactured by Tokyo System Kaihatsu Co., Ltd. to cause the device to emit light, and green electroluminescence was observed. The light-emitting efficiency at a brightness of 1000 cd/m$^2$ was 58.5 cd/A. The maximum light-emitting efficiency was 65.8 cd/A.

For each of the manufactured light-emitting devices, the constituents of the light-emitting layer, the light-emitting efficiency at a brightness of 1000 cd/m$^2$, and the maximum light-emitting efficiency are listed in TABLE 1 below. In TABLE 1, "Ir(ppy)$_3$" represents a tris(2-phenylpyridine)iridium complex.

TABLE 1

|  | LIGHT-EMITTING DEVICE | LIGHT-EMITTING LAYER | LIGHT-EMITTING EFFICIENCY AT BRIGHTNESS OF 1000 cd/m$^2$ | MAXIMUM LIGHT-EMITTING EFFICIENCY |
|---|---|---|---|---|
| EXAMPLE 5 | LIGHT-EMITTING DEVICE C01 | COMPLEX Ir-0/ POLYMER COMPOUND P-1 | 42.9 cd/A | 50.2 cd/A |
| EXAMPLE 6 | LIGHT-EMITTING DEVICE C02 | COMPLEX Ir-0/ POLYMER COMPOUND P-2 | 40.2 cd/A | 48.9 cd/A |
| EXAMPLE 15 | LIGHT-EMITTING DEVICE C31 | COMPLEX Ir-3/ POLYMER COMPOUND P-1 | 61.9 cd/A | 70.1 cd/A |

TABLE 1-continued

| | LIGHT-EMITTING DEVICE | LIGHT-EMITTING LAYER | LIGHT-EMITTING EFFICIENCY AT BRIGHTNESS OF 1000 cd/m² | MAXIMUM LIGHT-EMITTING EFFICIENCY |
|---|---|---|---|---|
| EXAMPLE 16 | LIGHT-EMITTING DEVICE C32 | COMPLEX Ir-3/ POLYMER COMPOUND P-2 | 63.5 cd/A | 71.1 cd/A |
| EXAMPLE 17 | LIGHT-EMITTING DEVICE C41 | COMPLEX Ir-4/ POLYMER COMPOUND P-1 | 61.7 cd/A | 69.7 cd/A |
| EXAMPLE 18 | LIGHT-EMITTING DEVICE C42 | COMPLEX Ir-4/ POLYMER COMPOUND P-2 | 58.5 cd/A | 65.8 cd/A |
| COMPARATIVE EXAMPLE 5 | LIGHT-EMITTING DEVICE CR21 | Ir(ppy)$_3$/ POLYMER COMPOUND P-1 | 13.6 cd/A | 18.8 cd/A |
| COMPARATIVE EXAMPLE 6 | LIGHT-EMITTING DEVICE CR22 | Ir(ppy)$_3$/ POLYMER COMPOUND P-2 | 20.3 cd/A | 23.9 cd/A |

As is clear from TABLE 1, each of the light-emitting devices produced using the metal complexes of the present invention had higher light-emitting efficiency than the light-emitting devices produced using the conventional metal complex (tris(2-phenylpyridine)iridium complex) as the material of the light-emitting layer.

The invention claimed is:
1. A metal complex represented by formula (1):

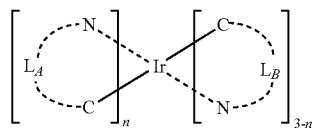

wherein:
in formula (1), n is 1 or 2; $L_A$ and $L_B$ each independently represent a moiety of a group bonded to an iridium atom except for coordinating atoms; a group represented by formula (1-1):

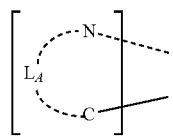

means a group represented by formula (L1):

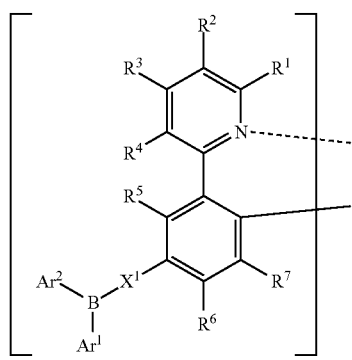

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ each independently represent an aryl group optionally having a substituent or a monovalent aromatic heterocyclic group optionally having a substituent; $X^1$ represents a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by formula (1-2):

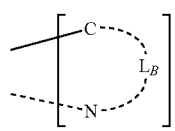

is different from the group represented by the formula (1-1) and means a group represented by a formula (L2):

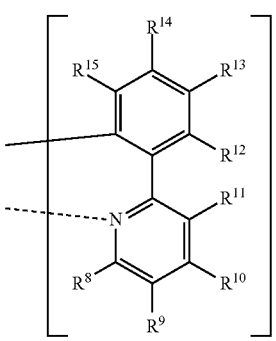

wherein, in formula (L2), $R^8$, $R^9$, $R^{10}$, $R^{11}$, $R^{12}$, $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; and when two groups represented by the formula (1-1) are present, the groups represented by the formula (1-1) may be the same as or different from each other; and when two groups represented by the formula (1-2) are present, the groups represented by the formula (1-2) may be the same as or different from each other.

2. The metal complex according to claim 1, wherein the group represented by the formula (L1) is a group represented by formula (L1-1):

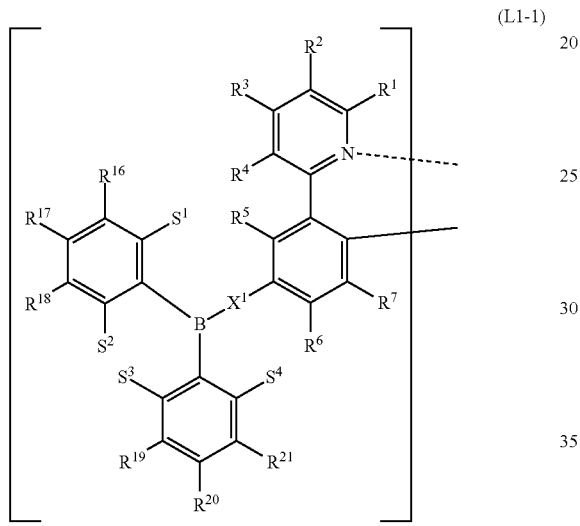

(L1-1)

wherein, in formula (L1-1), $R^1$, $R^2$, $R^3$, $R^4$, $R^5$, $R^6$, $R^7$, and $X^1$ are as defined above; $R^{16}$, $R^{17}$, $R^{18}$, $R^{19}$, $R^{20}$, and $R^{21}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $S^1$, $S^2$, $S^3$, and $S^4$ each independently represent an alkyl group, an alkoxy group, an aryl group, an aralkyl group, a substituted amino group, or a monovalent aromatic heterocyclic group; and these groups may have a substituent.

3. The metal complex according to claim 2, wherein $S^1$, $S^2$, $S^3$, and $S^4$ are each independently an alkyl group, an aryl group, a substituted amino group, or a monovalent aromatic heterocyclic group.

4. The metal complex according to claim 2, wherein $S^1$, $S^2$, $S^3$, and $S^4$ are each independently an alkyl group or an aryl group.

5. The metal complex according to claim 2, wherein $S^1$, $S^2$, $S^3$, and $S^4$ are an alkyl group.

6. The metal complex according to claim 1, wherein $X^1$ is a direct bond.

7. The metal complex according to claim 2, wherein at least one of $R^{16}$, $R^{17}$, $R^{18}$, $R^{19}$, $R^{20}$, and $R^{21}$ is an alkyl group.

8. A composition comprising:
a charge transporting material; and
a metal complex represented by formula (1):

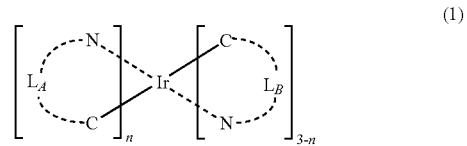

(1)

wherein:
in formula (1), n is 1 or 2: $L_A$ and $L_B$ each independently represent a moiety of a group bonded to an iridium atom except for coordinating atoms; a group represented by formula (1-1):

(1-1)

means a group represented by formula (L1):

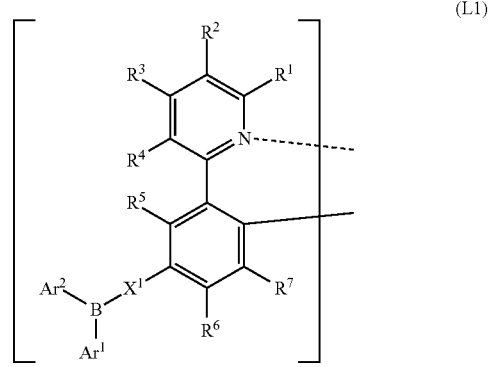

(L1)

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ each independently represent an aryl group optionally having a substituent or a monovalent aromatic heterocyclic group optionally having a substituent; $X^1$ represents a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by formula (1-2):

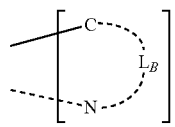

is different from the group represented by the formula (1-1) and means a group represented by formula (L2):

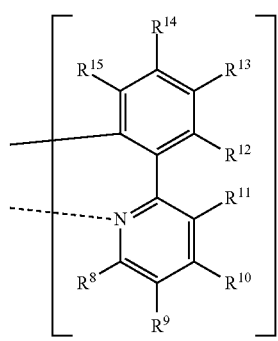

wherein, in formula (L2), $R^8$, $R^9$, $R^{10}$, $R^{11}$, $R^{12}$, $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; and when two groups represented by the formula (1-1) are present, the groups represented by the formula (1-1) may be the same as or different from each other; and when two groups represented by the formula (1-2) are present, the groups represented by the formula (1-2) may be the same as or different each other.

9. The composition according to claim 8, wherein the charge transporting material is a polymer compound.

10. The composition according to claim 8, wherein the charge transporting material is a polymer compound having, as a structural unit, at least one group selected from among the group consisting of a bivalent aromatic amine residue, an arylene group, and a bivalent aromatic heterocyclic group.

11. The composition according to claim 8, wherein the charge transporting material is a polymer compound having, as structural units, at least two groups selected from among the group consisting of a bivalent aromatic amine residue, an arylene group, and a bivalent aromatic heterocyclic group.

12. A metal-containing polymer compound comprising: as a structural unit, a group derived from a metal complex represented by formula (1):

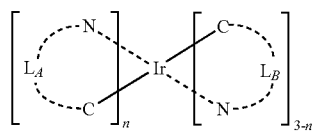

wherein:

in formula (1), n is 1 or 2: $L_A$ and $L_B$ each independently represent a moiety of a group bonded to an iridium atom except for coordinating atoms; a group represented by formula (1-1):

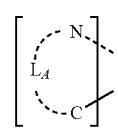

means a group represented by formula (L1):

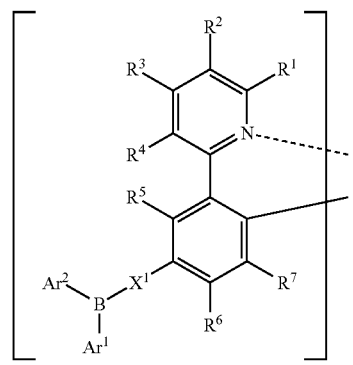

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ are each independently an aryl group optionally having a substituent or a monovalent aromatic heterocyclic group optionally having a substituent; $X^1$ is a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by formula (1-2):

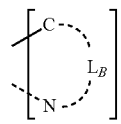

is different from the group represented by the formula (1-1) and means a group represented by formula (L2):

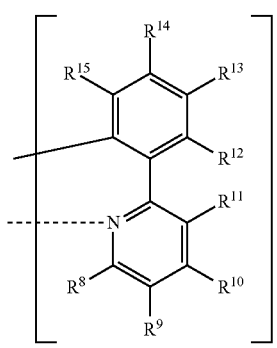

wherein, in formula (L2), $R^8$, $R^9$, $R^{10}$, $R^{11}$, $R^{12}$, $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; and when two groups represented by the formula (1-1) are present, the groups represented by the formula (1-1) may be the same as or different from each other; and when two groups represented by the formula (1-2) are present, the groups represented by the formula (1-2) may be the same as or different from each other.

13. The metal-containing polymer compound according to claim 12, wherein the metal-containing polymer compound comprises, as a structural unit, at least one group selected from among the group consisting of a bivalent aromatic amine residue, an arylene group, and a bivalent aromatic heterocyclic group.

14. The metal-containing polymer compound according to claim 12, wherein the metal-containing polymer compound comprises, as structural units, at least two groups selected from among the group consisting of a bivalent aromatic amine residue, an arylene group, and a bivalent aromatic heterocyclic group.

15. A composition comprising:
    the metal-containing polymer compound according to claim 12; and
    a charge transporting material.

16. A composition comprising:
    a solvent or a dispersion medium; and
    a metal complex represented by formula (1):

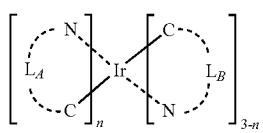

wherein:
in formula (1), n is 1 or 2: $L_A$ and $L_B$ each independently represent a moiety of a group bonded to an iridium atom except for coordinating atoms; a group represented by formula (1-1):

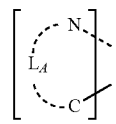

means a group represented by a formula (L1):

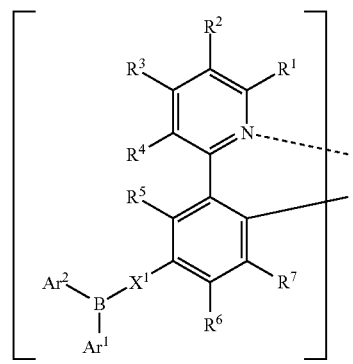

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ each independently represent an aryl group optionally having a substituent or a monovalent aromatic heterocyclic group optionally having a substituent; $X^1$ represents a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by a formula (1-2):

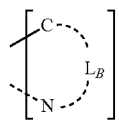

is different from the group represented by the formula (1-1) and means a group represented by formula (L2):

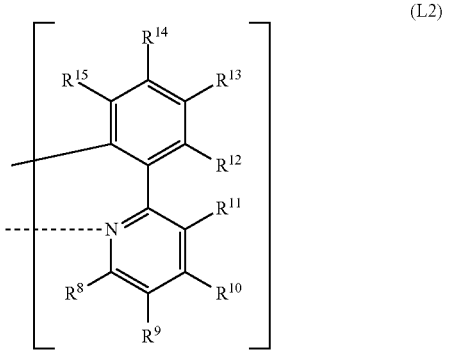

wherein, in formula (L2), $R^8$, $R^9$, $R^{10}$, $R^{11}$, $R^{12}$, $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; and when two groups represented by the formula (1-1) are present, the groups represented by the formula (1-1) may be the same as or different from each other; and when two groups represented by the formula (1-2) are present, the groups represented by the formula (1-2) may be the same as or different from each other.

17. The composition according to claim 8, further comprising a solvent or a dispersion medium.

18. A composition comprising the metal-containing polymer compound according claim 12, and a solvent or a dispersion medium.

19. A film comprising a metal complex represented by formula (1):

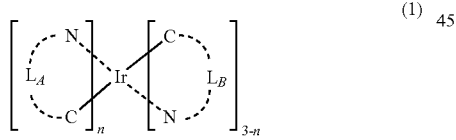

wherein:

in formula (1), n is 1 or 2: $L_A$ and $L_B$ each independently represent a moiety of a group bonded to an iridium atom except for coordinating atoms; a group represented by formula (1-1):

means a group represented by formula (L1):

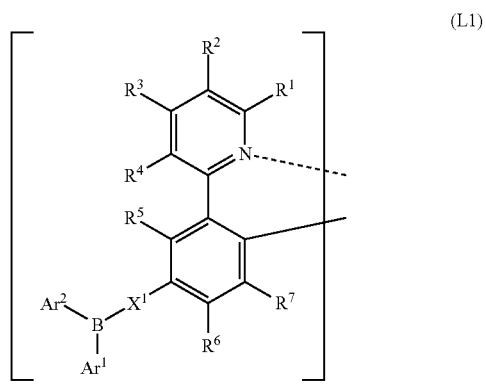

wherein, in formula (L1), $R^1$, $R^2$, $R^3$, $R^4$, $R^5$, $R^6$ and $R^7$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group; $Ar^1$ and $Ar^2$ each independently represent an aryl group optionally having a substituent or a monovalent aromatic heterocyclic group optionally having a substituent; $X^1$ represents a bivalent group in which two or more groups selected from among the group consisting of an arylene group, a bivalent aromatic heterocyclic group, and an ethynylene group are directly bonded to each other, an arylene group, a bivalent aromatic heterocyclic group, an ethynylene group, or a direct bond;

a group represented by formula (1-2):

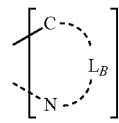

is different from the group represented by the formula (1-1) and means a group represented by formula (L2):

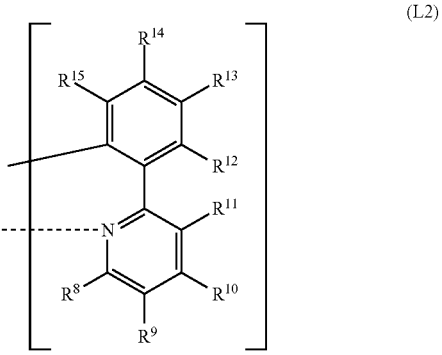

wherein, in formula (L2), $R^8$, $R^9$, $R^{10}$, $R^{11}$, $R^{12}$, $R^{13}$, $R^{14}$ and $R^{15}$ each independently represent a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, an alkenyl group, an alkynyl group, a halogen atom, or a cyano group); and when two groups represented by the formula (1-1) are present, the groups represented by the formula (1-1) may be the same as or different from each other; and when two groups represented by the formula (1-2) are present, the groups represented by the formula (1-2) may be the same as or different from each other.

20. A film comprising the metal-containing polymer compound according to claim 12.

21. A film comprising the composition according to claim 8.

22. A device comprising the film according to claim 19.

23. A device comprising the film according to claim 20.

24. The device according to claim 22, wherein the device is a light-emitting device.

\* \* \* \* \*